United States Patent
Hofmeister et al.

(10) Patent No.: US 7,241,775 B2
(45) Date of Patent: Jul. 10, 2007

(54) COMPOSITION, PROCESS OF MAKING, AND MEDICAL USE OF SUBSTITUTED 4-PHENYLTETRAHYDROISOQUINOLINES

(75) Inventors: Armin Hofmeister, Oppenheim (DE); Uwe Heinelt, Wiesbaden (DE); Hans-Jochen Lang, Hofheim (DE); Wendelin Frick, Hunstetten-Beuerbach (DE); Markus Bleich, Hunfelden-Dauborn (DE); Klaus Wirth, Kriftel (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 355 days.

(21) Appl. No.: 10/807,781

(22) Filed: Mar. 24, 2004

(65) Prior Publication Data

US 2005/0009863 A1 Jan. 13, 2005

Related U.S. Application Data

(60) Provisional application No. 60/493,859, filed on Aug. 8, 2003.

(30) Foreign Application Priority Data

Mar. 24, 2003 (DE) ................. 103 12 963

(51) Int. Cl.
*C07D 217/12* (2006.01)
*A61K 31/47* (2006.01)

(52) U.S. Cl. .............. 514/310; 514/307; 546/139; 546/143; 546/146

(58) Field of Classification Search .......... 546/139, 546/143, 146; 514/307, 310
See application file for complete search history.

(56) References Cited

U.S. PATENT DOCUMENTS 3,666,763 A 5/1972 Grethe et al.

FOREIGN PATENT DOCUMENTS

| WO | WO 01/32624 | 5/2001 |
| WO | WO 03/051866 | 6/2003 |
| WO | WO 03/055490 | 7/2003 |

OTHER PUBLICATIONS

U.S. Appl. No. 10/309,352, filed Dec. 4, 2002, Hofmeister.
U.S. Appl. No. 10/324,041, filed Dec. 20, 2002, Hofmeister.
Ben-Ishai, et al., *Intra vs. Intermolecular Amidoalkylation of Aromatics*, Tetrahedron; 43; 2; 1987; pp. 439-450.
Cuevas, et al., alpha'-Silylated Tertiary Benzamides as Dual Ortho- and alpha'-Carbanion Synthons. , Tetrahedron Letters; 30; 43;1989; pp. 5837-5840.
Fliegel Larry et al., Regulation And Characterization Of The Na+/H+ Exchanger, Biochem. Cell Biology, 76, (1998), pp. 735-741.
Furstner, et al., Titanium-Induced Syntheses of Furans, Benzofurans and Indoles., Tetrahedron; 48;29;1992; pp. 5991-6010.
Kano, et al., A Synthesis of Simple 4,4-Disubstituted Tetrahydroisoquinolines, Chem. Pharm. Bull.; 33;1;1985; p. 340.
Kihara, et al., New Norepinephrine Potentiators: Synthesis and Structure-Activity Relationships of a Series of 4-Phenyl-1,2,3,4-tetrahydroisoquinolin-4-ols, Chem. Pharma Bull.; 42(1); 1994; pp. 67-73.
Kihara, et al., Synthesis and Enantioselectivity of Optically Active 1- and 3-Substituted 4-Phenyl-1,2,3,4-tetrahydrisoquinolin-4-ols and Related Compounds as Norepiniephrine Potentiators, Chem. Pharma. Bull.; 43(9); 1995; pp. 1543-1546.
Ma E. et al., Expression And Localization Of Na+/H+ Exchangers in Rat Central Nervous System, Neuroscience, 79, 2, (1997), pp. 591-603.
Meindl, et al., Benzylamines: Synthesis and Evaluation of Antimycobacterial Properties, J. Med. Chem.; 27; 1984; pp. 1111-1118.
Zhao, et al., A Practical Synthesis of 4-(3',4'-Dihydroxyphenyl)-1,2,3,4-tetrahydroisoquinoline, OPPI Briefs; 27;4;1995; pp. 513-516.

*Primary Examiner*—Zinna N. Davis
(74) *Attorney, Agent, or Firm*—Craig M. Bell

(57) ABSTRACT

Substituted 4-phenyltetrahydroisoquinolines of formula I, process for their preparation, their use as a medicament and medicaments containing them.

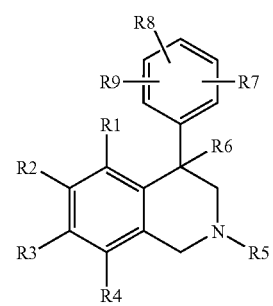

The compounds of formula I can be used, among other uses, in the event of renal disorders such as acute or chronic renal failure, in the event of disorders of biliary function, in the event of respiratory disorders such as snoring or sleep apneas or in the event of stroke.

13 Claims, No Drawings

COMPOSITION, PROCESS OF MAKING, AND MEDICAL USE OF SUBSTITUTED 4-PHENYLTETRAHYDROISOQUINOLINES

FIELD OF THE INVENTION

The invention relates to compounds of the substituted 4-phenyltetrahydroisoquinoline type. Medicaments which comprise compounds of this type are useful in the prevention or treatment of various disorders. For instance, the compounds can be used, among other uses, in the event of renal disorders such as acute or chronic renal failure, in the event of disorders of biliary function, in the event of respiratory disorders such as snoring or sleep apneas or in the event of stroke.

SUMMARY OF THE INVENTION

The invention relates to compounds of the formula I

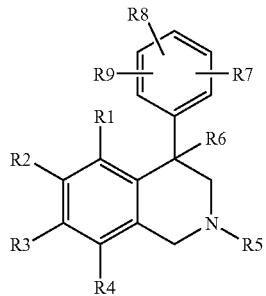

where:
R1, R2, R3 and R4 are each independently H, F, Cl, Br, I, CN, $NO_2$, OH, alkyl having 1, 2, 3, 4, 5, 6, 7 or 8 carbon atoms of which some or all may be fluorinated, cycloalkyl having 3, 4, 5, 6, 7 or 8 carbon atoms of which some or all may be fluorinated, O-alkyl having 1, 2, 3, 4, 5, 6, 7 or 8 carbon atoms of which some or all may be fluorinated, $O_k$—$(CH_2)_l$-phenyl, heteroaryl having 1, 2, 3 or 4 nitrogen atoms or 1 oxygen atom or 1 sulfur atom, $O_h$—$SO_j$—R10, NR14R15, CONR16R17, COOR18 or OCOR18;
k is 0 or 1;
l is 0, 1, 2, 3 or 4;
h is 0 or 1;
j is 0, 1 or 2;
R10 is alkyl having 1, 2, 3, 4, 5, 6, 7 or 8 carbon atoms of which some or all may be fluorinated, OH, O-alkyl having 1, 2, 3, 4, 5, 6, 7 or 8 carbon atoms of which some or all may be fluorinated or NR11R12;
R11 and R12 are each independently hydrogen, alkyl having 1, 2, 3, 4, 5, 6, 7 or 8 carbon atoms of which some or all may be fluorinated and one or more $CH_2$ groups may be replaced by O, NR13, CO or CS,
R13 is H or alkyl having 1, 2, 3, 4, 5, 6, 7 or 8 carbon atoms of which some or all may be fluorinated,
or
R11 and R12 together with the nitrogen atom which bonds them together may form a 5- or 6-membered ring;
R14 and R15 are each independently H, alkyl having 1, 2, 3, 4, 5, 6, 7 or 8 carbon atoms of which some or all may be fluorinated and one or more $CH_2$ groups may be replaced by O, CO, CS or NR19,
or
R14 and R15 together with the nitrogen atom which bonds them together may form a 5- or 6-membered ring;
R16 and R17 are each independently H, alkyl having 1, 2, 3, 4, 5, 6, 7 or 8 carbon atoms of which some or all may be fluorinated and one or more $CH_2$ groups may be replaced by O, CO, CS or NR19,
or
R16 and R17 together with the nitrogen atom which bonds them together may form a 5- or 6-membered ring;
R19 is H or alkyl having 1, 2, 3 or 4 carbon atoms of which some or all may be fluorinated;
R18 is H or alkyl having 1, 2, 3, 4, 5, 6, 7 or 8 carbon atoms of which some or all may be fluorinated;
R5 is H, alkyl having 1, 2, 3, 4, 5, 6, 7 or 8 carbon atoms of which some or all may be fluorinated, cycloalkyl having 3, 4, 5, 6, 7 or 8 carbon atoms of which some or all may be fluorinated, COR20 or $SO_2R20$;
R20 is H or alkyl having 1, 2, 3 or 4 carbon atoms of which some or all may be fluorinated;
R6 is H, OH, F, Cl, Br, alkyl having 1, 2, 3, 4, 5, 6, 7 or 8 carbon atoms of which some or all may be fluorinated, cycloalkyl having 3, 4, 5, 6, 7 or 8 carbon atoms of which some or all may be fluorinated, O-alkyl having 1, 2, 3, 4, 5, 6, 7 or 8 carbon atoms of which some or all may be fluorinated, or O-acyl having 1, 2, 3, 4, 5, 6, 7 or 8 carbon atoms of which some or all may be fluorinated;
R7, R8 and R9 are each independently H, F, Cl, Br, I, OH, alkyl having 1, 2, 3, 4, 5, 6, 7 or 8 carbon atoms of which some or all may be fluorinated, cycloalkyl having 3, 4, 5, 6, 7 or 8 carbon atoms of which some or all may be fluorinated, O-alkyl having 1, 2, 3, 4, 5, 6, 7 or 8 carbon atoms of which some or all may be fluorinated, $O_v$—$SO_w$—R47, COR47, COOR60, NR51R52 or a -L-G group;
v is 0 or 1;
w is 2 or 3;
R47 is H, alkyl having 1, 2, 3, 4, 5, 6, 7 or 8 carbon atoms of which some or all may be fluorinated or NR48R49;
R48 and R49 are each independently H, alkyl having 1, 2, 3, 4, 5, 6, 7 or 8 carbon atoms of which some or all may be fluorinated and one or more $CH_2$ groups may be replaced by O, CO, CS or NR50,
R50 is H or alkyl having 1, 2, 3, 4, 5 or 6 carbon atoms of which some or all may be fluorinated;
or
R48 and R49 together with the nitrogen atom which bonds them together form a 5, 6, 7 or 8-membered ring;
R60 is H, alkyl having 1, 2, 3, 4, 5, 6, 7 or 8 carbon atoms of which some or all may be fluorinated;
R51 and R52 are each independently H, alkyl having 1, 2, 3, 4, 5, 6, 7 or 8 carbon atoms of which some or all may be fluorinated, acyl having 1, 2, 3, 4, 5, 6, 7 or 8 carbon atoms of which some or all may be fluorinated and one or more $CH_2$ groups may be replaced by O or NR53,
R53 is H or alkyl having 1, 2, 3, 4, 5 or 6 carbon atoms of which some or all may be fluorinated;
or
R51 and R52 together with the nitrogen atom which bonds them together form a 5, 6, 7 or 8-membered ring;
L is —$CH_2$—, —O—, —NR30-, —OCO—, —NR30CO—, —NR30CS—, —$NR30SO_2$—, —CONR30-, —COO—, —CSNR30-, —SO$_2$NR30-, —NR30CONR31-, —NR30COO—, —NR30CSNR31- or —NR30SO$_2$NR31-;

R30 and R31 are each independently H, alkyl having 1, 2, 3, 4, 5, 6, 7 or 8 carbon atoms of which some or all may be fluorinated or cycloalkyl having 3, 4, 5, 6, 7 or 8 carbon atoms of which some or all may be fluorinated;

G is a C$_a$(OR32)$_x$H$_{2a+1-x}$ group where one or more CH$_2$ groups may be replaced by O or NR33, C$_b$(OR32)$_y$ H$_{2b-1-y}$ where one or more CH$_2$ groups may be replaced by O or NR33, C$_c$H$_{2c+1}$ where two or more CH$_2$ groups are replaced by O or NR33, —(CH$_2$)$_z$—COOR34, —(CH$_2$)$_z$—SO$_3$R34, —(CH$_2$)$_z$—N$^+$R35R36R37 where one or more hydrogen atoms of the —(CH$_2$)$_z$ units may be replaced by OR32 groups, —CR38R39-COOR40 or —CR38R39NR41R42, a is 2, 3, 4, 5, 6, 7 or 8;
x is 2, 3, 4, 5, 6, 7 or 8;
  R32 is H, alkyl having 1, 2, 3, 4, 5 or 6 carbon atoms of which some or all may be fluorinated or acyl having 1, 2, 3, 4, 5 or 6 carbon atoms of which some or all may be fluorinated;
  R33 is H or alkyl having 1, 2, 3, 4, 5 or 6 carbon atoms of which some or all may be fluorinated;
  b is 3, 4, 5, 6 or 7;
  y is 2, 3, 4, 5, 6 or 7;
  c is 3, 4, 5, 6, 7 or 8;
  z is 0, 1, 2, 3 or 4;
  R34, R35, R36 and R37 are each independently H or alkyl having 1, 2, 3, 4, 5 or 6 carbon atoms of which some or all may be fluorinated;
  R38 is —(CH$_2$)$_n$—Y;
  n is 0, 1, 2, 3 or 4;
  Y is H, alkyl having 1, 2, 3, 4, 5, 6, 7 or 8 carbon atoms of which some or all may be fluorinated and one or more CH$_2$ groups may be replaced by O, S or NR43, or is —COOR44, —CONR45R46, —NHC(NH)NH$_2$, phenyl or heteroaryl, and the phenyl and heteroaryl radicals may be substituted by up to three substituents selected from the group of CH$_3$, CF$_3$, OH, OCH$_3$ and NH$_2$;
  R43, R44, R45 and R46 are each independently H or alkyl having 1, 2, 3, 4, 5 or 6 carbon atoms of which some or all may be fluorinated;
  R39 is H or alkyl having 1, 2, 3, 4, 5, 6, 7 or 8 carbon atoms of which some or all may be fluorinated;
  R40 is H or alkyl having 1, 2, 3, 4, 5, 6, 7 or 8 carbon atoms of which some or all may be fluorinated;
  R41 and R42 are each independently H, alkyl having 1, 2, 3, 4, 5, 6, 7 or 8 carbon atoms of which some or all may be fluorinated or acyl having 1, 2, 3, 4, 5, 6, 7 or 8 carbon atoms of which some or all may be fluorinated;

in which at least one of the R7, R8 or R9 radicals has to be defined by the -L-G group, and also its pharmaceutically acceptable salts and trifluoroacetates.

Preference is given to compounds of the formula I where R1, R2, R3 and R4, are each independently H, F, Cl, Br, I, CN, NO$_2$, OH, alkyl having 1, 2, 3 or 4 carbon atoms of which some or all may be fluorinated, cycloalkyl having 3, 4, 5 or 6 carbon atoms of which some or all may be fluorinated, O-alkyl having 1, 2, 3 or 4 carbon atoms of which some or all may be fluorinated, O-phenyl, SO$_2$R10, NR14R15, CONR16R17, COOR18 or OCOR18;

R10 is alkyl having 1, 2, 3 or 4 carbon atoms of which some or all may be fluorinated, OH or NR11R12;
  R11 and R12 are each independently hydrogen, alkyl having 1, 2, 3 or 4 carbon atoms of which some or all may be fluorinated, or acyl having 1, 2, 3 or 4 carbon atoms of which some or all may be fluorinated,
  or
  R11 and R12 together with the nitrogen atom which bonds them together form a 5- or 6-membered ring, from the group of 1-pyrrolyl, 1-piperidinyl, 1-piperazinyl, 1-N-methylpiperazinyl and 4-morpholinyl;
  R14 and R15 are each independently H, alkyl having 1, 2, 3 or 4 carbon atoms of which some or all may be fluorinated or acyl having 1, 2, 3 or 4 carbon atoms of which some or all may be fluorinated,
  or
  R14 and R15 together with the nitrogen atom which bonds them together form a 5- or 6-membered ring, from the group of 1-pyrrolyl, 1-piperidinyl, 1-piperazinyl, 1-N-methylpiperazinyl and 4-morpholinyl;
  R16 and R17 are each independently H or alkyl having 1, 2, 3 or 4 carbon atoms of which some or all may be fluorinated,
  or
  R16 and R17 together with the nitrogen atom which bonds them together form a 5- or 6-membered ring, from the group of 1-pyrrolyl, 1-piperidinyl, 1-piperazinyl, 1-N-methylpiperazinyl and 4-morpholinyl;
  R18 is H or alkyl having 1, 2, 3 or 4 carbon atoms of which some or all may be fluorinated;
R5 is H, alkyl having 1, 2, 3 or 4 carbon atoms of which some or all may be fluorinated, or cycloalkyl having 3, 4, 5 or 6 carbon atoms of which some or all may be fluorinated;
R6 is H, OH, F, Cl, Br, alkyl having 1, 2, 3 or 4 carbon atoms of which some or all may be fluorinated, cycloalkyl having 3, 4, 5 or 6 carbon atoms of which some or all may be fluorinated, O-alkyl having 1, 2, 3 or 4 carbon atoms of which some or all may be fluorinated, or O-acyl having 1, 2, 3 or 4 carbon atoms of which some or all may be fluorinated;
R7, R8 and R9 are each independently H, F, Cl, Br, I, OH, alkyl having 1, 2, 3 or 4 carbon atoms of which some or all may be fluorinated, cycloalkyl having 3, 4, 5 or 6 carbon atoms of which some or all may be fluorinated, O-alkyl having 1, 2, 3 or 4 carbon atoms of which some or all may be fluorinated, O$_v$—SO$_w$—R47, COR47, COOR60, NR51R52 or a -L-G group;
v is 0 or 1;
w is 2 or 3;
R47 is H, alkyl having 1, 2, 3 or 4 carbon atoms of which some or all may be fluorinated, or NR48R49;
  R48 and R49 are each independently H, alkyl having 1, 2, 3 or 4 carbon atoms of which some or all may be fluorinated, acyl having 1, 2, 3 or 4 carbon atoms of which some or all may be fluorinated,
  or
  R48 and R49 together with the nitrogen atom which bonds them together form a 5- or 6-membered ring, from the group of 1-pyrrolyl, 1-piperidinyl, 1-piperazinyl, 1-N-methylpiperazinyl and 4-morpholinyl;
R60 is H, alkyl having 1, 2, 3 or 4 carbon atoms of which some or all may be fluorinated;
R51 and R52 are each independently H, alkyl having 1, 2, 3 or 4 carbon atoms of which some or all may be fluorinated, acyl having 1, 2, 3 or 4 carbon atoms of which some or all may be fluorinated, or R51 and R52 together with the nitrogen atom which bonds them together form a 5- or 6-membered ring, from the group of 1-pyrrolyl, 1-piperidinyl, 1-piperazinyl, 1-N-methylpiperazinyl and 4-morpholinyl;

L is —$CH_2$—, —O—, —NR30-, —OCO—, —NR30CO—, —NR30CS—, —NR30$SO_2$—, —CONR30-, —COO—, —CSNR30-, —$SO_2$NR30-, —NR30CONR31-, —NR30COO—, —NR30CSNR31- or —NR30$SO_2$NR31-;

where R30 and R31 are each independently H, alkyl having 1, 2, 3 or 4 carbon atoms of which some or all may be fluorinated or cycloalkyl having 3, 4, 5 or 6 carbon atoms of which some or all may be fluorinated;

G is a $C_a(OR32)_xH_{2a+1-x}$ group where one or more $CH_2$ groups may be replaced by O or NR33, $C_b(OR32)_yH_{2b-1-y}$ where one or more $CH_2$ groups may be replaced by O or NR33, $C_cH_{2c+1}$ where two or more $CH_2$ groups are replaced by O or NR33, —$(CH_2)_z$—COOR34, —$(CH_2)_z$—$SO_3$R34, —$(CH_2)_z$—$N^+$R35R36R37 where one or more hydrogen atoms of the —$(CH_2)_z$ units may be replaced by OR32 groups, —CR38R39-COOR40 or —CR38R39NR41R42;

a is 2, 3, 4, 5, 6, 7 or 8;

x is 2, 3, 4, 5, 6, 7 or 8;

R32 is H, alkyl having 1, 2, 3 or 4 carbon atoms of which some or all may be fluorinated or acyl having 1, 2, 3 or 4 carbon atoms of which some or all may be fluorinated;

R33 is H or alkyl having 1, 2, 3 or 4 carbon atoms of which some or all may be fluorinated;

b is 3, 4, 5, 6 or 7;

y is 2, 3, 4, 5, 6 or 7;

c is 3, 4, 5, 6, 7 or 8;

z is 0, 1, 2, 3 or 4;

R34, R35, R36 and R37 are each independently H or alkyl having 1, 2, 3 or 4 carbon atoms of which some or all may be fluorinated;

R38 is —$(CH_2)_n$—Y;

n is 0, 1, 2, 3 or 4;

Y is H, alkyl having 1, 2, 3 or 4 carbon atoms of which some or all may be fluorinated and one or more $CH_2$ groups may be replaced by O, S or NR43, or is COOR44, CONR45R46, NHC(NH)$NH_2$, phenyl or heteroaryl, and the phenyl and heteroaryl radicals may be substituted by up to three substituents selected from the group of $CH_3$, $CF_3$, OH, $OCH_3$ and $NH_2$;

R43, R44, R45 and R46 are each independently H or alkyl having 1, 2, 3 or 4 carbon atoms of which some or all may be fluorinated;

R39 is H or alkyl having 1, 2, 3 or 4 carbon atoms of which some or all may be fluorinated;

R40 is H or alkyl having 1, 2, 3 or 4 carbon atoms of which some or all may be fluorinated;

R41 and R42 are each independently H, alkyl having 1, 2, 3 or 4 carbon atoms of which some or all may be fluorinated, or acyl having 1, 2, 3 or 4 carbon atoms of which some or all may be fluorinated;

in which at least one of the R7, R8 or R9 radicals has to be defined by the -L-G group, and also its pharmaceutically acceptable salts and trifluoroacetates.

Particular preference is given to compounds of the formula I where:

R1, R2, R3 and R4, are each independently H, F, Cl, Br, CN, $NO_2$, OH, $CH_3$, $CH_2CH_3$, $CF_3$, $CH_2CF_3$, $OCH_3$, $OCH_2CH_3$, $OCF_3$, $OCH_2CF_3$, $SO_2R10$, NR14R15, CONR16R17, COOR18 or OCOR18, R10 is $CH_3$, $CH_2CH_3$, $CF_3$, $CH_2CF_3$, OH, NR11R12, R11 and R12 are each independently H, $CH_3$, $CH_2CH_3$, $CF_3$, $CH_2CF_3$, $COCH_3$, $COCH_2CH_3$, $COCF_3$ or $COCH_2CF_3$, or R11 and R12 together with the nitrogen atom which bonds them together form a 5- or 6-membered ring from the group of 1-pyrrolyl, 1-piperidinyl, 1-piperazinyl, 1-N-methylpiperazinyl and 4-morpholinyl;

R14 and R15 are each independently H, $CH_3$, $CH_2CH_3$, $CF_3$, $CH_2CF_3$, $COCH_3$, $COCH_2CH_3$, $COCF_3$ or $COCH_2CF_3$, or R14 and R15 together with the nitrogen atom which bonds them together form a 5- or 6-membered ring from the group of 1-pyrrolyl, 1-piperidinyl, 1-piperazinyl, 1-N-methylpiperazinyl and 4-morpholinyl;

R16 and R17 are each independently H, $CH_3$, $CH_2CH_3$, $CF_3$ or $CH_2CF_3$, or R16 and R17 together with the nitrogen atom which bonds them together form a 5- or 6-membered ring from the group of 1-pyrrolyl, 1-piperidinyl, 1-piperazinyl, 1-N-methylpiperazinyl and 4-morpholinyl;

R18 is H, $CH_3$, $CH_2CH_3$, $CF_3$ or $CH_2CF_3$;

R5 is H, $CH_3$, $CH_2CH_3$, $CF_3$ or $CH_2CF_3$;

R6 is H, OH, $CH_3$, $CH_2CH_3$, $CF_3$, $CH_2CF_3$, $OCH_3$, $OCH_2CH_3$, $OCF_3$, $OCH_2CF_3$, $OCOCH_3$, $OCOCH_2CH_3$, $OCOCF_3$ or $OCOCH_2CF_3$;

R7, R8 and R9 are each independently H, F, Cl, Br, I, OH, $CH_3$, $CH_2CH_3$, $CF_3$, $CH_2CF_3$, $OCH_3$, $OCH_2CH_3$, $OCF_3$, $OCH_2CF_3$, $SO_2R47$, $SO_3R60$, COR47, COOR60, NR51R52 or a -L-G group;

R47 is H, $CH_3$, $CH_2CH_3$, $CF_3$, $CH_2CF_3$ or NR48R49;

R48 and R49 are each independently H, $CH_3$, $CH_2CH_3$, $CF_3$, $CH_2CF_3$, $COCH_3$, $COCH_2CH_3$, $COCF_3$ or $COCH_2CF_3$, or R48 and R49 together with the nitrogen atom which bonds them together form a 5- or 6-membered ring from the group of 1-pyrrolyl, 1-piperidinyl, 1-piperazinyl, 1-N-methylpiperazinyl and 4-morpholinyl;

R60 is H, $CH_3$, $CH_2CH_3$, $CF_3$, $CH_2CF_3$;

R51 and R52 are each independently H, $CH_3$, $CH_2CH_3$, $CF_3$, $CH_2CF_3$, $COCH_3$, $COCH_2CH_3$, $COCF_3$ or $COCH_2CF_3$, or R51 and R52 together with the nitrogen atom which bonds them together form a 5- or 6-membered ring from the group of 1-pyrrolyl, 1-piperidinyl, 1-piperazinyl, 1-N-methylpiperazinyl and 4-morpholinyl;

L is —$CH_2$—, —O—, —NR30-, —OCO—, —NR30CO—, —NR30CS—, —NR30$SO_2$—, —CONR30-, —COO—, —CSNR30-, —$SO_2$NR30-, —NR30CONR31-, —NR30COO—, —NR30CSNR31- or —NR30$SO_2$NR31-;

R30 and R31 are each independently H, $CH_3$, $CH_2CH_3$, $CF_3$ or $CH_2CF_3$;

G is a $C_a(OR32)_xH_{2a+1-x}$ group where one or more $CH_2$ groups may be replaced by O or NR33, $C_b(OR32)_yH_{2b-1-y}$ where one or more $CH_2$ groups may be replaced by O or NR33, $C_cH_{2c+1}$ where two or more $CH_2$ groups are replaced by O or NR33, —$(CH_2)_z$—COOR34, —$(CH_2)_z$—SO$_3$R34, —$(CH_2)_z$—N$^+$R35R36R37 where 1 or 2 hydrogen atoms of the —$(CH_2)_z$ units may be replaced by OR32 groups, —CR38R39-COOR40 or —CR38R39NR41R42;

a is 2, 3, 4, 5, 6, 7 or 8;
x is 2, 3, 4, 5, 6, 7 or 8;
R32 is H, CH$_3$, CH$_2$CH$_3$, CF$_3$, CH$_2$CF$_3$, COCH$_3$, COCH$_2$CH$_3$, COCF$_3$ or COCH$_2$CF$_3$;
R33 is H, CH$_3$, CH$_2$CH$_3$, CF$_3$ or CH$_2$CF$_3$;
b is 3, 4, 5, 6 or 7;
y is 2, 3, 4, 5, 6 or 7;
c is 3, 4, 5, 6, 7 or 8;
z is 1 or 2;
R34, R35, R36 and R37 are each independently H, CH$_3$, CH$_2$CH$_3$, CF$_3$ or CH$_2$CF$_3$;
R38 is —$(CH_2)_n$—Y;
n is 0, 1, 2, 3 or 4;
Y is H, alkyl having 1, 2, 3 or 4 carbon atoms of which some or all may be fluorinated and one or more $CH_2$ groups may be replaced by O, S or NR43, or is COOR44, CONR45R46, NHC(NH)NH$_2$, phenyl or heteroaryl, and the phenyl and heteroaryl radicals may be substituted by up to 3 substituents selected from the group of CH$_3$, CF$_3$, OH, OCH$_3$ or NH$_2$;
R43, R44, R45 and R46 are each independently H, CH$_3$, CH$_2$CH$_3$, CF$_3$ or CH$_2$CF$_3$;
R39 is H, CH$_3$, CH$_2$CH$_3$, CF$_3$ or CH$_2$CF$_3$;
R40 is H, CH$_3$, CH$_2$CH$_3$, CF$_3$ or CH$_2$CF$_3$;
R41 and R42 are each independently H, CH$_3$, CH$_2$CH$_3$, CF$_3$, CH$_2$CF$_3$, COCH$_3$, COCH$_2$CH$_3$, COCF$_3$ or COCH$_2$CF$_3$;

in which at least one of the R7, R8 or R9 radicals has to be defined by the -L-G group, and also its pharmaceutically acceptable salts and trifluoroacetates.

Very particular preference is given to compounds of the formula I where

R1, R2, R3 and R4, are each independently H, F, Cl, Br, CN, NO$_2$, OH, CH$_3$, CH$_2$CH$_3$, CF$_3$, CH$_2$CF$_3$, OCH$_3$, OCH$_2$CH$_3$, OCF$_3$, OCH$_2$CF$_3$, SO$_2$R10, NR14R15, CONR16R17, COOR18 or OCOR18;
R10 is CH$_3$, CH$_2$CH$_3$, CF$_3$, CH$_2$CF$_3$, OH or NR11R12;
R11 and R12 are each independently H, CH$_3$, CH$_2$CH$_3$, CF$_3$, CH$_2$CF$_3$, COCH$_3$, COCH$_2$CH$_3$, COCF$_3$ or COCH$_2$CF$_3$;
R14 and R15 are each independently H, CH$_3$, CH$_2$CH$_3$, CF$_3$, CH$_2$CF$_3$, COCH$_3$, COCH$_2$CH$_3$, COCF$_3$ or COCH$_2$CF$_3$;
R16 and R17 are each independently H, CH$_3$, CH$_2$CH$_3$, CF$_3$ or CH$_2$CF$_3$;
R18 is H, CH$_3$, CH$_2$CH$_3$, CF$_3$ or CH$_2$CF$_3$;
R5 is CH$_3$;
R6 is H;
R7, R8 and R9 are each independently H, F, Cl, Br, I, OH, CH$_3$, CH$_2$CH$_3$, CF$_3$, CH$_2$CF$_3$, OCH$_3$, OCH$_2$CH$_3$, OCF$_3$, OCH$_2$CF$_3$, SO$_2$R47, SO$_3$R60, COR47, COOR60, NR51R52 or a -L-G group;
R47 is H, CH$_3$, CH$_2$CH$_3$, CF$_3$, CH$_2$CF$_3$ or NR48R49;
R48 and R49 are each independently H, CH$_3$, CH$_2$CH$_3$, CF$_3$, CH$_2$CF$_3$, COCH$_3$, COCH$_2$CH$_3$, COCF$_3$ or COCH$_2$CF$_3$,
or
R48 and R49 together with the nitrogen atom which bonds them together form a 5- or 6-membered ring from the group of 1-pyrrolyl, 1-piperidinyl, 1-piperazinyl, 1-N-methylpiperazinyl and 4-morpholinyl;
R60 is H, CH$_3$, CH$_2$CH$_3$, CF$_3$, CH$_2$CF$_3$;
R51 and R52 are each independently H, CH$_3$, CH$_2$CH$_3$, CF$_3$, CH$_2$CF$_3$, COCH$_3$, COCH$_2$CH$_3$, COCF$_3$ or COCH$_2$CF$_3$
or
R51 and R52 together with the nitrogen atom which bonds them together form a 5- or 6-membered ring from the group of 1-pyrrolyl, 1-piperidinyl, 1-piperazinyl, 1-N-methylpiperazinyl and 4-morpholinyl;
L is —CH$_2$—, —O—, —NR30-, —OCO—, —NR30CO—, —NR30CS—, —NR30SO$_2$—, —CONR30-, —COO—, —CSNR30-, —SO$_2$NR30-, —NR30CONR31-, —NR30COO—, —NR30CSNR31- or —NR30SO$_2$NR31-;
R30 and R31 are each independently H, CH$_3$, CH$_2$CH$_3$, CF$_3$ or CH$_2$CF$_3$;
G is a group $C_a(OR32)_xH_{2a+1-x}$ where one or more $CH_2$ groups may be replaced by O or NR33, $C_b(OR32)_yH_{2b-1-y}$ where one or more $CH_2$ groups may be replaced by O or NR33, $C_cH_{2c+1}$ where two or more $CH_2$ groups are replaced by O or NR33, —$(CH_2)_z$—COOR34, —$(CH_2)_z$—SO$_3$R34, —$(CH_2)_z$—N$^+$R35R36R37 where 1 or 2 hydrogen atoms of the —$(CH_2)_z$ units may be replaced by OR32 groups, —CR38R39-COOR40 or —CR38R39NR41R42;
a is 2, 3, 4, 5, 6, 7 or 8;
x is 2, 3, 4, 5, 6, 7 or 8;
R32 is H, CH$_3$, CH$_2$CH$_3$, CF$_3$, CH$_2$CF$_3$, COCH$_3$, COCH$_2$CH$_3$, COCF$_3$ or COCH$_2$CF$_3$;
R33 is H, CH$_3$, CH$_2$CH$_3$, CF$_3$ or CH$_2$CF$_3$;
b is 3, 4, 5, 6 or 7;
y is 2, 3, 4, 5, 6 or 7;
c is 3, 4, 5, 6, 7 or 8;
z is 1 or 2;
R34, R35, R36 and R37 are each independently H, CH$_3$, CH$_2$CH$_3$, CF$_3$ or CH$_2$CF$_3$;
R38 is —$(CH_2)_n$—Y;
n is 0, 1, 2, 3 or 4;
Y is H, alkyl having 1, 2, 3 or 4 carbon atoms of which some or all may be fluorinated and one or more $CH_2$ groups may be replaced by O, S or NR43, or is COOR44, CONR45R46, NHC(NH)NH$_2$, phenyl or heteroaryl, and the phenyl and heteroaryl radicals may be substituted by up to 3 substituents selected from the group of CH$_3$, CF$_3$, OH, OCH$_3$ or NH$_2$;
R43, R44, R45 and R46 are each independently H, CH$_3$, CH$_2$CH$_3$, CF$_3$ or CH$_2$CF$_3$,
R39 is H;
R40 is H, CH$_3$, CH$_2$CH$_3$, CF$_3$ or CH$_2$CF$_3$;
R41 and R42 are each independently H, CH$_3$, CH$_2$CH$_3$, CF$_3$, CH$_2$CF$_3$, COCH$_3$, COCH$_2$CH$_3$, COCF$_3$ or COCH$_2$CF$_3$;

in which at least one of the R7, R8 or R9 radicals has to be defined by the -L-G group, and also its pharmaceutically acceptable salts and trifluoroacetates.

In one embodiment, preference is given to compounds of the formula I in which R1 and R3 are described by H.

In a further embodiment, preference is given to compounds of the formula I in which R2 and R4 are described by Cl.

In one embodiment, preference is given to compounds of the formula I in which R5 is described by H, CH$_3$ or CF$_3$.

In another embodiment, preference is given to compounds of the formula I in which R6 is described by H, OH, CH$_3$, CF₃, OCH₃ or OCOCH₃, and preference is given to compounds in which R6 is described by H.

In one embodiment, preference is given to compounds of the formula I in which R7, R8 and R9 are each independently described by H, OH, CH₃, CF₃, OCH₃, SO₂R47, SO₃R60, COR47, COOR60, NR51R52 or a -L-G group, where R47 is H, CH₃ or NR48R49;
R48 and R49 are each independently H, CH₃ or COCH₃;
R60 is H, CH₃;
R51 and R52 are each independently H, CH₃, CH₂CH₃ or COCH₃;
L is —NR30CO—, —CONR30- or —NR30CONR31-;
R30 and R31 are each H;
G is a group of the form $C_a(OR32)_xH_{2a+1-x}$, $C_b(OR32)_y$ $H_{2b-1-y}$ where one CH₂ group may be replaced by O, $C_cH_{2c+1}$ where two or more CH₂ groups are replaced by O or NR33, —(CH₂)₂—COOH, —(CH₂)₂—SO₃H, —(CH₂)₂—N⁺(CH₃)₃ where 1 or 2 hydrogen atoms of the —(CH₂)₂ units may be replaced by OH groups, —CR38R39-COOR40 or —CR38R39NR41R42
a is 3, 4, 5 or 6;
x is 2, 3, 4 or 5;
R32 is H;
b is 5 or 6;
y is 2, 3, 4 or 5;
c is 6, 7 or 8;
R33 is H or CH₃;
R38 is H, alkyl having 1, 2, 3 or 4 carbon atoms, CH₂OH, CH₂SH, CH₂NH₂, CH(OH)CH₃, CH₂CH₂SCH₃, CH₂CH₂CH₂NH₂, CH₂CH₂CH₂CH₂NH₂, CH₂CH₂CH₂NHC(NH) NH₂, CH₂COOH, CH₂CONH₂, CH₂CH₂COOR44, CH₂CH₂CONH₂, COOH, phenyl, 4-hydroxyphenyl, 4-imidazolyl or 3-indolyl;
R39 is H;
R40 is H, CH₃ or CH₂CH₃;
R41 and R42 are each independently H, CH₃ or COCH₃;
R44 is H, CH₃ or CH₂CH₃;

in which at least one of the R7, R8 or R9 radicals has to be defined by the -L-G group.

In one embodiment, preference is given to compounds of the formula I in which one of the R7, R8 or R9 radicals is described by LG and the other R7, R8, R9 radicals by H, OH, CH₃, CF₃, OCH₃, SO₂R47, SO₃R60, COR47, COOR60 or NR51R52, in particular by hydrogen or COOH; particular preference is given to compounds of the formula I, in which one of the R7, R8 or R9 radicals is described by LG and the other R7, R8, R9 radicals are each described by H.

In one embodiment, preference is given to compounds of the formula I in which two of the R7, R8 or R9 radicals are each described by LG and one of the R7, R8 or R9 radicals by hydrogen.

Especially preferred are compounds of the formula I selected from the group of

N-[4-(6,8-dichloro-2-methyl-1,2,3,4-tetrahydroisoquinolin-4-yl)phenyl]-2,3,4,5,6-pentahydroxyhexanamide,
N-[3-(6,8-dichloro-2-methyl-1,2,3,4-tetrahydroisoquinolin-4-yl)phenyl]-2,3,4,5,6-pentahydroxyhexanamide,
N-[2-(6,8-dichloro-2-methyl-1,2,3,4-tetrahydroisoquinolin-4-yl)phenyl]-2,3,4,5,6-pentahydroxyhexanamide,
N-[3-((S)-6,8-dichloro-2-methyl-1,2,3,4-tetrahydroisoquinolin-4-yl)phenyl]-2,3,4,5,6-pentahydroxyhexanamide,
N-[3-((R)-6,8-dichloro-2-methyl-1,2,3,4-tetrahydroisoquinolin-4-yl)phenyl]-2,3,4,5,6-pentahydroxyhexanamide,
1-[3-(6,8-dichloro-2-methyl-1,2,3,4-tetrahydroisoquinolin-4-yl)phenyl]-3-(2-hydroxy-1-hydroxymethylethyl)urea,
1-[3-(6,8-dichloro-2-methyl-1,2,3,4-tetrahydroisoquinolin-4-yl)phenyl]-3-(2-hydroxy-1,1-bishydroxymethylethyl)urea,
1-[3-(6,8-dichloro-2-methyl-1,2,3,4-tetrahydroisoquinolin-4-yl)phenyl]-3-(2,3,4,5,6-pentahydroxyhexyl)urea,
1-[3-(6,8-dichloro-2-methyl-1,2,3,4-tetrahydroisoquinolin-4-yl)phenyl]-3-(2,4,5-trihydroxy-6-hydroxymethyltetrahydropyran-3-yl)urea,
{N-[3-(6,8-dichloro-2-methyl-1,2,3,4-tetrahydroisoquinolin-4-yl)phenyl]-N'-(1-sulfo-2-ethyl)}urea,
{N-[3-(6,8-dichloro-2-methyl-1,2,3,4-tetrahydroisoquinolin-4-yl)phenyl]-N'-(ethyl-2-trimethylammonium)}urea chloride,
{N-[3-(6,8-dichloro-2-methyl-1,2,3,4-tetrahydroisoquinolin-4-yl)phenyl]-N'(1-carboxy-3-hydroxy-2-propyl)} urea,
{N-[3-(6,8-dichloro-2-methyl-1,2,3,4-tetrahydroisoquinolin-4-yl)phenyl]-N'-(1-carboxy-4-aminocarboxy-2-butyl)}urea,
3-(6,8-dichloro-2-methyl-1,2,3,4-tetrahydroisoquinolin-4-yl)-N-(2,3,4,5,6-pentahydroxyhexyl)benzamide,
3-(6,8-dichloro-2-methyl-1,2,3,4-tetrahydroisoquinolin-4-yl)-N-(2-hydroxy-1-hydroxymethylethyl)benzamide,
2-[3-(6,8-dichloro-2-methyl-1,2,3,4-tetrahydroisoquinolin-4-yl)benzoylamino]-3-hydroxypropionic acid,
2-[3-(6,8-dichloro-2-methyl-1,2,3,4-tetrahydroisoquinolin-4-yl)benzoylamino]succinic acid,
2-[3-(6,8-dichloro-2-methyl-1,2,3,4-tetrahydroisoquinolin-4-yl)benzoylamino]-4-succinamic acid,
N-[3-(6,8-dichloro-2-methyl-1,2,3,4-tetrahydroisoquinolin-4-yl)phenyl]-N'-[1-carboxy-5-guanidino-2-pentyl]urea,
{N-[3-(6,8-dichloro-2-methyl-1,2,3,4-tetrahydroisoquinolin-4-yl)phenyl]-N'-(1-carboxy-4-aminocarboxy-2-butyl)}urea,
{N-[3-(6,8-dichloro-2-methyl-1,2,3,4-tetrahydroisoquinolin-4-yl)phenyl]-N'-(1-carboxy-3-hydroxy-2-propyl)} urea,
1-[3-(6,8-dichloro-2-methyl-1,2,3,4-tetrahydroisoquinolin-4-yl)phenyl]-3-(2-hydroxy-1,1-bishydroxymethylethyl)urea,
1-[3-(6,8-dichloro-2-methyl-1,2,3,4-tetrahydroisoquinolin-4-yl)phenyl]-3-(2,3,4,5,6-pentahydroxyhexyl)urea,
5-(6,8-dichloro-2-methyl-1,2,3,4-tetrahydroisoquinolin-4-yl)-N,N'-bis(2-hydroxy-1-hydroxymethylethyl)isophthalamide,
5-(6,8-dichloro-2-methyl-1,2,3,4-tetrahydroisoquinolin-4-yl)-N,N'-bis(2-hydroxy-1,1-bishydroxymethylethyl) isophthalamide,
5-(6,8-dichloro-2-methyl-1,2,3,4-tetrahydroisoquinolin-4-yl)-N-bis(2-hydroxy-1,1-bishydroxymethylethyl)isophthalamide,
5-(6,8-dichloro-2-methyl-1,2,3,4-tetrahydroisoquinolin-4-yl)-N,N'-bis(2,3,4,5,6-pentahydroxyhexyl)isophthalamide,
5-(6,8-dichloro-2-methyl-1,2,3,4-tetrahydroisoquinolin-4-yl)-N-(2,3,4,5,6-pentahydroxyhexyl)isophthalamide,
2-[3-(1-carboxy-2-hydroxyethylcarbamoyl)-5-(6,8-dichloro-2-methyl-1,2,3,4-tetrahydroisoquinolin-4-yl) benzoylamino]-3-hydroxypropionic acid,
N-[3-(6,8-dichloro-2-methyl-1,2,3,4-tetrahydroisoquinolin-4-yl)phenyl]-2-amino-5-guanidinopentanamide, N-[4-(6,8-dichloro-2-methyl-1,2,3,4-tetrahydroisoquinolin-4-yl)phenyl]-2-amino-5-guanidinopentanamide,
2-amino-N-[3-(6,8-dichloro-2-methyl-1,2,3,4-tetrahydroisoquinolin-4-yl)phenyl]-3-(1H-imidazol-4-yl)propionamide,
2-amino-N-[4-(6,8-dichloro-2-methyl-1,2,3,4-tetrahydroisoquinolin-4-yl)phenyl]-3-(1H-imidazol-4-yl)propionamide,
ethyl {3-[4-(6,8-dichloro-2-methyl-1,2,3,4-tetrahydroisoquinolin-4-yl)phenyl]ureido}-acetate,
ethyl {3-[3-(6,8-dichloro-2-methyl-1,2,3,4-tetrahydroisoquinolin-4-yl)phenyl]ureido}-acetate,
ethyl {3-[2-(6,8-dichloro-2-methyl-1,2,3,4-tetrahydroisoquinolin-4-yl)phenyl]ureido}-acetate,
{3-[3-(6,8-dichloro-2-methyl-1,2,3,4-tetrahydroisoquinolin-4-yl)phenyl]ureido}acetic acid,
{3-[4-(6,8-dichloro-2-methyl-1,2,3,4-tetrahydroisoquinolin-4-yl)phenyl]ureido}acetic acid,
{3-[2-(6,8-dichloro-2-methyl-1,2,3,4-tetrahydroisoquinolin-4-yl)phenyl]ureido}acetic acid,
ethyl {3-[3-(6,8-dichloro-2-methyl-1,2,3,4-tetrahydroisoquinolin-4(R)-yl)phenyl]ureido}-acetate,
ethyl {3-[3-(6,8-dichloro-2-methyl-1,2,3,4-tetrahydroisoquinolin-4(S)-yl)phenyl]ureido}-acetate,
ethyl {3-[2-(6,8-dichloro-2-methyl-1,2,3,4-tetrahydroisoquinolin-4(R)-yl)phenyl]ureido}-acetate,
ethyl {3-[2-(6,8-dichloro-2-methyl-1,2,3,4-tetrahydroisoquinolin-4(S)-yl)phenyl]ureido}-acetate,
ethyl {3-[4-(6,8-dichloro-2-methyl-1,2,3,4-tetrahydroisoquinolin-4(R)-yl)phenyl]ureido}-acetate,
ethyl {3-[4-(6,8-dichloro-2-methyl-1,2,3,4-tetrahydroisoquinolin-4(S)-yl)phenyl]ureido)-acetate,
{3-[4-(6,8-dichloro-2-methyl-1,2,3,4-tetrahydroisoquinolin-4(R)-yl)phenyl]ureido}acetic acid,
{3-[4-(6,8-dichloro-2-methyl-1,2,3,4-tetrahydroisoquinolin-4(S)-yl)phenyl]ureido}acetic acid,
{3-[2-(6,8-dichloro-2-methyl-1,2,3,4-tetrahydroisoquinolin-4(R)-yl)phenyl]ureido}acetic acid,
{3-[2-(6,8-dichloro-2-methyl-1,2,3,4-tetrahydroisoquinolin-4(S)-yl)phenyl]ureido}acetic acid,
{3-[3-(6,8-dichloro-2-methyl-1,2,3,4-tetrahydroisoquinolin-4(R)-yl)phenyl]ureido}acetic acid,
{3-[3-(6,8-dichloro-2-methyl-1,2,3,4-tetrahydroisoquinolin-4(S)-yl)phenyl]ureido}acetic acid,
2-methoxyethyl [4-(6,8-dichloro-2-methyl-1,2,3,4-tetrahydroisoquinolin-4(R)-yl)phenyl]-carbamate,
2-methoxyethyl [4-(6,8-dichloro-2-methyl-1,2,3,4-tetrahydroisoquinolin-4(S)-yl)phenyl]-carbamate,
2-methoxyethyl [3-(6,8-dichloro-2-methyl-1,2,3,4-tetrahydroisoquinolin-4(R)-yl)phenyl]-carbamate,
and
2-methoxyethyl [3-(6,8-dichloro-2-methyl-1,2,3,4-tetrahydroisoquinolin-4(S)-yl)phenyl]-carbamate;

and their pharmaceutically acceptable salts and trifluoroacetates.

Very especially preferred are compounds of the formula I selected from the group of
N-[4-(6,8-dichloro-2-methyl-1,2,3,4-tetrahydroisoquinolin-4-yl)phenyl]-(2R,3S,4R,5R)-2,3,4,5,6-pentahydroxyhexanamide,
N-[3-(6,8-dichloro-2-methyl-1,2,3,4-tetrahydroisoquinolin-4-yl)phenyl]-(2R,3S,4R,5R)-2,3,4,5,6-pentahydroxyhexanamide,
N-[2-(6,8-dichloro-2-methyl-1,2,3,4-tetrahydroisoquinolin-4-yl)phenyl]-(2R,3S,4R,5R)-2,3,4,5,6-pentahydroxyhexanamide,
N-[3-((S)-6,8-dichloro-2-methyl-1,2,3,4-tetrahydroisoquinolin-4-yl)phenyl]-(2R,3S,4R,5R)-2,3,4,5,6-pentahydroxyhexanamide,
N-[3-((R)-6,8-dichloro-2-methyl-1,2,3,4-tetrahydroisoquinolin-4-yl)phenyl]-(2R,3S,4R,5R)-2,3,4,5,6-pentahydroxyhexanamide,
1-[3-(6,8-dichloro-2-methyl-1,2,3,4-tetrahydroisoquinolin-4-yl)phenyl]-3-(2-hydroxy-1-hydroxymethylethyl)urea,
1-[3-(6,8-dichloro-2-methyl-1,2,3,4-tetrahydroisoquinolin-4-yl)phenyl]-3-(2-hydroxy-1,1-bishydroxymethylethyl)urea,
1-[3-(6,8-dichloro-2-methyl-1,2,3,4-tetrahydroisoquinolin-4-yl)phenyl]-3-((2S,3R,4R,5R)-2,3,4,5,6-pentahydroxyhexyl)urea,
1-[3-(6,8-dichloro-2-methyl-1,2,3,4-tetrahydroisoquinolin-4-yl)phenyl]-3-((4R,5S,6R)-2,4,5-trihydroxy-6-hydroxymethyltetrahydropyran-3-yl)urea,
{N-[3-(6,8-dichloro-2-methyl-1,2,3,4-tetrahydroisoquinolin-4-yl)phenyl]-N'-(1-sulfo-2-ethyl)}urea,
{N-[3-(6,8-dichloro-2-methyl-1,2,3,4-tetrahydroisoquinolin-4-yl)phenyl]-N'-(ethyl-2-trimethylammonium)}urea chloride,
{N-[3-(6,8-dichloro-2-methyl-1,2,3,4-tetrahydroisoquinolin-4-yl)phenyl]-N'-(1-carboxy-3-hydroxy-2S-propyl)}urea,
{N-[3-(6,8-dichloro-2-methyl-1,2,3,4-tetrahydroisoquinolin-4-yl)phenyl]-N'-(1-carboxy-4-aminocarboxy-2S-butyl)}urea,
3-(6,8-dichloro-2-methyl-1,2,3,4-tetrahydroisoquinolin-4-yl)-N-((2S,3R,4R,5R)-2,3,4,5,6-pentahydroxyhexyl)benzamide,
3-(6,8-dichloro-2-methyl-1,2,3,4-tetrahydroisoquinolin-4-yl)-N-(2-hydroxy-1-hydroxymethylethyl)benzamide,
2-(S)-[3-(6,8-dichloro-2-methyl-1,2,3,4-tetrahydroisoquinolin-4-yl)benzoylamino]-3-hydroxypropionic acid,
2-(S)-[3-(6,8-dichloro-2-methyl-1,2,3,4-tetrahydroisoquinolin-4-yl)benzoylamino]succinic acid,
2-(S)-[3-(6,8-dichloro-2-methyl-1,2,3,4-tetrahydroisoquinolin-4-yl)benzoylamino]4-succinamic acid,
N-[3-(6,8-dichloro-2-methyl-1,2,3,4-tetrahydroisoquinolin-4-yl)phenyl]-N'-[1-carboxy-5-guanidino-2S-pentyl]urea,
{N-[3-(6,8-dichloro-2-methyl-1,2,3,4-tetrahydroisoquinolin-4-(R)-yl)phenyl]-N'-(1-carboxy-4-aminocarboxy-2S-butyl)}urea,
{N-[3-(6,8-dichloro-2-methyl-1,2,3,4-tetrahydroisoquinolin-4-(S)-yl)phenyl]-N'-(1-carboxy-4-aminocarboxy-2S-butyl)}urea,
{N-[3-(6,8-dichloro-2-methyl-1,2,3,4-tetrahydroisoquinolin-4-(R)-yl)phenyl]-N'-(-carboxy-3-hydroxy-2S-propyl)}urea,
{N-[3-(6,8-dichloro-2-methyl-1,2,3,4-tetrahydroisoquinolin-4-(S)-yl)phenyl]-N'-(1-carboxy-3-hydroxy-2S-propyl)}urea,
1-[3-(6,8-dichloro-2-methyl-1,2,3,4-tetrahydroisoquinolin-4-(R)-yl)phenyl]-3-(2-hydroxy-1,1-bishydroxymethylethyl)urea,
1-[3-(6,8-dichloro-2-methyl-1,2,3,4-tetrahydroisoquinolin-4-(S)-yl)phenyl]-3-(2-hydroxy-1,1-bishydroxymethylethyl)urea,
1-[3-((R)-6,8-dichloro-2-methyl-1,2,3,4-tetrahydroisoquinolin-4-yl)phenyl]-3-((2S,3R,4R,5R)-2,3,4,5,6-pentahydroxyhexyl)urea,
1-[3-((S)-6,8-dichloro-2-methyl-1,2,3,4-tetrahydroisoquinolin-4-yl)phenyl]-3-((2S,3R,4R,5R)-2,3,4,5,6-pentahydroxyhexyl)urea, 5-(6,8-dichloro-2-methyl-1,2,3,4-tetrahydroisoquinolin-4-yl)-N,N'-bis(2-hydroxy-1-hydroxymethylethyl)isophthalamide,
5-(6,8-dichloro-2-methyl-1,2,3,4-tetrahydroisoquinolin-4-yl)-N,N'-bis(2-hydroxy-1,1-bishydroxymethylethyl)isophthalamide,
5-(6,8-dichloro-2-methyl-1,2,3,4-tetrahydroisoquinolin-4-yl)-N-(2-hydroxy-1,1-bishydroxymethylethyl)isophthalamide,
5-(6,8-dichloro-2-methyl-1,2,3,4-tetrahydroisoquinolin-4-yl)-N,N'-bis((2S,3R,4R,5R)-2,3,4,5,6-pentahydroxyhexyl)isophthalamide,
5-(6,8-dichloro-2-methyl-1,2,3,4-tetrahydroisoquinolin-4-yl)-N-((2S,3R,4R,5R)-2,3,4,5,6-pentahydroxyhexyl)isophthalamide,
(S)-2-[3-((S)-1-carboxy-2-hydroxyethylcarbamoyl)-5-(6,8-dichloro-2-methyl-1,2,3,4-tetrahydroisoquinolin-4-yl)benzoylamino]-3-hydroxypropionic acid,
(S)-N-[3-(6,8-dichloro-2-methyl-1,2,3,4-tetrahydroisoquinolin-4-yl)phenyl]-2-amino-5-guanidinopentanamide,
(S)-N-[4-(6,8-dichloro-2-methyl-1,2,3,4-tetrahydroisoquinolin-4-yl)phenyl]-2-amino-5-guanidinopentanamide,
(S)-2-amino-N-[3-(6,8-dichloro-2-methyl-1,2,3,4-tetrahydroisoquinolin-4-yl)phenyl]-3-(1H-imidazol-4-yl)propionamide,
(S)-2-amino-N-[4-(6,8-dichloro-2-methyl-1,2,3,4-tetrahydroisoquinolin-4-yl)phenyl]-3-(1H-imidazol-4-yl)propionamide,
ethyl {3-[4-(6,8-dichloro-2-methyl-1,2,3,4-tetrahydroisoquinolin-4-yl)phenyl]ureido}-acetate,
ethyl {3-[3-(6,8-dichloro-2-methyl-1,2,3,4-tetrahydroisoquinolin-4-yl)phenyl]ureido}-acetate,
ethyl {3-[2-(6,8-dichloro-2-methyl-1,2,3,4-tetrahydroisoquinolin-4-yl)phenyl]ureido}-acetate,
{3-[3-(6,8-dichloro-2-methyl-1,2,3,4-tetrahydroisoquinolin-4-yl)phenyl]ureido}acetic acid,
{3-[4-(6,8-dichloro-2-methyl-1,2,3,4-tetrahydroisoquinolin-4-yl)phenyl]ureido}acetic acid,
{3-[2-(6,8-dichloro-2-methyl-1,2,3,4-tetrahydroisoquinolin-4-yl)phenyl]ureido}acetic acid,
ethyl {3-[3-(6,8-dichloro-2-methyl-1,2,3,4-tetrahydroisoquinolin-4(R)-yl)phenyl]ureido}-acetate,
ethyl {3-[3-(6,8-dichloro-2-methyl-1,2,3,4-tetrahydroisoquinolin-4(S)-yl)phenyl]ureido}-acetate,
ethyl {3-[2-(6,8-dichloro-2-methyl-1,2,3,4-tetrahydroisoquinolin-4(R)-yl)phenyl]ureido}-acetate,
ethyl {3-[2-(6,8-dichloro-2-methyl-1,2,3,4-tetrahydroisoquinolin-4(S)-yl)phenyl]ureido}-acetate,
ethyl {3-[4-(6,8-dichloro-2-methyl-1,2,3,4-tetrahydroisoquinolin-4(R)-yl)phenyl]ureido}-acetate,
ethyl {3-[4-(6,8-dichloro-2-methyl-1,2,3,4-tetrahydroisoquinolin-4(S)-yl)phenyl]ureido}-acetate,
{3-[4-(6,8-dichloro-2-methyl-1,2,3,4-tetrahydroisoquinolin-4(R)-yl)phenyl]ureido}acetic acid,
{3-[4-(6,8-dichloro-2-methyl-1,2,3,4-tetrahydroisoquinolin-4(S)-yl)phenyl]ureido}acetic acid,
{3-[2-(6,8-dichloro-2-methyl-1,2,3,4-tetrahydroisoquinolin-4(R)-yl)phenyl]ureido}acetic acid,
{3-[2-(6,8-dichloro-2-methyl-1,2,3,4-tetrahydroisoquinolin-4(S)-yl)phenyl]ureido}acetic acid,
{3-[3-(6,8-dichloro-2-methyl-1,2,3,4-tetrahydroisoquinolin-4(R)-yl)phenyl]ureido}acetic acid,
{3-[3-(6,8-dichloro-2-methyl-1,2,3,4-tetrahydroisoquinolin-4(S)-yl)phenyl]ureido}acetic acid,
2-methoxyethyl [4-(6,8-dichloro-2-methyl-1,2,3,4-tetrahydroisoquinolin-4(R)-yl)phenyl]-carbamate,
2-methoxyethyl [4-(6,8-dichloro-2-methyl-1,2,3,4-tetrahydroisoquinolin-4(S)-yl)phenyl]-carbamate,
2-methoxyethyl [3-(6,8-dichloro-2-methyl-1,2,3,4-tetrahydroisoquinolin-4(R)-yl)phenyl]-carbamate and 2-methoxyethyl [3-(6,8-dichloro-2-methyl-1,2,3,4-tetrahydroisoquinolin-4(S)-yl)phenyl]-carbamate;

and their pharmaceutically acceptable salts and trifluoroacetates.

The groups of the form $C_a(OR32)_xH_{2a+1-x}$ described under G may be either straight-chain or branched. This results in polyhydroxylated alkyl chains, as derived, for example, from monosaccharide building blocks, which are bonded to the phenyl radical via a linker unit L. Correspondingly, the formula $C_b(OR32)_yH_{2b-1-y}$ preferably describes polyhydroxylated, cyclic alkyl substituents. Exchange of a $CH_2$ unit for O results, for example, in the class of the pyranoside or furanoside carbohydrate building blocks, as realized in example 9. G may equally derive from the group of the amino acids, which are bonded via the amino acid amino or amino acid carboxyl function, in which case the amino or carbonyl function is included in the linker unit L. The amino acid side chains then occur in R38.

When the compounds of the formula I contain one or more centers of asymmetry, these may each independently have either the S or R configuration. The compounds may be present as optical isomers, as enantiomers, as diastereomers, as racemates or as mixtures in any ratios thereof.

The present invention includes all tautomeric forms of the compounds of the formula I.

Alkyl radicals may be straight-chain or branched. This also holds when they bear substituents or occur as substituents of other radicals, for example in fluoroalkyl radicals or alkoxy radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), n-pentyl, isopentyl, tert-pentyl, neopentyl, hexyl, heptyl, octyl. Preferred alkyl radicals are methyl, ethyl, n-propyl, isopropyl, n-butyl, tert-butyl, n-pentyl, n-hexyl. In the alkyl radicals, one or more, for example 1, 2, 3, 4, 5, 6, 7, 8, 9, 10, 11, 12, 13, 14, 15, 16 or 17, hydrogen atoms may be substituted by fluorine atoms. Examples of such fluoroalkyl radicals are trifluoromethyl, 2,2,2-trifluoroethyl, pentafluoroethyl, heptafluoroisopropyl. Substituted alkyl radicals may be substituted in any desired positions, for example by hydroxyl. In the alkyl radicals, one or more $CH_2$ groups may be replaced by O, NH or N-alkyl.

Alkenyl radicals may be straight-chain or branched. This also holds when they bear substituents, for example in fluoroalkenyl radicals. The alkenyl radicals may be unsaturated in different positions. Examples of alkenyl radicals are propenyl, butenyl, pentenyl, hexenyl or heptenyl. In alkenyl radicals, one or more, for example 1, 2, 3, 4, 5, 6, 7, 8, 9, 10, 11, 12 or 13, hydrogen atoms may be substituted by fluorine atoms. Substituted alkenyl radicals may be substituted in any desired positions, for example by hydroxyl. In the alkenyl radicals, one or more $CH_2$ groups may be replaced by O, NH or N-alkyl.

Acyl radicals may be straight-chain or branched. This is also true when they bear substituents. Examples of acyl radicals are formyl, acetyl, propionyl or butyryl. In acyl radicals, one or more, for example 1, 2, 3, 4, 5, 6 or 7, hydrogen atoms may be substituted by fluorine atoms.

Examples of cycloalkyl radicals are cyclopropyl, cyclobutyl, cyclopentyl, cyclohexyl, cycloheptyl or cyclooctyl. In cycloalkyl radicals, one or more, for example 1, 2, 3, 4, 5, 6, 7, 8, 9, 10, 11, 12 or 13, hydrogen atoms may be substituted by fluorine atoms. Substituted cycloalkyl radicals may be substituted in any desired positions, for example by hydroxyl. The cycloalkyl radicals may also be in branched form as alkylcycloalkyl or cycloalkylalkyl, for example methylcyclohexyl or cyclohexylmethyl. In the cycloalkyl radicals, one or more $CH_2$ groups may be replaced by O, NH or N-alkyl.

Phenyl radicals may be unsubstituted or singly or multiply, for example singly, doubly or triply, substituted by identical or different radicals. When a phenyl radical is substituted, it preferably bears one or two identical or different substituents. This applies equally to substituted phenyl radicals in groups such as phenylalkyl, phenylcarbonyl, etc. Phenylalkyl radicals are, for example, benzyl, 1-phenylethyl or 2-phenylethyl. In monosubstituted phenyl radicals, the substituent may be in the 2-position, the 3-position or the 4-position. Disubstituted phenyl may be substituted in the 2,3-position, 2,4-position, 2,5-position, 2,6-position, 3,4-position or 3,5-position. In trisubstituted phenyl radicals, the substituents may be in the 2,3,4-position, 2,3,5-position, 2,4,5-position, 2,4,6-position, 2,3,6-position or 3,4,5-position.

Heteroaryl radicals are aromatic ring compounds in which one or more ring atoms are oxygen atoms, sulfur atoms or nitrogen atoms, for example 1, 2, 3 or 4 nitrogen atoms, 1 or 2 oxygen atoms, 1 or 2 sulfur atoms or are combinations of different heteroatoms.

The heteroaryl radicals may be bonded via all positions, for example via the 1-position, 2-position, 3-position, 4-position, 5-position, 6-position, 7-position or 8-position. Heteroaryl radicals may be unsubstituted or singly or multiply, for example singly, doubly or triply, substituted by identical or different radicals. Heteroaryls are, for example, 2- or 3-thienyl, 2- or 3-furyl, 1-, 2- or 3-pyrrolyl, 1-, 2-, 4- or 5-imidazolyl, 1-, 3-, 4- or 5-pyrazolyl, 1,2,3-triazol-1-, -4- or -5-yl, 1,2,4-triazol-1-, -3- or -5-yl, 1- or 5-tetrazolyl, 2-, 4- or 5-oxazolyl, 3-, 4- or 5-isoxazolyl, 1,2,3-oxadiazol-4- or -5-yl, 1,2,4,-oxadiazol-3- or -5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3- or -5-yl, 1,2,3-thiadiazol-4- or -5-yl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3, 5-, 6-, 7- or 8-quinoxalinyl, 1-, 4-, 5-, 6-, 7- or 8-phthalazinyl. Also included are the corresponding N-oxides of these compounds, i.e., for example, 1-oxy-2-, 3- or 4-pyridyl. Preference is given to the 5- or 6-membered heterocycles, for example imidazolyl, pyrazolyl, pyrrolyl, triazolyl, tetrazolyl, thiazolyl and oxazolyl and pyridyl.

Also included as $CH_2$ units are the $CH_3$ groups which terminate an alkyl chain, which are interpreted in this context as $CH_2$—H groups.

DETAILED DESCRIPTION OF THE INVENTION

Methods for preparing the compounds of the formula I are described in the following. The compounds of the formula I described here can be prepared starting from the benzylamine precursors IV. If not commercially obtainable, these can in turn be synthesized by standard methods known to those skilled in the art from the corresponding benzyl chlorides or bromides III and the corresponding amine.

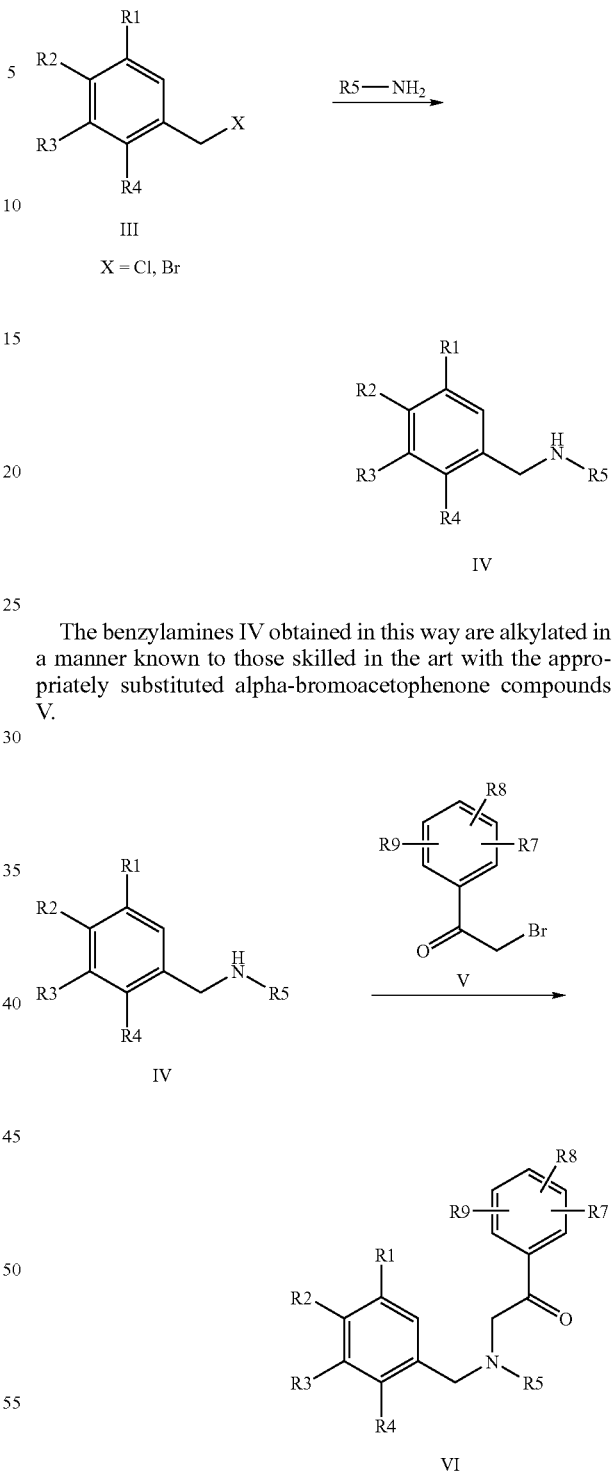

The benzylamines IV obtained in this way are alkylated in a manner known to those skilled in the art with the appropriately substituted alpha-bromoacetophenone compounds V.

The alpha-bromoacetophenone compounds V can be obtained in literature methods from the corresponding acetophenone precursors by bromination.

By reduction of the carbonyl groups in VI and subsequent acid-catalyzed cyclization of the resulting alcohols VII (cf. Tetrahedron Lett.; 1989, 30, 5837; Org. Prep. Proced. Int.; 1995, 27, 513) the desired tetrahydroisoquinolines I can be obtained by known methods.

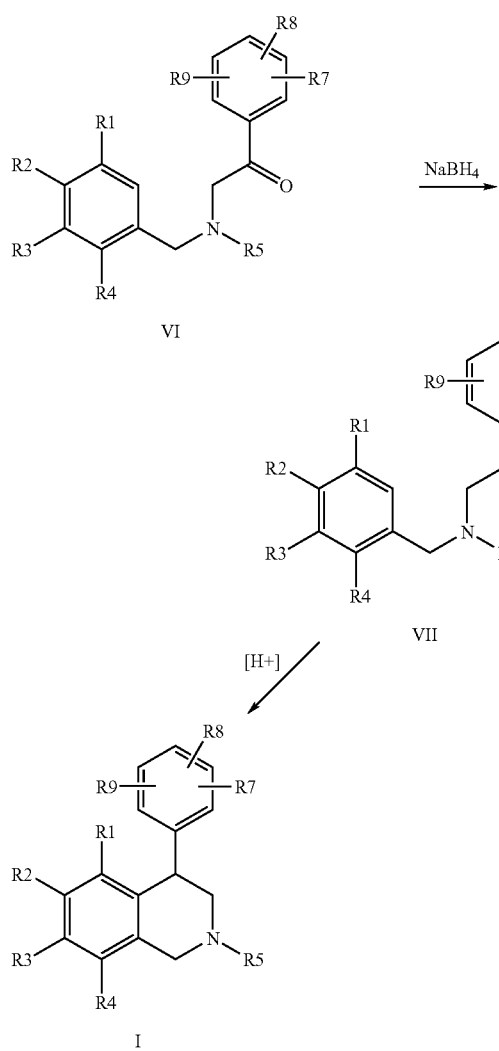

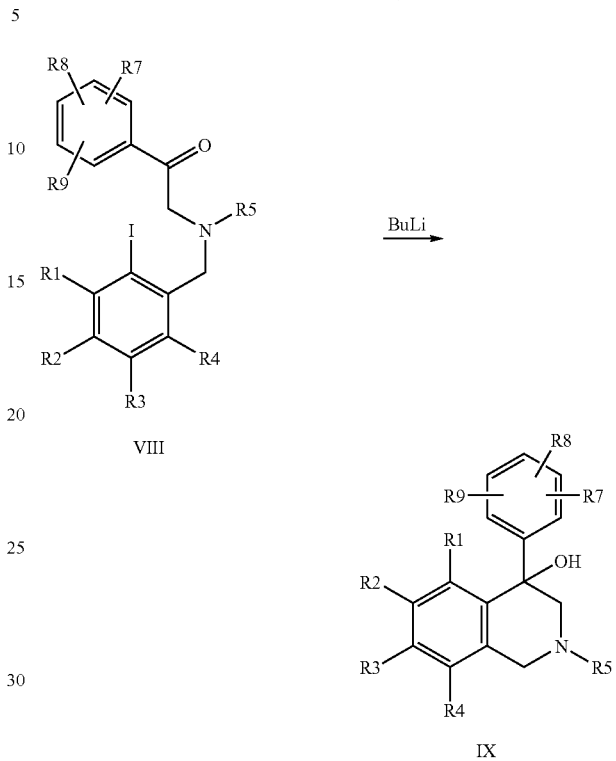

Chem. Pharm. Bull.; 1994, 42, 67) by halogen-metal exchange and subsequent nucleophilic attack of the intermediate organolithium species on the carbonyl group (cf. Chem. Pharm. Bull.; 1995, 43, 1543).

The tertiary alcohols IX synthesized in this way can be converted by known methods to further derivatives, for example the ethers or esters derived therefrom.

To prepare alkyl-branched analogs (I), the appropriate diphenylacetic esters X can be alkylated in the alpha-position with R6 by known methods. The desired products XI can be converted by standard methods to the corresponding amides XII which are converted to the desired tetrahydroisoquinolines I in a Pictet-Spengler-like reaction (cf. Tetrahedron; 1987, 43, 439; Chem. Pharm. Bull.; 1985, 33, 340).

When R6 is not H, the desired compounds of the formula I can be prepared, for example, from the iodides VIII (cf.

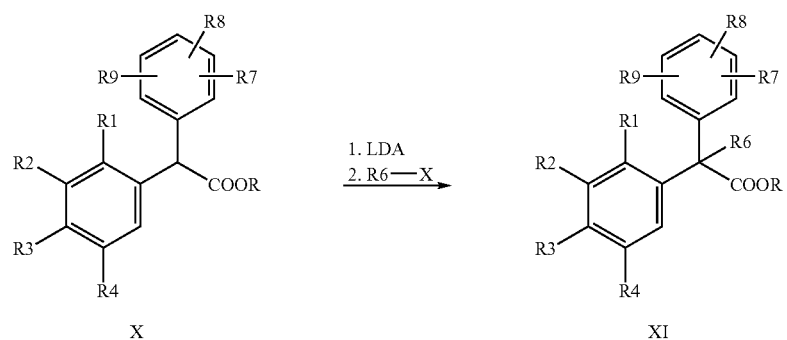

-continued

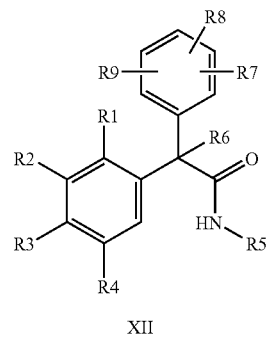
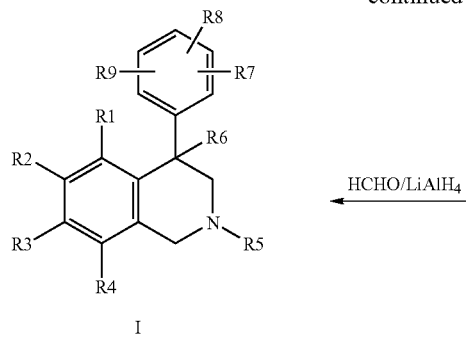

The bonding of the L-G substituents to the R7, R8 or R9 positions may, for example, be via an amide bond. In this case, the above-described synthetic routes ensure that at least one of the R7, R8 or R9 radicals is present as an $NH_2$ or COOH group. A polar radical can be bonded in a manner known to those skilled in the art by coupling polar carboxylic acids (for example gluconic acid which has to be appropriately protected) to the $NH_2$ compound XIII or by coupling polar amines (for example glucamine) to the corresponding —COOH compound XIV, resulting in the carboxanilides Ia or the carboxamides Ib.

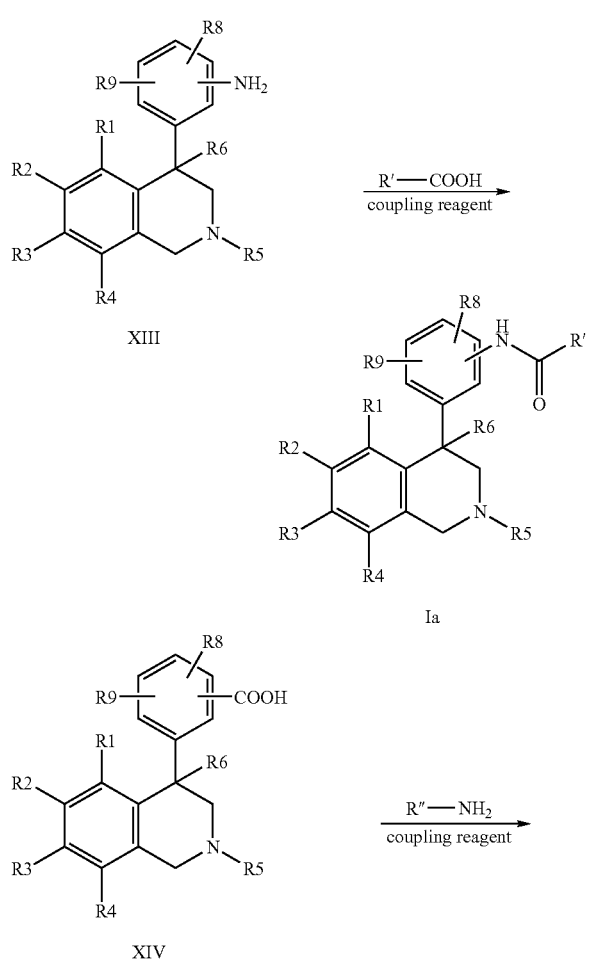

-continued

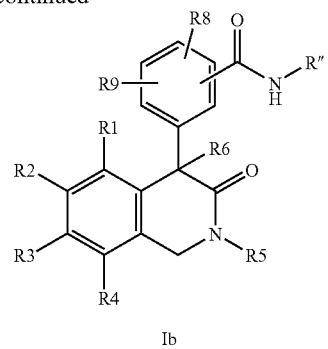

In the compounds of the formulae II to XIV, the R1 to R9 radicals are each as defined above or they are functional groups in protected form or in precursor stages.

The urea or else thiourea compounds derived from the precursor molecules XIII can likewise be prepared therefrom in a manner known to those skilled in the art.

It has been possible to show that compounds of the formula I constitute outstanding inhibitors of the sodium-hydrogen exchanger (NHE), especially of the sodium-hydrogen exchanger of the subtype 3 (NHE3).

Tetrahydroisoquinolines as inhibitors of the sodium-hydrogen exchanger of the subtype 3 (NHE3) have already been described in the patent application WO03048129. The patent application WO03055880 describes the related compound class of the tetrahydroisoquinolinium salts as NHE3 inhibitors. However, the properties of these compounds are not yet satisfactory in various respects, and there is still a need for compounds having a more favorable pharmacodynamic or pharmacokinetic property profile, and suitable for treating highly differing disorders.

The NHE3 is found in the body of various species, preferably in the gallbladder, the intestines and in the kidneys (Larry Fliegel et al., Biochem. Cell. Biol. 76: 735-741, 1998), but could also be found in the brain (E. Ma et al., Neuroscience 79: 591-603).

As a consequence of their unexpected NHE-inhibitory properties, the compounds of the formula I are suitable for preventing and treating disorders which are caused by activation and/or by an activated NHE. The use of the inventive compounds relates to the prevention and treatment of acute and chronic disorders in veterinary medicine and human medicine.

Thus, the inventive inhibitors of NHE are suitable for treating disorders which are caused by ischemia and/or by reperfusion.

As a consequence of their pharmacological properties, the compounds described here are outstandingly suitable as antiarrhythmic medicaments having a cardioprotective component for prophylaxis of infarction and for treatment of infarction, and also for treatment of angina pectoris, in which case they also inhibit or greatly reduce, in a preventative manner, the pathophysiological events in the development of ischemia-induced damage, in particular in the induction of ischemia-induced cardiac arrhythmias. Owing to their protective effects against pathological hypoxic and ischemic situations, the compounds of the formula I used in accordance with the invention can, as a consequence of inhibition of the cellular $Na^+/H^+$ exchange mechanism, be used as a medicament for treating all acute or chronic damage induced by ischemia or disorders induced primarily or secondarily thereby. This relates to the use thereof as medicaments for surgical interventions, for example in organ transplants, in which case the compounds can be used both for the protection of the organs in the donor and during the removal, to protect removed organs, for example in the course of treatment with or storage thereof in physiological bath fluids, and also in the course of transfer into the recipient organism. The compounds are likewise valuable medicaments having a protective action when carrying out angioplastic surgical interventions, for example on the heart or else on peripheral vessels.

In accordance with their protective action against ischemia-induced damage, the compounds are also suitable as medicaments for treating ischemias of the nervous system, especially of the CNS, in which case they are suitable, for example, for treating stroke or cerebral edema.

In addition, the compounds of the formula I used in accordance with the invention are likewise suitable for treating forms of shock, for example allergic, cardiogenic, hypovolemic and bacterial shock.

In addition, the compounds induce an improvement in the respiratory drive and are therefore used for treating respiratory conditions in the event of the following clinical conditions and disorders: disrupted central respiratory drive (for example central sleep apneas, sudden infant death, postoperative hypoxia), muscle-related respiratory disorders, breathing disorders after long-term ventilation, breathing disorders in the course of adaptation in high mountains, obstructive and mixed form of sleep apneas, acute and chronic pulmonary disorders with hypoxia and hypercapnia.

The compounds additionally increase the muscle tone of the upper airways, so that snoring is suppressed.

The compounds mentioned are therefore advantageously used to prepare a medicament for the prevention and treatment of sleep apneas and muscle-related respiratory disorders and to prepare a medicament for the prevention and treatment of snoring.

A combination of an NHE inhibitor with a carbonic anhydrase inhibitor (for example acetazolamide), in which case the latter brings about metabolic acidosis and thus itself increases respiratory activity, is found to be advantageous as a result of enhanced action and reduced use of active ingredient.

In addition, the compounds described here are suitable as medicaments for therapy and prophylaxis of diseases and disorders which are induced by hyperexcitability of the central nervous system, in particular for treating diseases of the epileptic type, centrally induced clonic and tonic spasms, states of psychological depression, anxiety disorders and psychoses. The NHE inhibitors described here may be employed alone or in combination with other antiepileptic substances or antipsychotic active ingredients, or carbonate dehydratase inhibitors, for example with acetazolamide, and also with further inhibitors of NHE or of the sodium-dependent chloride-bicarbonate exchanger (NCBE).

It has been found that the compounds used in accordance with the invention have a mild laxative effect and can accordingly be used advantageously as laxatives or in the event of risk of constipation.

In addition, the inventive compounds can advantageously be used for the prevention and therapy of acute and chronic disorders of the intestinal tract which are induced by ischemic states in the intestinal region and/or by subsequent reperfusion. Such complications may be caused, for example, by inadequate bowel peristalsis as frequently observed, for example, after surgical interventions, in the event of constipation or greatly reduced bowel activity.

There is also the possibility of preventing gallstone formation.

In addition, the compounds of the formula I used in accordance with the invention feature strong inhibiting action on the proliferation of cells, for example on fibroblast cell proliferation and the proliferation of smooth vascular muscle cells. The compounds of the formula I are therefore useful as valuable therapeutic agents for disorders in which cell proliferation constitutes a primary or secondary cause, and can therefore be used as antiatherosclerotic agents, agents against diabetic late complications, agents against chronic kidney failure, cancers, fibrotic disorders of the heart and also as pulmonary fibrosis, hepatic fibrosis, or renal fibrosis, organ hypertrophies and hyperplasias, for example of the heart and the prostate, and thus for the prevention and treatment of congestive heart failure or in the event of prostate hyperplasia or prostate hypertrophy.

The inventive compounds are effective inhibitors of the cellular sodium-proton antiporter (Na/H exchanger) which is elevated in numerous disorders (essential hypertension, atherosclerosis, diabetes, etc.), also in those cells which are readily amenable to measurements, for example in erythrocytes, thrombocytes or leucocytes. The compounds used in accordance with the invention are therefore suitable as outstanding and simple scientific tools, for example in their use as diagnostic agents for determining and differentiating different forms of hypertension, but also of atherosclerosis, diabetes and diabetic late complications, proliferative disorders, etc.

In addition, the compounds of the formula I are suitable for preventive therapy for preventing development of, and treating, high blood pressure, for example of essential hypertension, since they reduce or fully inhibit the reabsorption of NaCl in the tubular system of the kidneys. Accordingly, they are also outstandingly suitable as combination and formulation partners for medicaments which are used to treat high blood pressure. For example, they may be combined with diuretics having thiazide-like action, loop diuretics, aldosterone and pseudoaldosterone antagonists such as hydrochlorothiazide, indapamide, polythiazide, furosemide, piretanide, torasemide, bumetanide, amiloride, triamterene. In addition, the NHE inhibitors of the present invention may be used in combination with ACE inhibitors, for example ramipril, enalapril or captopril. Further favorable combination partners are also β-blockers. The NHE inhibitors described may likewise be used in the prevention of, and for treating, thrombotic disorders, since, as NHE inhibitors, they can both inhibit platelet aggregation itself and additionally inhibit or prevent the excessive release of coagulation mediators, in particular of von Willebrand's factor. The NHE inhibitors of the present invention can therefore be combined with further anticoagulant active ingredients, for example acetylsalicylic acid, thrombin antagonists, factor Xa antagonists, medicaments having fibrinolytic action, factor VIIa antagonists, etc. Combined application of the present NHE inhibitors with NCBE inhibitors is particularly beneficial.

It has also been found that NHE inhibitors exhibit a beneficial influence on serum lipoproteins. It is generally acknowledged that excessively high blood lipid levels, known as hyperlipoproteinemias, constitute a significant risk factor for the development of arteriosclerotic vascular lesions, especially of coronary heart disease. The reduction in elevated serum lipoproteins is therefore exceptionally important for the prophylaxis and the regression of atherosclerotic lesions. The compounds used in accordance with the invention can therefore be used for prophylaxis and for regression of atherosclerotic lesions by eliminating a causal risk factor. The inventive inhibitors of NHE can also advantageously be combined with other antiarteriosclerotic active ingredients, such as a substance from the class of the fibrates, an upregulator of LD2 receptor activity, such as MD-700 and LY295427, or a cholesterol or bile acid resorption inhibitor or an antihypercholesterolemic from the class of the statins, such as, for example, pravastatin, lovastatin, simvastatin. This protection of the vessels against the syndrome of endothelial dysfunction makes compounds of the formula I viable medicaments for preventing and for treating coronary vasospasms, peripheral vascular disorders, such as claudicatio intermittens, atherogenesis and atherosclerosis, left-ventricular hypertrophy and dilated cardiomyopathy, and thrombotic disorders.

The compounds mentioned may likewise be used for treating diseases which are caused by protozoa and are especially suitable as antimalarials.

In addition, the compounds are suitable for controlling sucking parasites such as mosquitoes, ticks, fleas and plant pests.

In accordance with their protective actions, the compounds are also suitable as medicaments for maintaining health and prolonging life.

Generally, the NHE inhibitors described here may advantageously be combined with other compounds which regulate the intracellular pH, and useful combination partners are inhibitors of the enzyme group of carbonate dehydratase, inhibitors of bicarbonate ion-transporting systems such as the sodium-bicarbonate cotransporter or the sodium-dependent chloride-bicarbonate exchanger, and also other NHE inhibitors, for example having inhibitory action on other NHE subtypes, because they may strengthen the pharmacologically relevant pH-regulating effects of the NHE inhibitors described here. The compounds mentioned therefore advantageously find use for preparing a medicament for preventing and treating sleep apneas and muscle-related respiratory disorders; for preparing a medicament for preventing and treating snoring; for preparing a medicament for blood pressure reduction; for preparing a medicament having a laxative effect for preventing and treating intestinal blockages; for preparing a medicament for preventing and treating disorders which are induced by ischemia and reperfusion of central and peripheral organs such as acute renal failure, stroke, endogenous states of shock, intestinal disorders, etc.; for preparing a medicament for treating diabetic late damage and chronic renal disorders, in particular all renal inflammations (nephritides) which are associated with increased protein/albumin excretion; for preparing a medicament for treating hypercholesterinemia; for preparing a medicament for preventing atherogenesis and atherosclerosis; for preparing a medicament for preventing and treating disorders which are induced by elevated cholesterol levels; for preparing a medicament for preventing and treating disorders which are induced by endothelial dysfunction; for preparing a medicament for treating infection by ectoparasites; for preparing a medicament for treating the diseases mentioned in combinations with blood pressure-reducing substances, preferably with angiotensin converting enzyme (ACE) inhibitors, with diuretics, aldosterone antagonists or angiotensin receptor antagonists. It has been found that a combination of an NHE inhibitor of the formula I with a blood lipid level-reducing active ingredient, preferably with an HMG-CoA reductase inhibitor (for example lovastatin or pravastatin), the latter bringing about hypolipidemic action and thus increasing the hypolipidemic properties of the NHE inhibitor of the formula I, is a beneficial combination having enhanced action and reduced use of active ingredient.

The administration of sodium-proton exchange inhibitors of the formula I as novel medicaments for reducing elevated blood lipid level is claimed, as is the combination of sodium-proton exchange inhibitors with blood pressure-reducing and/or hypolipidemic medicaments.

The invention also relates to pharmaceutical compositions for human, veterinary or phytoprotective use, comprising an effective amount of a compound of the formula I and/or of a pharmaceutically acceptable salt thereof, as well as curative compositions for human, veterinary or phytoprotective use, comprising an effective amount of a compound of the formula I and/or of a pharmaceutically acceptable salt thereof alone or in combination with one or more other pharmacological active ingredients or medicaments.

Medicaments which comprise a compound of the formula I or the pharmaceutically acceptable salts thereof can be administered, for example, orally, parenterally, intramuscularly, intravenously, rectally, nasally, by inhalation, subcutaneously or by a suitable transcutaneous dosage form, the preferred administration depending on the particular characteristics of the disorder. The compounds of the formula I can be used alone or together with pharmaceutical excipients, in veterinary or in human medicine and in plant protection. The medicaments comprise active ingredients of the formula I and/or their pharmaceutically acceptable salts in general in an amount of from 0.01 mg to 1 g per dose unit.

The excipients which are suitable for the desired pharmaceutical formulation are familiar to those skilled in the art on the basis of their expert knowledge. In addition to solvents, gel formers, suppository bases, tablet excipients and other active ingredient carriers, it is possible to use, for example, antioxidants, dispersants, emulsifiers, antifoams, flavorings, preservatives, solubilizers or colorings.

For an oral administration form, the active compounds are mixed with the additives suitable for this purpose, such as carriers, stabilizers or inert diluents and converted by customary methods to the suitable dosage forms, such as tablets, coated tablets, hard gelatin capsules, aqueous, alcoholic or oily solutions. Examples of useful inert carriers include gum arabic, magnesia, magnesium carbonate, potassium phosphate, lactose, glucose or starch, in particular corn starch. The preparation may be either in the form of dry granules or in the form of moist granules. Examples of useful oily carriers or useful solvents are vegetable or animal oils, such as sunflower oil or cod liver oil.

For subcutaneous, percutaneous or intravenous administration, the active compounds used, if desired with the substances customary for this purpose such as solubilizers, emulsifiers or further excipients are converted to solution, suspension or emulsion. Examples of useful solvents are: water, physiological saline or alcohols, for example ethanol, propanol, glycerol and additionally also sugar solutions such as glucose or mannitol solutions, or else a mixture of the different solvents mentioned.

Examples of suitable pharmaceutical formulations for administration in the form of aerosols or sprays are solutions, suspensions or emulsions of the active ingredient of the formula I in a pharmaceutically acceptable solvent, in particular ethanol or water, or a mixture of such solvents. If required, the formulation may also comprise other pharmaceutical excipients such as surfactants, emulsifiers and stabilizers, and also a propellant gas. Such a preparation typically contains the active ingredient in a concentration of from about 0.1 to 10% by weight, in particular from about 0.3 to 3% by weight.

The dosage of the active ingredient of the formula I to be administered and the frequency of administration depend on the potency and duration of action of the compounds used; additionally also on the nature and severity of the disease to be treated, and also on the gender, age, weight and individual responsiveness of the mammal to be treated.

On average, the daily dose of a compound of the formula I in the case of a patient weighing about 75 kg is at least 0.001 mg/kg, preferably 0.1 mg/kg, up to at most 30 mg/kg, preferably 1 mg/kg, of body weight. In the event of acute episodes of the disease, for instance immediately after suffering apnetic states in high mountains, even higher dosages may be necessary. Especially in the case of i.v. administration, for instance in a heart attack patient in the intensive care unit, up to 300 mg/kg per day may be necessary. The daily dose can be divided into one or more, for example up to 4, individual doses.

When the compounds of the formula I contain one or more acidic or basic groups and/or one or more basic heterocycles, the corresponding physiologically or toxicologically acceptable salts are also included in the invention, in particular the salts which can be used pharmaceutically. For instance, the compounds of the formula I can be deprotonated at an acidic group and be used, for example, as alkali metal salts, preferably sodium or potassium salts, or as ammonium salts, for example as salts with ammonia or organic amines or amino acids. Compounds of the formula I which contain a basic group can also be used in the form of their physiologically acceptable acid addition salts with inorganic or organic acids, for example as hydrochlorides, phosphates, sulfates, methanesulfonates, acetates, lactates, maleates, fumarates, malates, gluconates, etc.

EXPERIMENTAL DESCRIPTION AND EXAMPLES

List of Abbreviations Used:
$R_t$ Retention time
TFA Trifluoroacetic acid
HPLC High Performance Liquid Chromatography
eq equivalents
LCMS Liquid Chromatography Mass Spectroscopy
MS Mass Spectroscopy
ESI Electrospray ionization
RT Room temperature
THF Tetrahydrofuran
TOTU O-[(Ethoxycarbonyl)cyanomethyleneamino]-N,N,N',N'-tetramethyluronium tetrafluoroborate
DMSO Dimethyl sulfoxide
abs. absolute
decomp. decomposition
DMF Dimethylformamide
DMAP 4-Dimethylaminopyridine
HOBt 1-Hydroxybenzotriazole
DIC Diisopropylcarbodiimide
ACN Acetonitrile
DEA Diethylamine Example 1

N-[4-(6,8-dichloro-2-methyl-1,2,3,4-tetrahydroisoquinolin-4-yl)phenyl]-(2R,3S,4R,5R)-2,3,4,5,6-pentahydroxyhexanamide

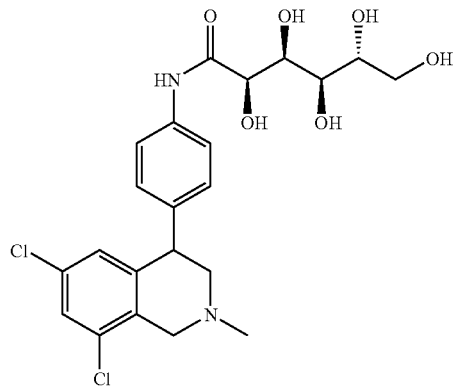

Intermediate 1: 2,4-dichlorobenzylmethylamine
was prepared by literature methods (J. Med. Chem.; 1984, 27, 1111)

Intermediate 2: N-[4-(2-bromoacetyl)phenyl]acetamide
was synthesized in a manner known to those skilled in the art by brominating N-(4-acetylphenyl)acetamide The starting compound (0.256 mol) is initially charged in 300 ml of acetic acid and a solution of 39.9 g of bromine (1.0 eq) in 60 ml of acetic acid was added dropwise at 60° C. After 1.5 hours, the mixture was cooled to room temperature and the reaction mixture was added to 1 l of ice-water. The precipitate was filtered off with suction, washed with water and dried to isolate 60 g of the title compound (m.p.: 192° C.).

Intermediate 3: N-{4-[2-(2,4-dichlorobenzylamino)acetyl]phenyl}acetamide
37.1 g (0.195 mol) of intermediate 1 were initially charged in 400 ml of dioxane and admixed with a solution of 60 g (0.234 mol) of intermediate 2 in 600 ml of dioxane. 134 ml of triethylamine were added and the mixture was stirred at room temperature for 4 h. After standing overnight, the precipitate was filtered off and the filtrate concentrated in vacuo. The residue was taken up in ethyl acetate, washed with NaHCO$_3$ and H$_2$O, dried with MgSO$_4$ and concentrated. The resulting oily residue was triturated with an ethyl acetate/ether mixture to obtain 36 g of intermediate 3 in the form of a crystalline solid (m.p.: 115-117° C.).

Intermediate 4: N-{4-[2-(2,4-dichlorobenzylamino)-1-hydroxyethyl]phenyl}acetamide
36 g (0.099 mol) of intermediate 3 were dissolved in 500 ml of methanol and admixed at 0° C. with 7.8 g (2 eq) of sodium borohydride. The mixture was stirred at 0° C. for another 30 min and at room temperature for a further hour. For workup, the reaction mixture was concentrated and the residue partitioned between 1 N HCl and ethyl acetate. The aqueous phase was removed, adjusted to pH 9 and extracted twice with ethyl acetate. The combined organic phases were dried with MgSO₄ and concentrated. The crude product obtained in this way could be used further without further purification.

Intermediate 5: N-[4-(6,8-dichloro-2-methyl-1,2,3,4-tetrahydroisoquinolin-4-yl)phenyl]acetamide 20 g (0.054 mol) of intermediate 4 were dissolved in 250 ml of dichloromethane and admixed dropwise at 0° C. with 250 ml of conc. H₂SO₄. The mixture was stirred at 0° C. for 2 h and at room temperature for 1 h. For workup, the reaction mixture was added to ice-water and the precipitate was filtered off with suction. The precipitate was taken up in 300 ml of 1 N NaOH and extracted 3 times with ethyl acetate. Drying of the organic phases and concentration afforded a crude product which was triturated with diisopropyl ether to isolate 11.7 g of the title compound as a crystalline solid (m.p.: 205-206° C.).

Intermediate 6: 4-(6,8-dichloro-2-methyl-1,2,3,4-tetrahydroisoquinolin-4-yl)phenylamine 3.0 g (8.6 mmol) of N-[4-(6,8-dichloro-2-methyl-1,2,3,4-tetrahydroisoquinolin-4-yl)phenyl]acetamide (intermediate 5) were dissolved in 100 ml of 20% sodium ethoxide solution and heated to reflux for 4 hours. A further 2.0 g (29.4 mmol) of solid sodium ethoxide were added and the mixture was heated to reflux for another 3 hours. For workup, the solvent was removed in vacuo, and the residue was taken up in 200 ml of H₂O and extracted twice with dichloromethane. The combined organic phases were dried with MgSO₄ and concentrated. For further purification, chromatography was effected on silica gel (1:1 ethyl acetate/heptane) to obtain the aniline as a yellowish oil in quantitative yield.

Intermediate 7: 2,3,4,5,6-penta-O-acetylgluconyl chloride

The title compound was synthesized by literature methods (Org. Syntheses, 1961, 41, 79-82).

Intermediate 8: N-[4-(6,8-dichloro-2-methyl-1,2,3,4-tetrahydroisoquinolin-4-yl)phenyl]-(2R,3S,4R,5R)-2,3,4,5,6-penta-O-acetylhexanamide 614 mg (2.0 mmol) of 4-(6,8-dichloro-2-methyl-1,2,3,4-tetrahydroisoquinolin-4-yl)phenylamine (intermediate 6) were initially charged in 20 ml of pyridine and admixed at 0° C. with a solution of 1.28 g (3.0 mmol) of 2,3,4,5,6-penta-O-acetylgluconyl chloride in 10 ml of dichloromethane. The mixture was stirred at 0° C. for 15 minutes and at room temperature for 1 hour. For workup, the mixture was concentrated and the residue taken up in dichloromethane. Washing was effected once with H₂O, once with saturated NaHCO₃ solution, twice with 1 N HCl and once more with H₂O, followed by drying over MgSO₄ and concentration. The crude product obtained in this way (1.12 g) could be used in the next reaction without further purification.

1: N-[4-(6,8-dichloro-2-methyl-1,2,3,4-tetrahydroisoquinolin-4-yl)phenyl]-(2R,3S,4R,5R)-2,3,4,5,6-pentahydroxyhexanamide;

The crude product obtained in intermediate 8 was dissolved in 30 ml of methanol and admixed in portions at room temperature with 452 mg (8.4 mmol) of sodium methoxide. After one to two hours at room temperature, the pH was adjusted to about 7 using 1 N HCl and the solvent removed in vacuo. The residue was taken up in sat. NaHCO₃ solution and extracted twice with ethyl acetate. The combined organic phases were dried over MgSO₄ and concentrated. Chromatography on silica gel using a dichloromethane/methanol mixture afforded 373 mg of the title compound as a pale yellow solid.

1a: N-[4-(6,8-dichloro-2-methyl-1,2,3,4-tetrahydroisoquinolin-4-yl)phenyl]-(2R,3S,4R,5R)-2,3,4,5,6-pentahydroxyhexanamide hydrochloride 201 mg (0.4 mmol) of [4-(6,8-dichloro-2-methyl-1,2,3,4-tetrahydroisoquinolin-4-yl)phenyl]-(2R,3S,4R,5R)-2,3,4,5,6-pentahydroxyhexanamide (example compound 1) were taken up in 75 ml of H₂O and admixed at room temperature with 4.14 ml of 0.1 M HCl. The mixture was stirred for 15 minutes, filtered and freeze-dried to obtain 177 mg of the desired hydrochloride.

Example 2

N-[3-(6,8-dichloro-2-methyl-1,2,3,4-tetrahydroisoquinolin-4-yl)phenyl]-(2R,3S,4R,5R)-2,3,4,5,6-pentahydroxyhexanamide

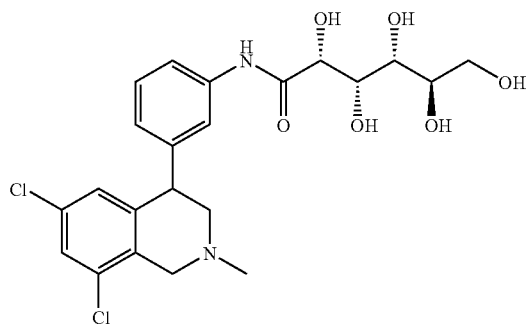

Intermediate 1: 3-(6,8-dichloro-2-methyl-1,2,3,4-tetrahydroisoquinolin-4-yl)phenylamine Starting from 2,4-dichlorobenzylmethylamine (Example 1, intermediate 1) and N-[3-(2-bromoacetyl)phenyl]acetamide (cf. Example 1, intermediate 2), the aniline derivative 3-(6,8-dichloro-2-methyl-1,2,3,4-tetrahydroisoquinolin-4-yl)phenylamine (cf. Example 1, intermediate 6) was prepared in a similar manner to the synthetic route described in Example 1.

Intermediate 2: N-[3-(6,8-dichloro-2-methyl-1,2,3,4-tetrahydroisoquinolin-4-yl)phenyl]-(2R,3S,4R,5R)-2,3,4,5,6-penta-O-acetylhexanamide 3.1 g (10 mmol) of 3-(6,8-dichloro-2-methyl-1,2,3,4-tetrahydroisoquinolin-4-yl)phenylamine (intermediate 1) were dissolved in 100 ml of pyridine and admixed at 0° C. with a solution of 1.2 equivalents of 2,3,4,5,6-penta-O-acetylgluconyl chloride in 60 ml of dichloromethane. The mixture was stirred at room temperature. Once the monitoring of the reaction indicated complete conversion, the mixture was concentrated and the residue taken up in dichloromethane. Washing was effected once with H₂O, once with saturated NaHCO₃ solution, twice with 1 N HCl and once more with H₂O, followed by drying over MgSO₄ and concentration. The crude product obtained in this way (6.91 g) could be used in the next reaction without further purification.

2: N-[3-(6,8-dichloro-2-methyl-1,2,3,4-tetrahydroisoquinolin-4-yl)phenyl]-(2R,3S,4R,5R)-2,3,4,5,6-pentahydroxyhexanamide 6.91 g of the crude product from intermediate 2 were admixed into 200 ml of methanol at room temperature with 2.79 g (51.7 mmol) of sodium methoxide. After 1 to 2 hours at room temperature, the pH was adjusted to about 7 using 1 N HCl and the solvent was removed in vacuo. The residue was taken up in sat. NaHCO$_3$ solution and extracted twice with ethyl acetate. The combined organic phases were dried over MgSO$_4$ and concentrated. Chromatography on silica gel using a dichloromethane/methanol mixture afforded 2.05 g of the title compound as a pale yellow solid.

2a: N-[3-(6,8-dichloro-2-methyl-1,2,3,4-tetrahydroisoquinolin-4-yl)phenyl]-(2R,3S,4R,5R)-2,3,4,5,6-pentahydroxyhexanamide hydrochloride 300 mg (0.6 mmol) of N-[3-(6,8-dichloro-2-methyl-1,2,3,4-tetrahydroisoquinolin-4-yl)phenyl]-(2R,3S,4R,5R)-2,3,4,5,6-pentahydroxyhexanamide (example compound 2) were taken up in 100 ml of H$_2$O and admixed at room temperature with 6.18 ml of 0.1 M HCl. The mixture was stirred for 15 minutes, filtered and freeze-dried to obtain 294 mg of the desired hydrochloride.

Example 3

N-[2-(6,8-dichloro-2-methyl-1,2,3,4-tetrahydroisoquinolin-4-yl)phenyl]-(2R,3S,4R,5R)-2,3,4,5,6-pentahydroxyhexanamide

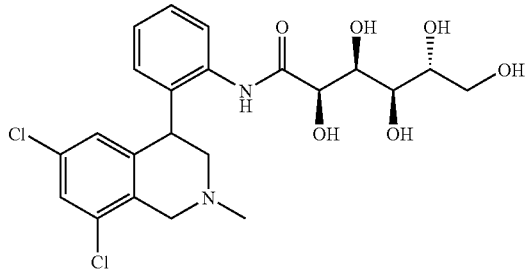

Intermediate 1: N-[2-(2-bromoacetyl)phenyl]acetamide 31 g (0.175 mol) of N-(2-acetylphenyl)acetamide (prepared by acylating 2-aminoacetophenone with acetyl chloride according to Fuerstner, Alois; Jumbam, Denis N.; Tetrahedron; 48; 29; 5991-6010, (1992)) were dissolved in 200 ml of glacial acetic acid. 127 ml of 33% HBr in glacial acetic acid were added and then 8.75 ml (0.175 mol) of bromine were added slowly at room temperature. The mixture was stirred at room temperature overnight. The mixture was stirred into 1.5 l of ice-water, and the precipitated product was filtered off with suction, washed thoroughly with ice-water and dried in vacuo. According to HPLC and NMR, the crude product contained some reactant and dibrominated product, but was clean enough for the further reaction (approx. 85%).

Yield: 43 g

Intermediate 2: N-(2-{2-[(2,4-dichlorobenzyl)methylamino]acetyl}phenyl)acetamide 12.4 g (65.24 mmol) of 2,4-dichlorobenzylmethylamine (Example 1, intermediate 1) were dissolved in 200 ml of dioxane. To this were added 19.96 g of the crude product of the above bromination, likewise dissolved in 200 ml of dioxane, and 45 ml of triethylamine. The mixture was stirred at room temperature overnight and then filtered. The filtrate was evaporated, and the residue was taken up in ethyl acetate and washed with saturated sodium hydrogen carbonate and sodium chloride solution, dried over sodium sulfate and concentrated by rotary evaporation. According to NMR, the crude product (20.4 g) was clean enough for the further reaction.

Intermediate 3: N-(2-{2-[(2,4-dichlorobenzyl)methylamino]-1-hydroxyethyl}-phenyl)acetamide 20 g of the crude product of the preceding stage (approx. 50 mmol) were dissolved in 200 ml of methanol and cooled to <5° C. in an ice bath. 4.3 g (109 mmol) of sodium borohydride were added with good stirring in portions, in such a way that the internal temperature did not exceed 10° C. Subsequently, stirring was continued in the ice bath for another 30 min and at room temperature for 1 hour. After standing overnight, the mixture was evaporated, and the residue was taken up in ethyl acetate, washed 3× with water and 1× with sodium chloride solution, dried over sodium sulfate and concentrated by rotary evaporation. The crude product (19.4 g) was used further without purification.

Intermediate 4: 1-(2-aminophenyl)-2-[(2,4-dichlorobenzyl)methylamino]ethanol 10 g of the crude product from the preceding stage were dissolved in 300 ml of methanol. 200 ml of concentrated hydrochloric acid were added and the mixture was stirred at 50° C. for 10 hours. The mixture was allowed to cool and poured into water, and the pH was adjusted to 10-12 using 20% NaOH. The product was extracted with ethyl acetate, and the combined extracts were washed with sodium chloride solution, dried over sodium sulfate and evaporated. The crude product (9.9 g) contained a little sodium chloride, which did not, however, disrupt the further reaction.

Intermediate 5: 2-(6,8-dichloro-2-methyl-1,2,3,4-tetrahydroisoquinolin-4-yl)phenylamine 9.9 g of the crude product from the preceding stage were dissolved in 350 ml of chloroform. With cooling in an ice bath, 123 ml of concentrated sulfuric acid were added dropwise. Stirring was carried out in the ice bath for 2 hours, then the mixture was gradually warmed to room temperature and finally heated to 50° C. overnight. The cooled mixture was poured onto ice and made alkaline using sodium hydroxide solution (pH>10). The organic phase was removed, the aqueous phase was extracted twice with methylene chloride, and the combined organic phases were washed with water and NaCl, dried over sodium sulfate and evaporated.

Intermediate 6: N-[2-(6,8-dichloro-2-methyl-1,2,3,4-tetrahydroisoquinolin-4-yl)phenyl]-(2R,3S,4R,5R)-2,3,4,5,6-penta-O-acetylhexanamide 614 mg (2.0 mmol) of 2-(6,8-dichloro-2-methyl-1,2,3,4-tetrahydroisoquinolin-4-yl)phenylamine (intermediate 5) were dissolved in 20 ml of pyridine and admixed at 0° C. with a solution of 1.5 equivalents of 2,3,4,5,6-penta-O-acetylgluconyl chloride in 10 ml of dichloromethane. The mixture was stirred at room temperature. Once the monitoring of the reaction indicated complete conversion, the mixture was concentrated and the residue taken up in dichloromethane. Washing was effected once with H$_2$O, once with saturated NaHCO$_3$ solution, twice with 1 N HCl and once more with H$_2$O, followed by drying over MgSO$_4$ and concentration. The crude product obtained in this way (1.27 g) was able to be used in the next reaction without further purification.

3: N-[2-(6,8-dichloro-2-methyl-1,2,3,4-tetrahydroisoquinolin-4-yl)phenyl]-(2R,3S,4R,5R)-2,3,4,5,6-pentahydroxyhexanamide 1.27 g of the crude product from intermediate 6 were admixed in 30 ml of methanol at room temperature with 513 mg (9.5 mmol) of sodium methoxide. After 1 to 2 hours at room temperature, the pH was adjusted to about 7 using 1 N HCl and the solvent removed in vacuo. The residue was taken up in sat. NaHCO$_3$ solution and extracted twice with ethyl acetate. The combined organic phases were washed once more with H$_2$O, dried over MgSO$_4$ and concentrated. Chromatography on silica gel using a dichloromethane/methanol mixture afforded 313 mg of the title compound as a pale yellow solid.

3a: N-[2-(6,8-dichloro-2-methyl-1,2,3,4-tetrahydroisoquinolin-4-yl)phenyl]-(2R,3S,4R,5R)-2,3,4,5,6-pentahydroxyhexanamide hydrochloride 145.5 mg (0.3 mmol) of N-[2-(6,8-dichloro-2-methyl-1,2,3,4-tetrahydroisoquinolin-4-yl)phenyl]-2,3,4,5,6-pentahydroxygluconamide (example compound 3) were taken up in 75 ml of H$_2$O and admixed at room temperature with 3.0 ml of 0.1 M HCl. The mixture was stirred for 15 minutes, filtered and freeze-dried to obtain 149 mg of the desired hydrochloride.

Example 4

4a: N-[(R)-3-(6,8-dichloro-2-methyl-1,2,3,4-tetrahydroisoquinolin-4-yl)phenyl]-(2R,3S,4R,5R)-2,3,4,5,6-pentahydroxyhexanamide and
4b: N-[(S)-3-(6,8-dichloro-2-methyl-1,2,3,4-tetrahydroisoquinolin-4-yl)phenyl]-(2R,3S,4R,5R)-2,3,4,5,6-pentahydroxyhexanamide

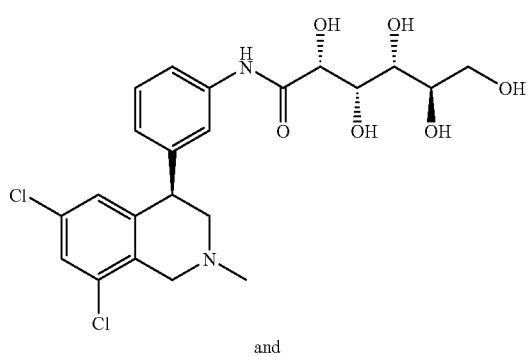

and

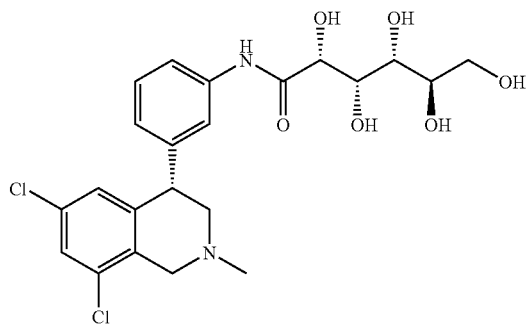

2.0 g of the example compound 2 were separated on a chiral phase into the two diastereomers.

Preparative Separation Conditions for Baseline Separation:
Chiral column: Chiralpak AD9 250×50 mm+Chiralpak AD2 250×50 mm
Solvent: 2:1:1 heptane:ethanol:methanol
Flow rate: 150 ml/min Analytical Data on a Chiral Phase:
Chiral column: Chiralpak ADH/40 250×4.6
Solvent: 2:1:1 heptane:ethanol:methanol
Flow rate: 1 ml/min
Temperature: 30° C.
Retention time of diastereomer A: 4.5 minutes,
Yield of diastereomer A: 988 mg;
Retention time of diastereomer B: 7.5 minutes,
Yield of diastereomer B: 942 mg.

Example 5

N-[(R or S)-3-(6,8-dichloro-2-methyl-1,2,3,4-tetrahydroisoquinolin-4-yl)phenyl]-(2R,3S,4R,5R)-2,3,4,5,6-pentahydroxyhexanamide hydrochloride

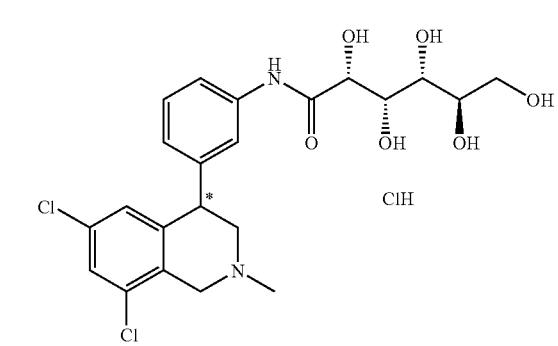

300 mg (0.6 mmol) of N-[(R or S)-3-(6,8-dichloro-2-methyl-1,2,3,4-tetrahydroisoquinolin-4-yl)phenyl]-(2R,3S,4R,5R)-2,3,4,5,6-pentahydroxyhexanamide (Example compound 4a or 4b; diastereomer B) were taken up in 20 ml of H$_2$O and admixed at room temperature with 6.18 ml of 0.1 M HCl. The mixture is stirred for 15 minutes, filtered and freeze-dried to obtain 297 mg of the desired hydrochloride.

Example 6

1-[3-(6,8-dichloro-2-methyl-1,2,3,4-tetrahydroisoquinolin-4-yl)phenyl]-3-(2-hydroxy-1-hydroxymethylethyl)urea

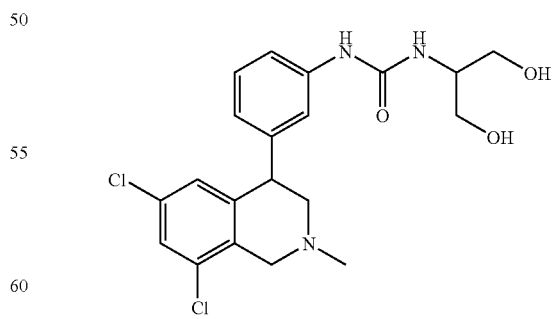

Intermediate 1: 4-nitrophenyl [3-(6,8-dichloro-2-methyl-1,2,3,4-tetrahydroisoquinolin-4-yl)phenyl]carbamate hydrochloride 350 mg (1.1 mmol) of 3-(6,8-dichloro-2-methyl-1,2,3,4-tetrahydroisoquinolin-4-yl)phenylamine (Example compound 2, intermediate 1) were dissolved in 17.5 ml of dichloromethane and admixed with stirring with 230 mg (1.1 mmol) of 4-nitrophenyl chloroformate. After 4.5 hours, a further 0.1 equivalent (23 mg) of 4-nitrophenyl chloroformate was added and the solution was stirred overnight. For workup, the resulting precipitate was filtered off and washed with dichloromethane. The crude product obtained in this way could be reacted further without further purification.

6: 1-[3-(6,8-dichloro-2-methyl-1,2,3,4-tetrahydroisoquinolin-4-yl)phenyl]-3-(2-hydroxy-1-hydroxymethylethyl)urea 1.02 g (2.0 mmol) of 4-nitrophenyl [3-(6,8-dichloro-2-methyl-1,2,3,4-tetrahydroisoquinolin-4-yl)phenyl]carbamate hydrochloride (intermediate 1) were dissolved in 30 ml of abs. DMF and admixed at 0° C. with a solution of 200.5 mg (2.2 mmol) of 2-amino-1,3-propanediol in 25 ml of abs. DMF. The mixture was stirred at room temperature for 3 hours. After standing overnight, the solvent was removed in vacuo and the residue partitioned between ethyl acetate and saturated NaHCO₃ solution. The organic phase was removed and the aqueous extracted twice more with ethyl acetate. The combined organic phases were washed with saturated NaCl solution, dried over Na₂SO₄ and concentrated. Chromatography of the crude product obtained in this way on silica gel (dichloromethane/methanol mixture) afforded 500 mg of the desired urea.

6a: 1-[3-(6,8-dichloro-2-methyl-1,2,3,4-tetrahydroisoquinolin-4-yl)phenyl]-3-(2-hydroxy-1-hydroxymethylethyl)urea hydrochloride 200 mg of 1-[3-(6,8-dichloro-2-methyl-1,2,3,4-tetrahydroisoquinolin-4-yl)phenyl]-3-(2-hydroxy-1-hydroxymethylethyl)urea (Example compound 6) were dissolved in 40 ml of 0.1 M HCl, filtered and freeze-dried to obtain 194 mg of the desired hydrochloride.

Example 7

1-[3-(6,8-dichloro-2-methyl-1,2,3,4-tetrahydroisoquinolin-4-yl)phenyl]-3-(2-hydroxy-1,1-bishydroxymethylethyl)urea

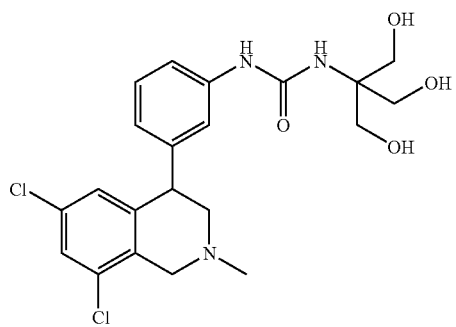

1.02 g (2.0 mmol) of 4-nitrophenyl [3-(6,8-dichloro-2-methyl-1,2,3,4-tetrahydroisoquinolin-4-yl)phenyl]carbamate hydrochloride (intermediate 1, Example 6) were reacted with 2-amino-2-hydroxymethylpropane-1,3-diol in a similar manner to that described in Example 6. Similar workup afforded 395 mg of the title compound.

7a: 1-[3-(6,8-dichloro-2-methyl-1,2,3,4-tetrahydroisoquinolin-4-yl)phenyl]-3-(2-hydroxy-1,1-bishydroxymethylethyl)urea hydrochloride A similar procedure to the method described in Example 6a starting from 200 mg of 1-[3-(6,8-dichloro-2-methyl-1,2,3,4-tetrahydroisoquinolin-4-yl)phenyl]-3-(2-hydroxy-1,1-bishydroxymethylethyl)urea (Example compound 7) afforded 195 mg of the desired hydrochloride.

Example 8

1-[3-(6,8-dichloro-2-methyl-1,2,3,4-tetrahydroisoquinolin-4-yl)phenyl]-3-((2S,3R,4R,5R)-2,3,4,5,6-pentahydroxyhexyl)urea

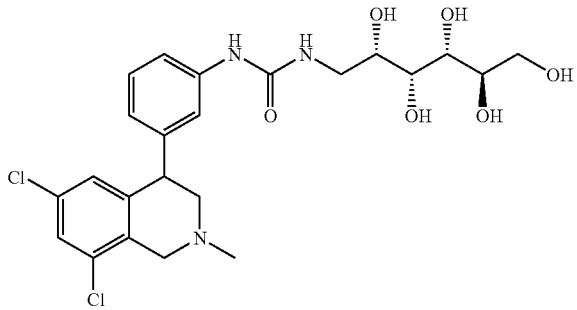

1.02 g (2.0 mmol) of 4-nitrophenyl [3-(6,8-dichloro-2-methyl-1,2,3,4-tetrahydroisoquinolin-4-yl)phenyl]carbamate hydrochloride (intermediate 1, Example 6) were reacted with D-glucamine in a similar manner to the way described in Example 6. Similar workup afforded 273 mg of the title compound.

8a: 1-[3-(6,8-dichloro-2-methyl-1,2,3,4-tetrahydroisoquinolin-4-yl)phenyl]-3-((2S ,3R,4R,5R)-2,3,4,5,6-pentahydroxyhexyl)urea hydrochloride A similar procedure to the method described in Example 6a starting from 200 mg of 1-[3-(6,8-dichloro-2-methyl-1,2,3,4-tetrahydroisoquinolin-4-yl)phenyl]-3-((2S,3R,4R,5R)-6-pentahydroxyhexyl)urea (Example compound 8) afforded 181 mg of the desired hydrochloride.

Example 9

1-[3-(6,8-dichloro-2-methyl-1,2,3,4-tetrahydroisoquinolin-4-yl)phenyl]-3-((4R,5S ,6R)-2,4,5-trihydroxy-6-hydroxymethyltetrahydropyran-3-yl)urea

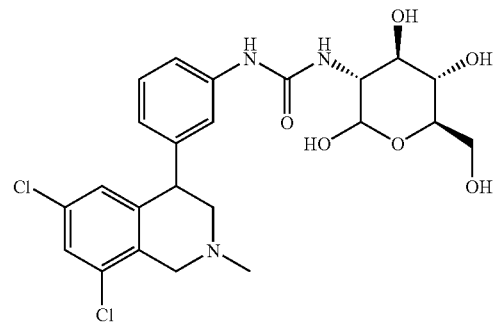

254 mg (0.5 mmol) of 4-nitrophenyl [3-(6,8-dichloro-2-methyl-1,2,3,4-tetrahydroisoquinolin-4-yl)phenyl]carbamate hydrochloride (intermediate 1, Example 6) were initially charged in 7 ml of abs. DMF and admixed at 0° C. with a suspension of 119 mg (0.55 mol) of D-glucosamine hydrochloride in 5 ml of abs. DMF. A similar procedure to the method described in Example 6 afforded, after chromatography on silica gel, 87 mg of the title compound.

Example 10

{N-[3-(6,8-dichloro-2-methyl-1,2,3,4-tetrahydroisoquinolin-4-yl)phenyl]-N'-(1-sulfo-2-ethyl)}urea hydrochloride

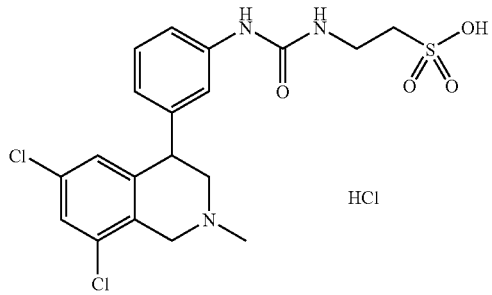

1.02 g (2.0 mmol) of 4-nitrophenyl [3-(6,8-dichloro-2-methyl-1,2,3,4-tetrahydroisoquinolin-4-yl)phenyl]carbamate hydrochloride (intermediate 1, Example 6) were admixed in 30 ml of abs. DMF at 0° C. with 275 mg (2.2 mmol) of 2-aminoethanesulfonic acid, and also 0.83 ml (6.0 mmol) of triethylamine and stirred at room temperature for 2 hours. After standing overnight, the liquid was filtered off from the precipitate which had formed and was concentrated in vacuo. The residue was taken up in saturated $NaHCO_3$ solution, filtered and neutralized with 1 N HCl, and a solid precipitated out. Filtering off and drying afforded 356 mg of the title compound as a crude product. The mother liquor was freeze-dried and the residue triturated with dichloromethane. The insoluble residue (634 mg) was combined with the precipitate (356 mg) which had already been obtained and chromatographed on silica gel. After a further purification on a preparative HPLC, the product fractions were combined and freeze-dried. The product obtained in this way was dissolved in 1 N HCl and freeze-dried once again to obtain the desired hydrochloride. Repeated dissolution in $H_2O$ and further freeze-drying afforded 271 mg of the title compound.

Example 11

{N-[3-(6,8-dichloro-2-methyl-1,2,3,4-tetrahydroisoquinolin-4-yl)phenyl]-N'-(ethyl-2-trimethylammonium)}urea chloride hydrochloride

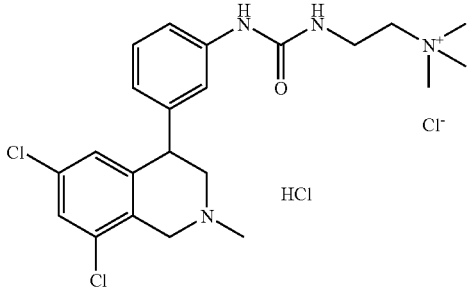

1.02 g (2.0 mmol) of 4-nitrophenyl [3-(6,8-dichloro-2-methyl-1,2,3,4-tetrahydroisoquinolin-4-yl)phenyl]carbamate hydrochloride (intermediate 1, Example 6) were dissolved in 30 ml of abs. DMF and admixed at 0° C. with a solution of 333 mg (1.9 mmol) of 2-aminoethyltrimethylammonium chloride hydrochloride in 5 ml of DMF. After addition of 0.277 ml (2.0 mmol) of triethylamine, the mixture was stirred at room temperature for 4 hours. After standing overnight, the mixture was filtered and concentrated in vacuo. The residue was taken up in $H_2O$ and freeze-dried to obtain 1.77 g of crude product. Purification on a preparative HPLC afforded the desired product which could be converted to the title compound by dissolution in 1 N HCl and freeze-drying. After repeated dissolution in $H_2O$ and further freeze-drying, 544 mg of the desired hydrochloride were obtained.

Example 12

{N-[3-(6,8-dichloro-2-methyl-1,2,3,4-tetrahydroisoquinolin-4-yl)phenyl]-N'-(1-carboxy-3-hydroxy-2S-propyl)}urea

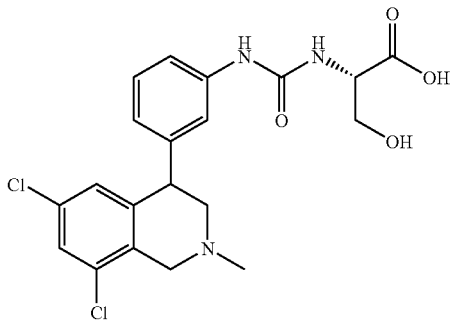

Intermediate 1: {N-[3-(6,8-dichloro-2-methyl-1,2,3,4-tetrahydroisoquinolin-4-yl)phenyl]-N'-(1-ethoxycarbonyl-3-hydroxy-2S-propyl)}urea 254 mg (0.5 mmol) of 4-nitrophenyl [3-(6,8-dichloro-2-methyl-1,2,3,4-tetrahydroisoquinolin-4-yl)phenyl]carbamate hydrochloride (intermediate 1, Example 6) were dissolved in 7 ml of abs. DMF and admixed at 0° C. with a solution of 93 mg (0.55 mol) of (S)-serine ethyl ester hydrochloride in 5 ml of abs. DMF. After adding 104 µl (0.75 mmol) of triethylamine, the mixture was stirred at room temperature. After standing overnight, workup was effected in the manner described in Example 6 to obtain 184 mg of the title compound.

12: {N-[3-(6,8-dichloro-2-methyl-1,2,3,4-tetrahydroisoquinolin-4-yl)phenyl]-N'-(1-carboxy-3-hydroxy-2S-propyl)}urea 170 mg (0.36 mmol) of {N-[3-(6,8-dichloro-2-methyl-1,2,3,4-tetrahydroisoquinolin-4-yl)phenyl]-N'-(1-ethoxycarbonyl-3-hydroxy-2S-propyl)}urea (intermediate 1) were dissolved in 2 ml of methanol and admixed with 2 ml of 2 M KOH. After 3 hours at room temperature, the mixture was concentrated and the residue was taken up in $H_2O$. Once the pH of approx. 7 was attained by adding dilute HCl, the liquid was filtered off from the precipitate which had formed. Drying afforded 89 mg of the title compound.

12a: {N-[3-(6,8-dichloro-2-methyl-1,2,3,4-tetrahydroisoquinolin-4-yl)phenyl]-N'-(1-carboxy-3-hydroxy-2S-propyl)}urea hydrochloride 51 mg of {N-[3-(6,8-dichloro-2-methyl-1,2,3,4-tetrahydroisoquinolin-4-yl)phenyl]-N'-(1-carboxy-3-hydroxy-2S-propyl)}urea (Example compound 12) were dissolved in 20 ml of 0.1 M HCl and freeze-dried to obtain 52 mg of the desired hydrochloride.

Example 13

{N-[3-(6,8-dichloro-2-methyl-1,2,3,4-tetrahydroisoquinolin-4-yl)phenyl]-N'-(1-carboxy-4-aminocarboxy-2S-butyl)}urea hydrochloride

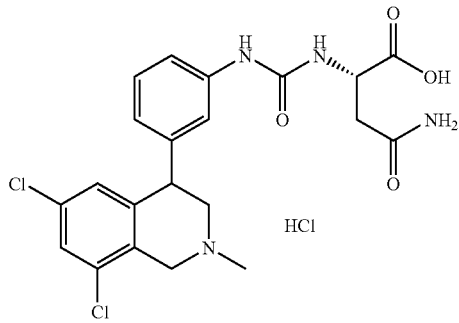

Intermediate 1: {N-[3-(6,8-dichloro-2-methyl-1,2,3,4-tetrahydroisoquinolin-4-yl)phenyl]-N'-(1-tert-butoxycarbonyl-4-aminocarboxy-2S-butyl)}urea 254 mg (0.5 mmol) of 4-nitrophenyl [3-(6,8-dichloro-2-methyl-1,2,3,4-tetrahydroisoquinolin-4-yl)phenyl]carbamate hydrochloride (intermediate 1, Example 6) were reacted with 124 mg (0.55 mmol) of (S)-asparagine tert-butyl ester hydrochloride in a similar manner to the method described in Example 12 to obtain 220 mg of the title compound.

13: {N-[3-(6,8-dichloro-2-methyl-1,2,3,4-tetrahydroisoquinolin-4-yl)phenyl]-N'-(1-carboxy-4-aminocarboxy-2S-butyl)}urea hydrochloride 210 mg (0.4 mmol) of intermediate 1 were dissolved in 3 ml of trifluoroacetic acid and left to stand at room temperature for 3 hours. Subsequently, the mixture was concentrated, and the residue was triturated with ether and filtered off with suction to obtain 230 mg of the corresponding trifluoroacetate. This was converted to the desired hydrochloride by dissolution in 0.1 N HCl and subsequent freeze-drying.

Example 14

3-(6,8-dichloro-2-methyl-1,2,3,4-tetrahydroisoquinolin-4-yl)-N-((2S,3R,4R,5R)-2,3,4,5,6-pentahydroxyhexyl)benzamide hydrochloride

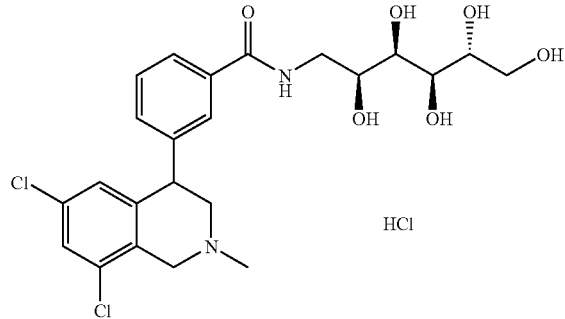

Intermediate 1: 3-acetylbenzoic acid

The title compound was prepared in a manner known to those skilled in the art from 3-acetylbenzonitrile by hydrolyzing the nitrile group.

Intermediate 2: ethyl 3-acetylbenzoate

The title compound was prepared in a manner known to those skilled in the art by acid-catalyzed esterification of 3-acetylbenzoic acid (intermediate 1).

Intermediate 3: ethyl 3-(2-bromoacetyl)benzoate

The title compound is synthesized from ethyl 3-acetylbenzoate (intermediate 2) in a similar manner to the method described in Example 1, intermediate 2.

Intermediate 4: ethyl 3-(6,8-dichloro-2-methyl-1,2,3,4-tetrahydroisoquinolin-4-yl)benzoate In a similar manner to the synthetic route described under Example 1, the process was continued starting from ethyl 3-(2-bromoacetyl)benzoate (intermediate 3) and 2,4-dichlorobenzylmethylamine (Example 1, intermediate 1) to obtain ethyl 3-(6,8-dichloro-2-methyl-1,2,3,4-tetrahydroisoquinolin-4-yl)benzoate after alkylation reaction, reduction and ring closure reaction.

Intermediate 5: 3-(6,8-dichloro-2-methyl-1,2,3,4-tetrahydroisoquinolin-4-yl)benzoic acid 3.3 g of ethyl 3-(6,8-dichloro-2-methyl-1,2,3,4-tetrahydroisoquinolin-4-yl)benzoate (intermediate 4) were dissolved in 60 ml of methanol and admixed with 60 ml of 2 N KOH. After two hours at 50° C., the mixture was concentrated in vacuo and the residue partitioned between water and ether. The water phase was adjusted to a pH of approx. 6 using 2 N HCl and the precipitate which formed was filtered off with suction. Drying afforded 1.7 g of the title compound as a colorless solid.

14: 3-(6,8-dichloro-2-methyl-1,2,3,4-tetrahydroisoquinolin-4-yl)-N-((2S,3R,4R,5R)-2,3,4,5,6-pentahydroxyhexyl)benzamide hydrochloride 300 mg (0.9 mmol) of 3-(6,8-dichloro-2-methyl-1,2,3,4-tetrahydroisoquinolin-4-yl)benzoic acid (intermediate 5) were initially charged in 10 ml of DMF and admixed at 0° C. with 0.137 ml (1.0 mmol) of triethylamine, and also 354 mg (1.1 mmol) TOTU. The mixture was stirred at 0° C. for 15 minutes and at room temperature for 30 minutes. Subsequently, this solution was added dropwise to a second solution consisting of 196 mg (1.08 mmol) of D-glucamine and 0.137 ml (1.0 mmol) of triethylamine in 10 ml of DMF and 3 ml of $H_2O$, and stirred at room temperature. After 2 hours, the mixture was concentrated in vacuo and the residue purified on silica gel. After a further purification on a preparative HPLC, the desired benzamide was obtained as the trifluoroacetate. Dissolution in 0.1 N HCl and subsequent freeze-drying afforded the desired hydrochloride as a colorless solid.

Example 15

3-(6,8-dichloro-2-methyl-1,2,3,4-tetrahydroisoquinolin-4-yl)-N-(2-hydroxy-1-hydroxymethylethyl)benzamide hydrochloride

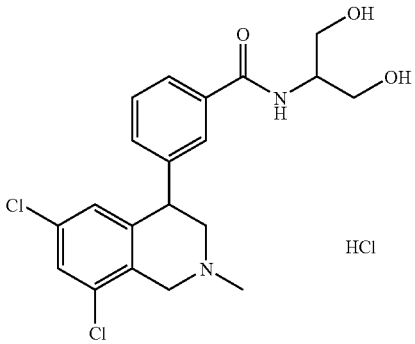

The title compound was prepared in a similar manner to the method described in Example 14 starting from 3-(6,8- dichloro-2-methyl-1,2,3,4-tetrahydroisoquinolin-4-yl)benzoic acid (Example 14, intermediate 5) and 2-amino-1,3-propanediol.

Example 16

(S)-2-[3-(6,8-dichloro-2-methyl-1,2,3,4-tetrahydroisoquinolin-4-yl)benzoylamino]-3-hydroxypropionic acid hydrochloride

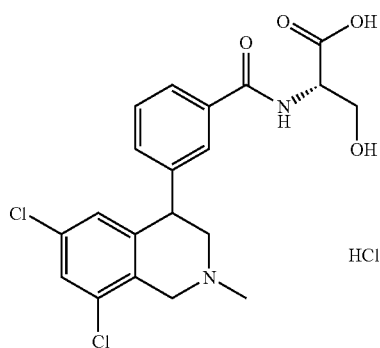

The title compound was prepared in a similar manner to the method described in Example 14 starting from 3-(6,8-dichloro-2-methyl-1,2,3,4-tetrahydroisoquinolin-4-yl)benzoic acid (Example 14, intermediate 5) and L-(+)-serine.

Example 17

(S)-2-[3-(6,8-dichloro-2-methyl-1,2,3,4-tetrahydroisoquinolin-4-yl)benzoylamino]succinic acid hydrochloride

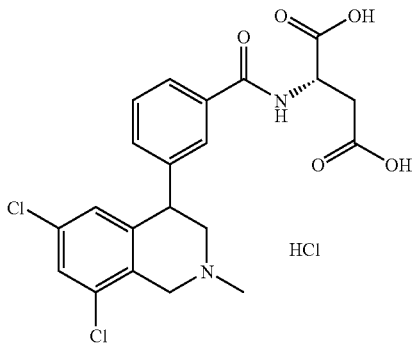

Intermediate 1: Di-tert-butyl (S)-2-[3-(6,8-dichloro-2-methyl-1,2,3,4-tetrahydroisoquinolin-4-yl)benzoylamino]succinate 300 mg (0.9 mmol) of 3-(6,8-dichloro-2-methyl-1,2,3,4-tetrahydroisoquinolin-4-yl)benzoic acid (Example 14, intermediate 5) were reacted in a similar manner to the method described in Example 14 with 304 mg (1.0 mmol) of di-tert-butyl aspartate in a TOTU-mediated coupling reaction to obtain 170 mg of the title compound as the trifluoroacetate after purification on a preparative HPLC.

17: 2S-[3-(6,8-dichloro-2-methyl-1,2,3,4-tetrahydroisoquinolin-4-yl)benzoylamino]succinic acid hydrochloride 170 mg of di-tert-butyl 2S-[3-(6,8-dichloro-2-methyl-1,2,3,4-tetrahydroisoquinolin-4-yl)benzoylamino]succinate (intermediate 1) were dissolved in 15 ml of dichloromethane and admixed with 5 ml of trifluoroacetic acid. After 1 hour at room temperature, the mixture was concentrated in vacuo, and the residue was taken up in 30 ml of 0.1 N HCl and freeze-dried. After repeated dissolution in $H_2O$ and further freeze-drying, 130 mg of the title compound were obtained.

Example 18

(S)-2-[3-(6,8-dichloro-2-methyl-1,2,3,4-tetrahydroisoquinolin-4-yl)benzoylamino]-4-succinamic acid hydrochloride

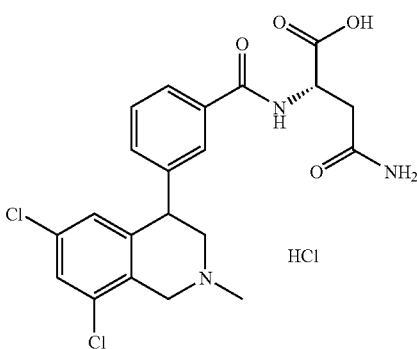

Intermediate 1: tert-butyl (S)-2-[3-(6,8-dichloro-2-methyl-1,2,3,4-tetrahydroisoquinolin-4-yl)benzoylamino]-4-succinamate 300 mg (0.9 mmol) of 3-(6,8-dichloro-2-methyl-1,2,3,4-tetrahydroisoquinolin-4-yl)benzoic acid (Example 14, intermediate 5) were reacted in a similar manner to the method described in Example 14 with 242 mg (1.08 mmol) of tert-butyl aspartate in a TOTU-mediated coupling reaction to obtain 550 mg of the title compound after purification on silica gel.

18: (S)-2-[3-(6,8-dichloro-2-methyl-1,2,3,4-tetrahydroisoquinolin-4-yl)benzoylamino]-4-succinamic acid hydrochloride 550 mg of tert-butyl 2S-[3-(6,8-dichloro-2-methyl-1,2,3,4-tetrahydroisoquinolin-4-yl)benzoylamino]-4-succinamate (intermediate 1) were dissolved in 20 ml of dichloromethane and admixed at room temperature with 5 ml of trifluoroacetic acid. After 3 hours, the mixture was concentrated in vacuo and codistillation with toluene was effected once. The residue was dissolved in 0.1 N HCl with heating, filtered and concentrated in vacuo. The residue was dissolved in H$_2$O and freeze-dried to obtain 322 mg of the title compound.

Example 19

N-[3-(6,8-dichloro-2-methyl-1,2,3,4-tetrahydroisoquinolin-4-yl)phenyl]-N'-[1-carboxy-5-guanidino-2S-pentyl]urea hydrochloride

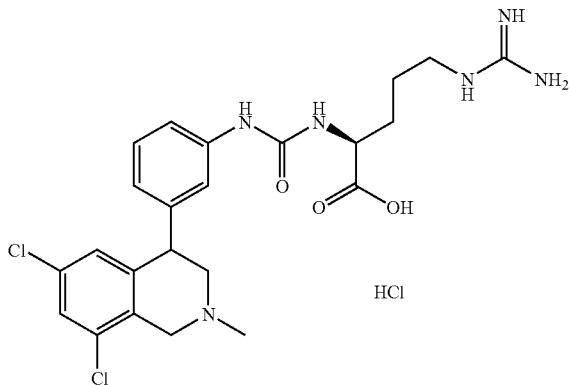

Intermediate 1: 1-[3-(6,8-dichloro-2-methyl-1,2,3,4-tetrahydroisoquinolin-4-yl)phenyl]-3-[1-tert-butoxycarbonyl-5-N'-(2,2,5,7,8-pentamethylchromyl-6-sulfonyl)guanidino-2S-pentyl]urea 373 mg (0.73 mmol) of 4-nitrophenyl [3-(6,8-dichloro-2-methyl-1,2,3,4-tetrahydroisoquinolin-4-yl)phenyl]carbamate hydrochloride (intermediate 1, Example 6) were dissolved in 10 ml of abs. DMF and reacted at 0° C. with 400 mg (0.8 mmol) of tert-butyl S-2-amino-5-(N'-(2,2,5,7,8-pentamethylchromyl-6-sulfonyl)guanidinopentanoate in a similar manner to the method described in Example 6 to obtain 657 mg of the title compound after chromatography on silica gel.

19: N-[3-(6,8-dichloro-2-methyl-1,2,3,4-tetrahydroisoquinolin-4-yl)phenyl]-N'-[1-carboxy-5-guanidino-2S-pentyl]urea hydrochloride 590 mg of 1-[3-(6,8-dichloro-2-methyl-1,2,3,4-tetrahydroisoquinolin-4-yl)phenyl]-3-[1-tert-butoxycarbonyl-5-N'-(2,2,5,7,8-pentamethylchromyl-6-sulfonyl)guanidino-2S-pentyl]urea were taken up in 25 ml of trifluoroacetic acid and stirred at room temperature for 1 hour. Afterwards, the mixture was concentrated in vacuo, and the residue was triturated with ether and filtered off with suction. The resulting crude product was taken up in 1 N HCl, filtered and freeze-dried. After purification on a preparative HPLC, the product fractions were concentrated, dissolved in 0.1 N HCl and freeze-dried. Afterwards, dissolution in H$_2$O was repeated and was followed by further freeze-drying to obtain 170 mg of the title compound.

Example 20

{N-[3-(6,8-dichloro-2-methyl-1,2,3,4-tetrahydroisoquinolin-4-(R or S)-yl)phenyl]-N'-(1-carboxy-4-aminocarboxy-2S-butyl)}urea hydrochloride

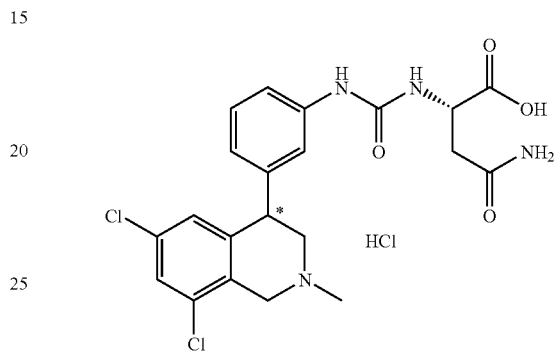

Intermediate 1

1a: (R)-3-(6,8-dichloro-2-methyl-1,2,3,4-tetrahydroisoquinolin-4-yl)phenylamine and 1b: (S)-3-(6,8-dichloro-2-methyl-1,2,3,4-tetrahydroisoquinolin-4-yl)phenylamine 10 g of 3-(6,8-dichloro-2-methyl-1,2,3,4-tetrahydroisoquinolin-4-yl)phenylamine (Example 2, intermediate 1) were separated into the enantiomers on a chiral phase.

Preparative Separation Conditions in Baseline Separation:
Chiral column: Chiralpak AD10 50×10 cm, base-preconditioned;
Solvent: 45:4:1 acetonitrile:ethanol:methanol
Flow rate: 300 ml/min Analytical Data on a Chiral Phase:
Chiral column: Chiralpak ADH/33 250×4.6, base-preconditioned;
Solvent: 45:4:1 acetonitrile:ethanol:methanol
Flow rate: 1 ml/min
Temperature: 30° C.
Retention time of enantiomer A: 4.498 minutes,
Yield of enantiomer A: 4.0 g;
Retention time of enantiomer B: 5.480 minutes,
Yield of enantiomer B: 4.5 g.

Intermediate 2: 4-nitrophenyl (R or S)-[3-(6,8-dichloro-2-methyl-1,2,3,4-tetrahydroisoquinolin-4-yl)phenyl]carbamate hydrochloride 1.54 g (5.0 mmol) of enantiomer B of intermediate 1 were reacted with 1.1 equivalents of 4-nitrophenyl chloroformate in a similar manner to the method described in Example 6, intermediate 1 to obtain 1.87 g of the title compound.

{N-[3-(6,8-dichloro-2-methyl-1,2,3,4-tetrahydroisoquinolin-4-(R or S)-yl)phenyl]-N'-(1-carboxy-4-aminocarboxy-2S-butyl)}urea hydrochloride Starting from 4-nitrophenyl (R or S)-[3-(6,8-dichloro-2-methyl-1,2,3,4-tetrahydroisoquinolin-4-yl)phenyl]carbamate hydrochloride (intermediate 2) and tert-butyl (S)-aspartate hydrochloride, the title compound was prepared in diastereomerically pure form in a similar manner to the synthetic route specified in Example 13.

Example 21

{N-[3-(6,8-dichloro-2-methyl-1,2,3,4-tetrahydroisoquinolin-4-(R or S)-yl)phenyl]-N'-(1-carboxy-3-hydroxy-2S-propyl)}urea hydrochloride

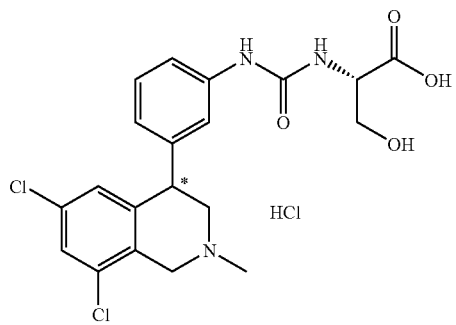

Intermediate 1: {N-[3-(6,8-dichloro-2-methyl-1,2,3,4-tetrahydroisoquinolin-4-(R or S)-yl)phenyl]-N'-(1-tert-butoxycarbonyl-3-butoxy-2S-propyl)}urea 509 mg (1.0 mmol) of 4-nitrophenyl (R or S)-[3-(6,8-dichloro-2-methyl-1,2,3,4-tetrahydroisoquinolin-4-yl)phenyl]carbamate hydrochloride (intermediate 2, Example 20) were reacted with 280 mg (1.1 mmol) of tert-butyl (S)-2-amino-3-tert-butoxypropionate hydrochloride in a similar manner to that described in Example 12, intermediate 1 to obtain 460 mg of the title compound.

21: {N-[3-(6,8-dichloro-2-methyl-1,2,3,4-tetrahydroisoquinolin-4-(R or S)-yl)phenyl]-N'-(1-carboxy-3-hydroxy-2S-propyl)}urea hydrochloride 270 mg (0.49 mmol) of {N-[3-(6,8-dichloro-2-methyl-1,2,3,4-tetrahydroisoquinolin-4-(R or S)-yl)phenyl]-N'-(1-tert-butoxycarbonyl-3-butoxy-2S-propyl)}urea (intermediate 1) were stirred in 12 ml of trifluoroacetic acid at room temperature for 1 hour. Subsequently, the mixture was concentrated. The residue was triturated with ether and filtered off with suction to obtain 247 mg of the trifluoroacetate. This was dissolved in 30 ml of H$_2$O/30 ml of 1 N HCl and freeze-dried. Repeated dissolution in H$_2$O and subsequent freeze-drying afforded 182 mg of the title compound.

Example 22

1-[3-(6,8-dichloro-2-methyl-1,2,3,4-tetrahydroisoquinolin-4-(R or S)-yl)phenyl]-3-(2-hydroxy-1,1-bishydroxymethylethyl)urea hydrochloride

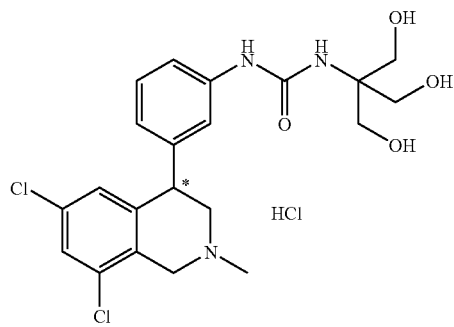

Starting from 509 mg (1.0 mmol) of 4-nitrophenyl (R or S)-[3-(6,8-dichloro-2-methyl-1,2,3,4-tetrahydroisoquinolin-4-yl)phenyl]carbamate hydrochloride (intermediate 2, Example 20) and 2-amino-2-hydroxymethylpropane-1,3-diol, a similar procedure to the method described in example 7/7a afforded 101 mg of the desired enantiomerically pure hydrochloride.

Example 23

1-[3-((R or S)-6,8-dichloro-2-methyl-1,2,3,4-tetrahydroisoquinolin-4-yl)phenyl]-3-((2S,3R,4R,5R)-2,3,4,5,6-pentahydroxyhexyl)urea hydrochloride

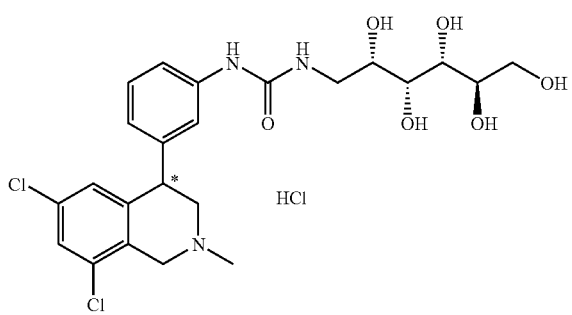

Starting from 509 mg (1.0 mmol) of 4-nitrophenyl (R or S)-[3-(6,8-dichloro-2-methyl-1,2,3,4-tetrahydroisoquinolin-4-yl)phenyl]carbamate hydrochloride (intermediate 2, Example 20) and D-glucamine, a similar procedure to the method described in Example 8/8a afforded 169 mg of the desired diastereomerically pure hydrochloride.

Example 24

5-(6,8-dichloro-2-methyl-1,2,3,4-tetrahydroisoquinolin-4-yl)-N,N'-bis(2-hydroxy-1-hydroxymethylethyl)isophthalamide hydrochloride

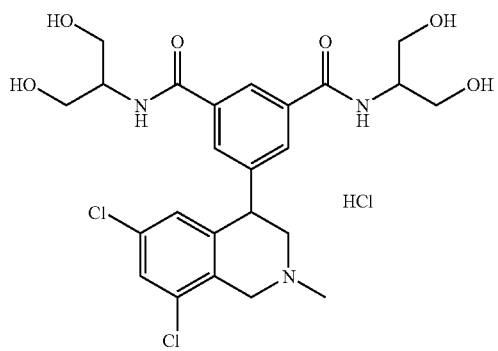

Intermediate 1: 1-(3,5-bis(trifluoromethyl)phenyl)ethanone 5.16 g (20 mmol) of 3,5-bis(trifluoromethyl)benzoic acid were dissolved in 100 ml of abs. THF and admixed at 0° C. with 31.25 ml of a 1.6 M solution of methyllithium in diethyl ether. After the mixture had been stirred at room temperature for 5 hours, excess methyllithium was hydrolyzed by adding $H_2O$ and the solvent was removed in vacuo. The residue was taken up in dichloromethane and washed with saturated $NaHCO_3$ solution. The organic phase was removed, dried over $MgSO_4$ and concentrated. Chromatography on silica gel afforded 3.97 g of the title compound.

Intermediate 2: 1-(3,5-bis(trifluoromethyl)phenyl)-2-bromoethanone 2.97 g (11.6 mmol) of 1-(3,5-bis(trifluoromethyl)phenyl)ethanone (intermediate 1) were dissolved in 15 ml of glacial acetic acid and admixed at 0° C. with 1.82 g (11.4 mmol) of $Br_2$ and stirred at 50° C. for 2.5 hours. After standing overnight, the reaction mixture was added to ice and extracted twice with ethyl acetate. The combined ethyl acetate phases were washed twice more with $H_2O$, dried over $Na_2SO_4$ and concentrated to obtain 4 g of the title compound.

Intermediate 3: 4-(3,5-bis(trifluoromethylphenyl)-6,8-dichloro-2-methyl-1,2,3,4-tetrahydroisoquinoline The process was continued in a similar manner to the synthetic route described under Example 1 starting from 1-(3,5-bis(trifluoromethyl)phenyl)-2-bromoethanone (intermediate 2) and 2,4-dichlorobenzylmethylamine (Example 1, intermediate 1) to obtain the 4-(3,5-bis(trifluoromethylphenyl)-6,8-dichloro-2-methyl-1,2,3,4-tetrahydroisoquinoline after alkylation reaction, reduction and ring closure reaction.

Intermediate 4: 5-(6,8-dichloro-2-methyl-1,2,3,4-tetrahydroisoquinolin-4-yl)isophthalic acid 800 mg (1.9 mmol) of 4-(3,5-bis(trifluoromethylphenyl)-6,8-dichloro-2-methyl-1,2,3,4-tetrahydroisoquinoline (intermediate 3) were introduced into a mixture of 6 ml of chlorosulfonic acid and 5 ml of conc. $H_2SO_4$ and subsequently heated to 100° C. for 6 hours. For workup, the mixture was added to ice, and the precipitate was filtered off with suction and dried to obtain 772 mg of the desired isophthalic acid as the hydrogen sulfate.

24: 5-(6,8-dichloro-2-methyl-1,2,3,4-tetrahydroisoquinolin-4-yl)-N,N'-bis(2-hydroxy-1-hydroxymethylethyl)isophthalamide hydrochloride 95 mg of intermediate 4 were dissolved in 4 ml of DMF and a solution of 75.9 mg (0.75 mmol) of triethylamine and 164 mg (0.5 mmol) of TOTU in 3 ml of DMF was added at 0° C. The mixture was stirred at 0° C. for 30 minutes and at room temperature for 30 minutes. The resulting solution was added to a solution of 46 mg (0.5 mmol) of 2-amino-1,3-propanediol in 5 ml of DMF. After adding a further 50.6 mg (0.5 mmol) of triethylamine, the mixture was stirred at room temperature. For workup, the solvent was removed in vacuo and the residue purified on silica gel. After a further purification on a preparative HPLC, the product fractions were concentrated, dissolved in 1 N HCl and freeze-dried to isolate 48 mg of the title compound.

Example 25

5-(6,8-dichloro-2-methyl-1,2,3,4-tetrahydroisoquinolin-4-yl)-N,N'-bis(2-hydroxy-1,1-bishydroxymethylethyl)isophthalamide hydrochloride and

Example 26

5-(6,8-dichloro-2-methyl-1,2,3,4-tetrahydroisoquinolin-4-yl)-N-(2-hydroxy-1,1-bishydroxymethylethyl)isophthalamide hydrochloride

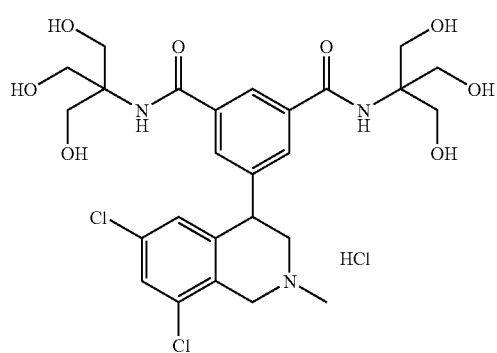

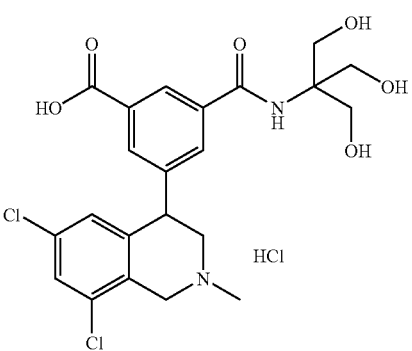

95 mg of 5-(6,8-dichloro-2-methyl-1,2,3,4-tetrahydroisoquinolin-4-yl)isophthalic acid (intermediate 4, Example 24)

were reacted with 2-amino-2-hydroxymethylpropane-1,3-diol in a TOTU-mediated reaction in a similar manner to the method described in Example 24. In the subsequent purification on silica gel, 2 fractions could be isolated which were both subjected to a further purification on a preparative HPLC.

Concentration of the product fractions, dissolution in dilute HCl and subsequent freeze-drying afforded 17 mg of the title compound for Example 25, and also 33 mg of the title compound for Example 26.

Example 27

5-(6,8-dichloro-2-methyl-1,2,3,4-tetrahydroisoquinolin-4-yl)-N,N'-bis((2S,3R,4R,5R)-2,3,4,5,6-pentahydroxyhexyl)isophthalamide hydrochloride and

Example 28

5-(6,8-dichloro-2-methyl-1,2,3,4-tetrahydroisoquinolin-4-yl)-N-((2S,3R,4R,5R)-2,3,4,5,6-pentahydroxyhexyl)isophthalamide hydrochloride

Example 29

(S)-2-[3-((S)-1-carboxy-2-hydroxyethylcarbamoyl)-5-(6,8-dichloro-2-methyl-1,2,3,4-tetrahydroisoquinolin-4-yl)benzoylamino]-3-hydroxypropionic acid hydrochloride

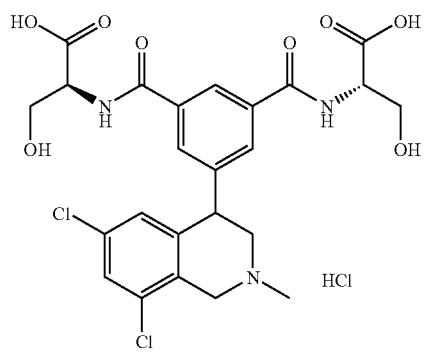

Intermediate 1: tert-butyl (S)-3-tert-butoxy-2-[3-((S)-2-tert-butoxy-1-tert-butoxycarbonylethylcarbamoyl)-5-(6,8-dichloro-2-methyl-1,2,3,4-tetrahydroisoquinolin-4-yl)benzoylamino]propionate 95 mg of 5-(6,8-dichloro-2-methyl-1,2,3,4-tetrahydroisoquinolin-4-yl)isophthalic acid (intermediate 4, Example 24)

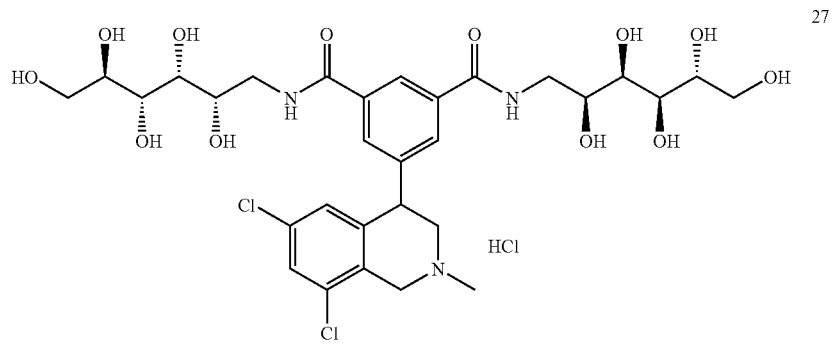

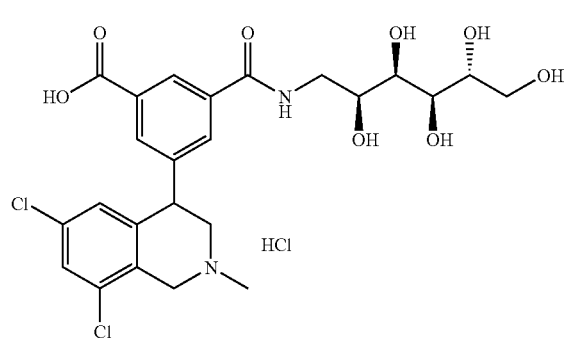

Starting from 95 mg of 5-(6,8-dichloro-2-methyl-1,2,3,4-tetrahydroisoquinolin-4-yl)isophthalic acid (intermediate 4, Example 24), a similar procedure to the method described in Examples 25/26 afforded 11 mg of Example compound 27, and also 29 mg of Example compound 28.

were reacted in a similar manner to the TOTU coupling described in Example 24 with 127 mg of tert-butyl (S)-2-amino-3-tert-butoxypropionate hydrochloride to obtain 200 mg of the title compound after chromatography on silica gel.

29: (S)-2-[3-((S)-1-carboxy-2-hydroxyethylcarbamoyl)-5-(6,8-dichloro-2-methyl-1,2,3,4-tetrahydroisoquinolin-4-yl)benzoylamino]-3-hydroxypropionic acid hydrochloride 200 mg of intermediate 1 were stirred in 5 ml of trifluoroacetic acid at room temperature for 1 hour. Subsequently, the solvent was removed in vacuo, and the residue was triturated with ether and filtered off with suction. The trifluoroacetate obtained in this way was dissolved in dilute HCl and freeze-dried to obtain 109 mg of the title compound.

Example 30

N-[3-(6,8-dichloro-2-methyl-1,2,3,4-tetrahydroisoquinolin-4-yl)phenyl]-(S)-2-amino-5-guanidinopentanamide hydrochloride

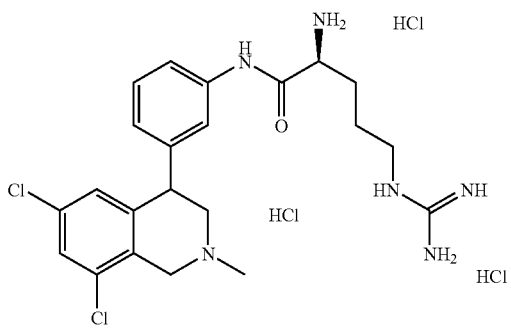

Intermediate 1: N-[3-(6,8-dichloro-2-methyl-1,2,3,4-tetrahydroisoquinolin-4-yl)phenyl]-2S-tert-butoxycarbonylamino-5-(N',N''-di-tert-butoxycarbonyl)-guanidinopentanamide 570 mg (1.2 mmol) of (S)-5-(N',N''-di-tert-butoxycarbonylguanidino)-2-tert-butoxycarbonylaminopentanoic acid were initially charged in 10 ml of DMF and 405 mg (4.0 mmol) of triethylamine were added. After cooling to 0° C., 406 mg (3.0 mmol) of HOBt, 379 mg (3.0 mmol) of DIC and 61 mg (0.5 mmol) of DMAP were added. Afterwards, the mixture was admixed at 0° C. with a solution of 307 mg (1.0 mmol) of 3-(6,8-dichloro-2-methyl-1,2,3,4-tetrahydroisoquinolin-4-yl)phenylamine (Example 2, intermediate 1) in 6 ml of DMF and stirred at room temperature. For workup, the solvent was removed in vacuo, and the residue was taken up in ethyl acetate and washed with saturated NaHCO$_3$ solution. The organic phase was removed and the aqueous extracted once more with ethyl acetate. The combined organic phases were washed once with 2 N HCl and once with H$_2$O, dried over MgSO$_4$ and concentrated by rotary evaporation. After subsequent chromatography on silica gel, 237 mg of the title compound were obtained.

30: N-[3-(6,8-dichloro-2-methyl-1,2,3,4-tetrahydroisoquinolin-4-yl)phenyl]-(S)-2-amino-5-guanidinopentanamide hydrochloride 237 mg of intermediate 1 were dissolved in 5 ml of dichloromethane and admixed at 0° C. with 1 ml of trifluoroacetic acid. The mixture was allowed to warm to room temperature and was stirred for 24 hours. Afterwards, the mixture was freed of solvents and codistilled once with toluene. The product obtained in this way was dissolved in 25 ml of 0.1 N HCl, filtered and freeze-dried. Repeated dissolution in H$_2$O and subsequent freeze-drying afforded 162 mg of the title compound.

Example 31

N-[4-(6,8-dichloro-2-methyl-1,2,3,4-tetrahydroisoquinolin-4-yl)phenyl]-(S)-2-amino-5-guanidinopentanamide trifluoroacetate

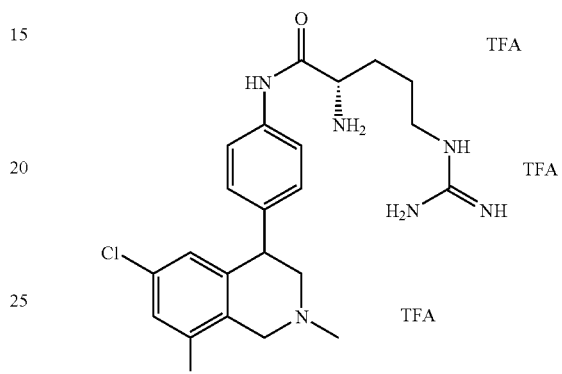

Starting from 4-(6,8-dichloro-2-methyl-1,2,3,4-tetrahydroisoquinolin-4-yl)phenylamine (Example 1, intermediate 6) and (S)-5-(N',N''-di-tert-butoxycarbonylguanidino)-2-tert-butoxycarbonylaminopentanoic acid, a similar procedure to the method described in Example 30 with subsequent treatment with trifluoroacetic acid afforded the title compound as the trifluoroacetate.

Example 32

(S)-2-amino-N-[3-(6,8-dichloro-2-methyl-1,2,3,4-tetrahydroisoquinolin-4-yl)phenyl]-3-(1H-imidazol-4-yl)propionamide trifluoroacetate

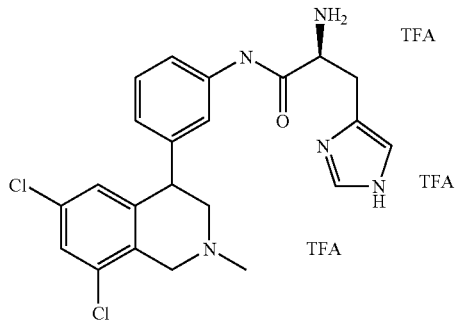

The title compound was prepared in a similar manner to the procedure described in Example 30 starting from 3-(6,8-dichloro-2-methyl-1,2,3,4-tetrahydroisoquinolin-4-yl) phenylamine (Example 2, intermediate 1) and tert-butyl 4-((S)-2-tert-butoxycarbonylamino-2-carboxyethyl)imidazole-1-carboxylate with subsequent treatment with trifluoroacetic acid.

Example 33

(S)-2-amino-N-[4-(6,8-dichloro-2-methyl-1,2,3,4-tetrahydroisoquinolin-4-yl)phenyl]-3-(1H-imidazol-4-yl)propanamide trifluoroacetate

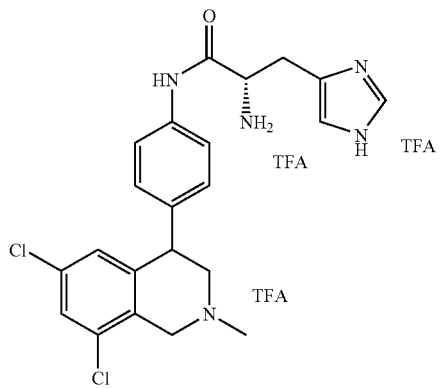

The title compound was prepared in a similar manner to the procedure described in Example 30 starting from 4-(6,8-dichloro-2-methyl-1,2,3,4-tetrahydroisoquinolin-4-yl)phenylamine (Example 1, intermediate 6) and tert-butyl 4-((S)-2-tert-butoxycarbonylamino-2-carboxyethyl)imidazole-1-carboxylate with subsequent treatment with trifluoroacetic acid.

Example 34

Ethyl {3-[4-(6,8-dichloro-2-methyl-1,2,3,4-tetrahydroisoquinolin-4-yl)-phenyl]ureido}acetate hydrochloride

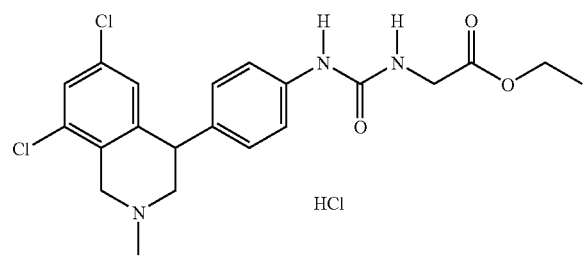

4-(6,8-Dichloro-2-methyl-1,2,3,4-tetrahydroisoquinolin-4-yl)phenylamine (95 mg, example 1, intermediate 6) was dissolved in acetonitrile (2 ml) and ethyl isocyanatoacetate (30 mg) was added dropwise with stirring. After four hours, the solution was concentrated and the residue purified by means of preparative HPLC. The product-containing fractions were combined, the acetonitrile was removed on a rotary evaporator, and the aqueous residue was neutralized with potassium carbonate and extracted three times with ethyl acetate. Drying over magnesium sulfate was followed by drying. The residue was taken up with aqueous hydrochloric acid and freeze-dried. 107 mg of the desired compound were obtained.

Example 35

Ethyl {3-[3-(6,8-dichloro-2-methyl-1,2,3,4-tetrahydroisoquinolin-4-yl)-phenyl]ureido}acetate hydrochloride

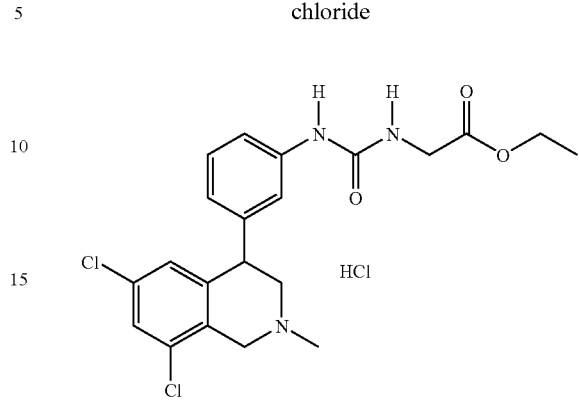

In a similar manner to example 34, 3-(6,8-dichloro-2-methyl-1,2,3,4-tetrahydro-isoquinolin-4-yl)phenylamine (example 2, intermediate 1) and ethyl isocyanatoacetate were reacted.

Example 36

Ethyl {3-[2-(6,8-dichloro-2-methyl-1,2,3,4-tetrahydroisoquinolin-4-yl)-phenyl]ureido}acetate hydrochloride

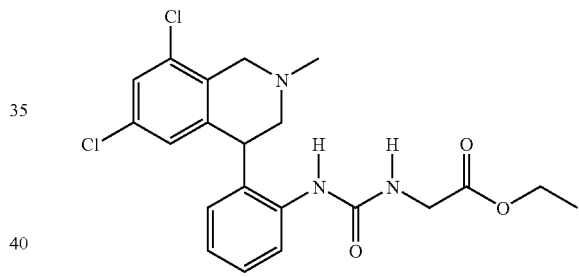

In a similar manner to example 34, 2-(6,8-dichloro-2-methyl-1,2,3,4-tetrahydro-isoquinolin-4-yl)phenylamine (example 3, intermediate 5) and ethyl isocyanatoacetate were reacted.

Example 37

{3-[3-(6,8-Dichloro-2-methyl-1,2,3,4-tetrahydroisoquinolin-4-yl)phenyl]-ureido}acetic acid, trifluoroacetic acid salt

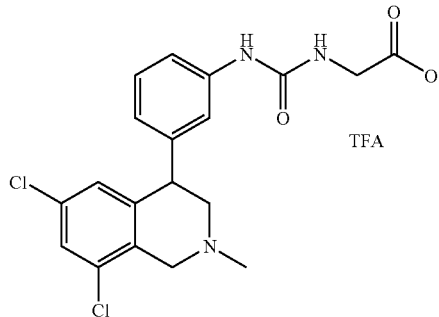

Ethyl 3-[3-(6,8-dichloro-2-methyl-1,2,3,4-tetrahydroisoquinolin-4-yl)phenyl]ureido}acetate hydrochloride (9 mg, example 35) was admixed with water (2 ml) and saturated potassium carbonate solution (0.25 ml) and stirred for 48 h. Aqueous 2 N hydrochloric acid was used to adjust the pH to 2, the solvent was removed and the residue purified by means of preparative HPLC. The product-containing fractions were combined, the acetonitrile removed on a rotary evaporator and the residue freeze-dried. 6 mg of the desired compound were obtained.

Example 38

{3-[4-(6,8-Dichloro-2-methyl-1,2,3,4-tetrahydroisoquinolin-4-yl)phenyl]-ureido}acetic acid, trifluoroacetic acid salt

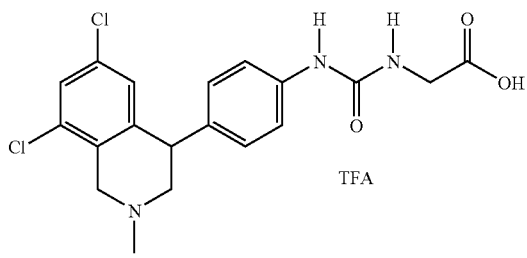

In a similar manner to example 4, ethyl 3-[4-(6,8-dichloro-2-methyl-1,2,3,4-tetrahydro-isoquinolin-4-yl)phenyl]ureido}acetate hydrochloride was hydrolyzed.

Example 39

{3-[2-(6,8-Dichloro-2-methyl-1,2,3,4-tetrahydroisoquinolin-4-yl)phenyl]-ureido}acetic acid, trifluoroacetic acid salt

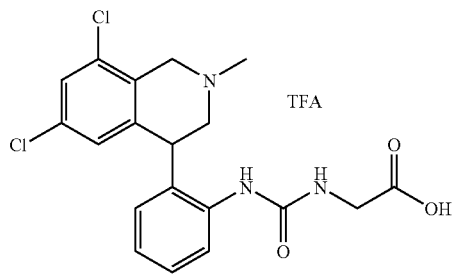

In a similar manner to example 4, ethyl 3-[2-(6,8-dichloro-2-methyl-1,2,3,4-tetrahydro-isoquinolin-4-yl)phenyl]ureido}acetate hydrochloride (example 36) was hydrolyzed.

Example 40

Ethyl {3-[3-(6,8-dichloro-2-methyl-1,2,3,4-tetrahydroisoquinolin-4(R or S)-yl)phenyl]ureido}acetate

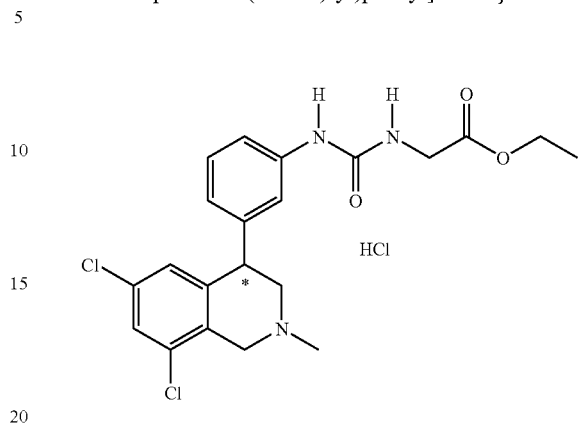

In a similar manner to example 34, 3-(6,8-dichloro-2-methyl-1,2,3,4-tetrahydro-isoquinolin-4(R or S)-yl)phenylamine (example 20, intermediate 1, enantiomer B) and ethyl isocyanatoacetate were reacted, except that dichloromethane was used as the solvent instead of acetonitrile.

Example 41

Ethyl {3-[2-(6,8-dichloro-2-methyl-1,2,3,4-tetrahydroisoquinolin-4(R or S)-yl)phenyl]ureido}acetate

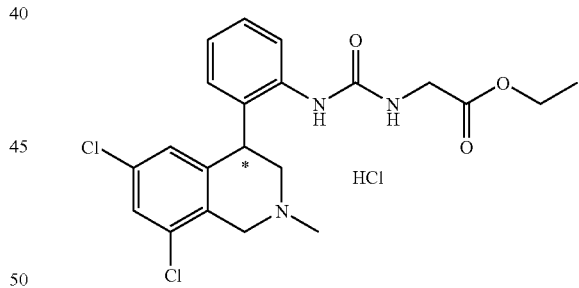

Intermediate 1

(R)-2-(6,8-dichloro-2-methyl-1,2,3,4-tetrahydroisoquinolin-4-yl)phenylamine and (S)-2-(6,8-dichloro-2-methyl-1,2,3,4-tetrahydroisoquinolin-4-yl)phenylamine 2-(6,8-dichloro-2-methyl-1,2,3,4-tetrahydroisoquinolin-4-yl-phenylamine (example 3, intermediate 5) was separated into the enantiomers on a chiral phase.

Preparative Separation Conditions:
Chiral column: Chiralpak AD10 35×10 cm
Solvent: acetonitrile
Flow rate: 300 ml/min Analytical Data on a Chiral Phase:
Chiral column: Chiralpak ADH 250×4.6 mm,
Solvent: acetonitrile
Flow rate: 1 ml/min
Temperature: 30° C.
Retention time of enantiomer A: 5.1 min
Retention time of enantiomer B: 7.3 min In a similar manner to example 40, 2-(6,8-dichloro-2-methyl-1,2,3,4-tetrahydro-isoquinolin-4(R or S)-yl)phenylamine (enantiomer B) and ethyl isocyanatoacetate were reacted.

Example 42

Ethyl {3-[4-(6,8-dichloro-2-methyl-1,2,3,4-tetrahydroisoquinolin-4(R or S)-yl)phenyl]ureido}acetate

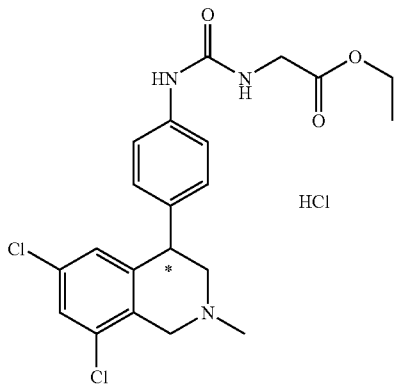

Intermediate 1

(R)-4-(6,8-dichloro-2-methyl-1,2,3,4-tetrahydroisoquinolin-4-yl)phenylamine and (S)-4-(6,8-dichloro-2-methyl-1,2,3,4-tetrahydroisoquinolin-4-yl)phenylamine 4-(6,8-dichloro-2-methyl-1,2,3,4-tetrahydroisoquinolin-4-yl)-phenylamine (example 1, intermediate 6) was separated into the enantiomers on a chiral phase.

Preparative Separation Conditions:
Chiral column: Chiralpak AD10 35×10 cm
Solvent: MeOH/0.1% DEA
Flow rate: 300 ml/min Analytical Data on a Chiral Phase:
Chiral column: Chiralpak ADH 250×4.6 mm,
Solvent: MeOH/0.1% DEA
Flow rate: 1 ml/min
Temperature: 30° C.
Retention time of enantiomer A: 4.8 min
Retention time of enantiomer B: 7.6 min In a similar manner to example 40, 4-(6,8-dichloro-2-methyl-1,2,3,4-tetrahydro-isoquinolin-4(R or S)-yl)phenylamine (enantiomer B) and ethyl isocyanatoacetate were reacted.

Example 43

{3-[4-(6,8-Dichloro-2-methyl-1,2,3,4-tetrahydroisoquinolin-4(R or S)-yl)-phenyl]ureido}acetic acid, trifluoroacetic acid salt

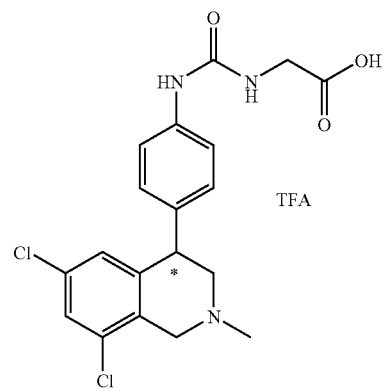

In a similar manner to example 4, ethyl {3-[4-(6,8-dichloro-2-methyl-1,2,3,4-tetrahydroisoquinolin-4(R or S)-yl)phenyl]ureido}acetate hydrochloride (example 42) was hydrolyzed, except that ethanol served as the solvent and aqueous sodium hydroxide solution as the base.

Example 44

{3-[2-(6,8-Dichloro-2-methyl-1,2,3,4-tetrahydroisoquinolin-4(R or S)-yl)-phenyl]ureido}acetic acid, trifluoroacetic acid salt

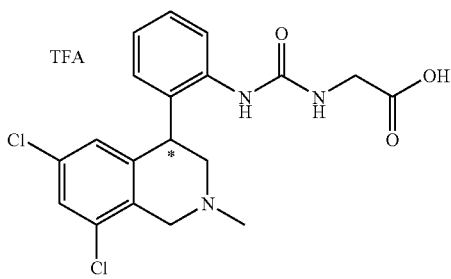

Ethyl {3-[2-(6,8-dichloro-2-methyl-1,2,3,4-tetrahydroisoquinolin-4(R or S)-yl)phenyl]ureido}acetate hydrochloride (430 mg, example 41) was initially charged in water (35 ml) and admixed with 10% hydrochloric acid with stirring. After 3 hours under reflux, the mixture was hydrolyzed. The solvent was removed and the residue purified by means of preparative HPLC. The product-containing fractions were combined, and the solvent removed on a rotary evaporator. The residue was further purified using silica gel (1:1 ethyl acetate/methanol), the product-containing fractions were combined, the solvent was removed on a rotary evaporator and the residue was freeze-dried. 45 mg of the desired compound were obtained.

Example 45

{3-[3-(6,8-Dichloro-2-methyl-1,2,3,4-tetrahydroisoquinolin-4(R or S)-yl)-phenyl]ureido}acetic acid, trifluoroacetic acid salt

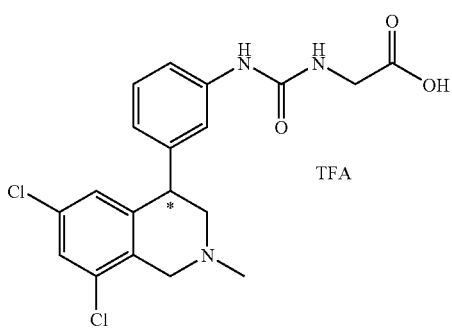

In a similar manner to example 4, ethyl {3-[3-(6,8-dichloro-2-methyl-1,2,3,4-tetrahydroisoquinolin-4(R or S)-yl)phenyl]ureido}acetate hydrochloride (example 40) was hydrolyzed, except that the acetonitrile solvent was dispensed with.

Example 46

2-Methoxyethyl [4-(6,8-dichloro-2-methyl-1,2,3,4-tetrahydroisoquinolin-4(R or S)-yl)phenyl]carbamate

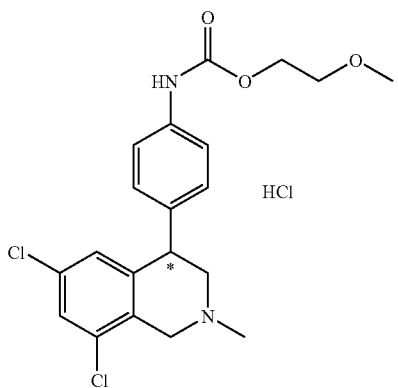

4-(6,8-Dichloro-2-methyl-1,2,3,4-tetrahydroisoquinolin-4(R or S)-yl)phenylamine (70 mg, example 20, intermediate 1, enantiomer B) was dissolved in methylene chloride (4.5 ml) and a solution of 2-methoxyethyl chloroformate (39 mg) in methylene chloride (0.5 ml) was slowly added dropwise with stirring. After leaving to stand overnight, the solvent was removed and the residue purified by means of preparative HPLC. The product-containing fractions were combined, the acetonitrile removed on a rotary evaporator, and the residue admixed with hydrochloric acid and freeze-dried. 80 mg of the desired compound were obtained.

Example 47

2-Methoxyethyl [3-(6,8-dichloro-2-methyl-1,2,3,4-tetrahydroisoquinolin-4(R or S)-yl)phenyl]carbamate

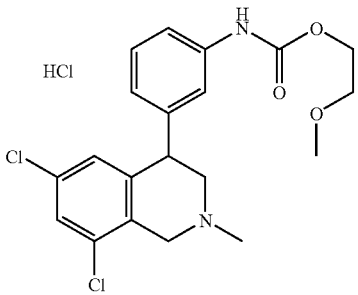

In a similar manner to example 13, 3-(6,8-dichloro-2-methyl-1,2,3,4-tetrahydro-isoquinolin-4-yl)phenylamine (example 2, intermediate 1) was reacted with 2-methoxyethyl chloroformate. However, chromatography could be dispensed with.

Conditions

Prep. HPLC:

Unless stated otherwise, the preparative HPLC was carried out under the following conditions:

stationary phase: Merck Purospher RP18 (10 μM) 250×25 mm mobile phase: 90% $H_2O$ (0.05% TFA)→90% acetonitrile; 40 min; 25 ml/min LCMS methods:

Method A:

Stationary phase: YMC, J'sphere ODS, H80 20×24 μ;

Mobile phase: 0 min, 90% $H_2O$ (0.05% TFA); 2.5 min, 95% ACN; 3.3 min. 95% ACN; 3.35 min, 90% $H_2O$; 1 ml/min; 30° C.

Method B:

Stationary phase: Merck Purosphere 3μ 2×55 mm;

Mobile phase: 0 min, 95% $H_2O$ (0.05% TFA); 4 min, 95% ACN; 5.5 min, 95% ACN; 6.5 min, 95% $H_2O$; 0.5 ml/min; 30° C.

Method C:

Stationary phase: Merck Purosphere 5 μ 2×55 mm;

Mobile phase: 0 min, 95% $H_2O$ (0.05% TFA); 3 min, 95% ACN; 4.5 min, 95% ACN; 5.5 min, 95% $H_2O$; 0.5 ml/min; 30° C.

Method D:

Stationary phase: YMC, J'sphere ODS, H80 20×2 4μ;

Mobile phase: 0 min, 90% $H_2O$ (0.05% TFA); 1.9 min, 95% ACN; 2.4 min, 95% ACN; 2.45 min, 90% $H_2O$; 1 ml/min; 30° C.

Method E:

Stationary phase: Merck Purosphere 5μ 2×55 mm;

Mobile phase: 0 min, 95% $H_2O$ (0.05% TFA); 3.5 min, 95% ACN; 4.5 min, 95% ACN; 5.5 min, 95% $H_2O$; 0.5 ml/min; 30° C.

Method F:

Stationary phase: YMC J'sphere ODS H80 20×2.1 mm

Mobile phase: 90% H$_2$O (0.05% TFA)→95% acetonitrile; 1.9 min; 95% acetonitrile; 0.5 min→10% acetonitrile; 0.05 min; 1 ml/min.

Method G:

Stationary phase: YMC J'sphere ODS H80 20×2.1 mm

Mobile phase: 96% H$_2$O (0.05% TFA)→95% acetonitrile; 2.0 min; 95% acetonitrile; 0.4 min→4% acetonitrile;. 0.05 min; 1 ml/min.

TABLE 1

Analytical data of the example compounds

| Example No. | Retention time*) | Method | M + H$^+$ | Method |
|---|---|---|---|---|
| 1 | 1.402 | A | 485.1 | ESI |
| 1a | 1.774 | C | 485.3 | ESI |
| 2 | 1.469 | A | 485.1 | ESI |
| 2a | 3.420 | B | 485.1 | ESI |
| 3 | 1.512 | A | 485.1 | ESI |
| 3a | 1.519 | A | 485.1 | ESI |
| 4a | 1.828 | C | 485.2 | ESI |
| 4b | 1.806 | C | 485.3 | ESI |
| 5 | 0.879 | D | 485.1 | ESI |
| 6 | 0.933 | D | 424.2 | ESI |
| 6a | 0.937 | D | 424.2 | ESI |
| 7 | 0.951 | D | 454.2 | ESI |
| 7a | 0.958 | D | 454.1 | ESI |
| 8 | 0.902 | D | 514.2 | ESI |
| 8a | 0.9121 | D | 514.2 | ESI |
| 9 | 0.891 | D | 512.1 | ESI |
| 10 | 0.979 | D | 458.1 | ESI |
| 11 | 0.883 | D | 435.2 | ESI |
| 12 | 0.973 | D | 438.1 | ESI |
| 12a | 0.970 | D | 438.2 | ESI |
| 13 | 0.945 | D | 465.2 | ESI |
| 14 | 0.834 | D | 499.1 | ESI |
| 15 | 0.887 | D | 409.1 | ESI |
| 16 | 0.959 | D | 423.1 | ESI |
| 17 | 2.081 | E | 451.1 | ESI |
| 18 | 2.027 | E | 450.1 | ESI |
| 19 | 0.925 | D | 507.2 | ESI |
| 20 | 0.959 | D | 465.1 | ESI |
| 21 | 0.982 | D | 438.1 | ESI |
| 22 | 0.971 | D | 454.2 | ESI |
| 23 | 0.925 | D | 514.2 | ESI |
| 24 | 0.633 | D | 526.1 | ESI |
| 25 | 0.711 | D | 586.2 | ESI |
| 26 | 0.853 | D | 483.1 | ESI |
| 27 | 0.402 | D | 706.1 | ESI |
| 28 | 0.803 | D | 543.1 | ESI |
| 29 | 0.820 | D | 554.1 | ESI |
| 30 | 0.772 | D | 463.2 | ESI |
| 31 | 1.805 | E | 463.2 | ESI |
| 32 | 1.917 | E | 444.1 | ESI |
| 33 | 1.817 | E | 444.1 | ESI |
| 34 | 1.14 | F | 436.5 | ESI |
| 35 | 1.15 | F | 436.5 | ESI |
| 36 | 1.13 | F | 436.5 | ESI |
| 37 | 1.08 | F | 408.4 | ESI |
| 38 | 1.00 | F | 408.4 | ESI |
| 39 | 1.04 | F | 408.4 | ESI |
| 40 | 1.15 | F | 436.5 | ESI |
| 41 | 1.13 | F | 436.5 | ESI |
| 42 | 1.05 | G | 436.5 | ESI |
| 43 | 0.94 | G | 408.1 | ESI |
| 44 | 0.95 | G | 408.1 | ESI |
| 45 | 0.96 | G | 408.1 | ESI |
| 46 | 1.10 | G | 409.1 | ESI |
| 47 | 1.13 | F | 409.1 | ESI |

*)The retention times relate to the mass spectra.

Pharmacological Data:

Test Description:

This test determines the recovery of the intracellular pH (pH$_i$) after acidification, and this recovery occurs in the case of functional NHE even under bicarbonate-free conditions. To this end, the pH$_i$ was determined using the pH-sensitive fluorescent dye BCECF (Calbiochem, the BCECF-AM precursor was used). The cells were initially loaded with BCECF. The BCECF fluorescence was determined in a Ratio Fluorescence Spectrometer (Photon Technology International, South Brunswick, N.J., USA) at excitation wavelengths of 505 and 440 nm and an emission wavelength of 535 nm and converted to the pH$_i$ by means of calibration curves. The cells had already been incubated in NH$_4$Cl buffer (pH 7.4) in the course of the BCECF loading (NH$_4$Cl buffer: 115 mM NaCl, 20 mM NH$_4$Cl, 5 mM KCl, 1 mM CaCl$_2$, 1 mM MgSO$_4$, 20 mM Hepes, 5 mM glucose, 1 mg/ml BSA; a pH of 7.4 was established using 1 M NaOH). The intracellular acidification was induced by adding 975 µl of an NH$_4$Cl-free buffer (see below) to 25 µl aliquots of the cells incubated in NH$_4$Cl buffer. The subsequent rate of the pH recovery was registered at 2 minutes for NHE1, at 5 minutes for NHE2 and at three minutes for NHE3. For the calculation of the inhibitory potency of the tested substances, the cells were initially investigated in buffers in which complete or absolutely no pH recovery took place. For complete pH recovery (100%), the cells were incubated in Na$^+$-containing buffer (133.8 mM NaCl, 4.7 mM KCl, 1.25 mM CaCl$_2$, 1.25 mM MgCl$_2$, 0.97 mM Na$_2$HPO$_4$, 0.23 mM NaH$_2$PO$_4$, 5 mM Hepes, 5 mM glucose, a pH of 7.0 was established using 1 M NaOH). For the determination of the 0% value, the cells were incubated in an Na$^+$-free buffer (133.8 mM choline chloride, 4.7 mM KCl, 1.25 mM CaCl$_2$, 1.25 mM MgCl$_2$, 0.97 mM K$_2$HPO$_4$, 0.23 mM KH$_2$PO$_4$, 5 mM Hepes, 5 mM glucose, a pH of 7.0 was established using 1 M NaOH). The substances to be tested were made up in the Na$^+$-containing buffer. The recovery of the intracellular pH at each tested concentration of a substance was expressed in percent of the maximum recovery. The percentages of the pH recovery were used to calculate the IC$_{50}$ value of the particular substance for the individual NHE subtypes by means of the program Sigma-Plot.

The inhibitory data of some example compounds were shown by way of example in Table 2.

TABLE 2

Inhibitory data of some example compounds on NHE3

| Example compound | IC$_{50}$ value (µM) |
|---|---|
| 2 | 0.0036 |
| 13 | 0.0176 |
| 16 | 0.1594 |
| 31 | 0.0291 |

While there have been described and pointed out fundamental novel features of the invention as applied to a preferred embodiment thereof, it will be understood that various omissions and substitutions and changes, in the form and details of the packages and methods illustrated, may be made by those skilled in the art without departing from the spirit of the invention. For example, it is expressly intended that all combinations of those elements and/or method steps which perform substantially the same function in substantially the same way to achieve the same results are within the scope of the invention.

The invention is not limited by the embodiments described above which are presented as examples only but can be modified in various ways within the scope of protection defined by the appended patent claims.

What is claimed is:

1. A compound of formula I, a pharmaceutically acceptable salt or a trifluoroacetate thereof

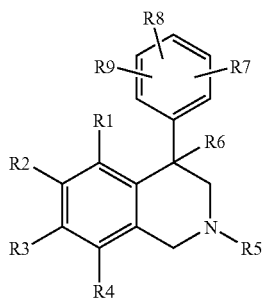

wherein:
R1, R2, R3 and R4 are each independently selected from the group consisting of H, F, Cl, Br, I, CN, $NO_2$, OH, an alkyl having 1, 2, 3, 4, 5, 6, 7 or 8 carbon atoms with none, some or all of the carbon atoms being fluorinated, a cycloalkyl having 3, 4, 5, 6, 7 or 8 carbon atoms with none, some or all of the carbon atoms being fluorinated, O-alkyl having 1, 2, 3, 4, 5, 6, 7 or 8 carbon atoms with optionally some or all of the carbon atoms being fluorinated, $O_k$—$(CH_2)_l$-phenyl, heteroaryl having 0, 1, 2, 3 or 4 nitrogen atoms and 0 or 1 oxygen atom and 0 or 1 sulfur atom, $O_h$—$SO_j$—R10, NR14R15, CONR16R17, COOR18 and OCOR18, wherein
k is 0 or 1;
l is 0, 1, 2, 3 or 4;
h is 0 or 1;
j is 0, 1 or 2;
R10 is selected from the group consisting of alkyl having 1, 2, 3, 4, 5, 6, 7 or 8 carbon atoms with none, some or all of the carbon atoms being fluorinated, OH, O-alkyl having 1, 2, 3, 4, 5, 6, 7 or 8 carbon atoms with none, some or all of the carbon atoms being fluorinated, and NR11R12, wherein
R11 and R12 are each independently selected from the group consisting of hydrogen, alkyl having 1, 2, 3, 4, 5, 6, 7 or 8 carbon atoms with none, some or all of the carbon atoms being fluorinated and further having one or more $CH_2$ groups which may be replaced by O, NR13, CO, CS, where R13 is H or alkyl having 1, 2, 3, 4, 5, 6, 7 or 8 carbon atoms with none, some or all of the carbon atoms being fluorinated; or
R11 and R12 are both bonded to the nitrogen atom which is part of a 5- or 6-membered ring;
R14 and R15 are each independently selected from the group consisting of H, or alkyl having 1, 2, 3, 4, 5, 6, 7 or 8 carbon atoms with none, some or all of the carbon atoms fluorinated and further having one or more $CH_2$ groups which may be optionally replaced by 0, CO, CS or NR19, or
R14 and R15 are, together with the nitrogen atom which bonds them, part of a 5- or 6-membered ring;
R16 and R17 are each independently selected from the group consisting of H or alkyl having 1, 2, 3, 4, 5, 6, 7 or 8 carbon atoms with none, some or all of the carbon atoms being fluorinated and further having one or more $CH_2$ groups which may be replaced by O, CO, CS or NR19, or
R16 and R17 are, together with the nitrogen atom which bonds them, part of a 5- or 6-membered ring;
R18 is H or alkyl having 1, 2, 3, 4, 5, 6, 7 or 8 carbon atoms with none, some or all of the carbon atoms being fluorinated;
R19 is H or alkyl having 1, 2, 3 or 4 carbon atoms with none, some or all of the carbon atoms being fluorinated;
R5 is selected from the group consisting of H, alkyl having 1, 2, 3, 4, 5, 6, 7 or 8 carbon atoms with none, some or all of the carbon atoms being fluorinated, cycloalkyl having 3, 4, 5, 6, 7 or 8 carbon atoms with none, some or all of the carbon atoms being fluorinated, COR20 and $SO_2$R20; wherein
R20 is H or alkyl having 1, 2, 3 or 4 carbon atoms with none, some or all of the carbon atoms being fluorinated;
R6 is selected from the group consisting of H, OH, F, Cl, Br, alkyl having 1, 2, 3, 4, 5, 6, 7 or 8 carbon atoms with none, some or all of the carbon atoms being fluorinated, cycloalkyl having 3, 4, 5, 6, 7 or 8 carbon atoms with none, some or all of the carbon atoms being fluorinated, O-alkyl having 1, 2, 3, 4, 5, 6, 7 or 8 carbon atoms with none, some or all of the carbon atoms being fluorinated, and O-acyl having 1, 2, 3, 4, 5, 6, 7 or 8 carbon atoms with none, some or all of the carbon atoms being fluorinated;
R7, R8 and R9 are each independently selected from the group consisting of H, F, Cl, Br, I, OH, alkyl having 1, 2, 3, 4, 5, 6, 7 or 8 carbon atoms with none, some or all of the carbon atoms being fluorinated, cycloalkyl having 3, 4, 5, 6, 7 or 8 carbon atoms with none, some or all of the carbon atoms being fluorinated, O-alkyl having 1, 2, 3, 4, 5, 6, 7 or 8 carbon atoms with none, some or all of the carbon atoms being fluorinated, $O_v$—$SO_w$—R47, COR47, COOR60, NR51R52 and a hydrophilic -L-G group; wherein
v is 0 or 1;
w is 2 or 3;
R47 is selected from the group consisting of H, alkyl having 1, 2, 3, 4, 5, 6, 7 or 8 carbon atoms with none, some or all of the carbon atoms being fluorinated, and NR48R49; where
R48 and R49 are each independently H or alkyl which has 1, 2, 3, 4, 5, 6, 7 or 8 carbon atoms with none, some or all of the carbon atoms being fluorinated and further has one or more $CH_2$ groups which may be replaced by O, CO, CS or NR50, where
R50 is H or alkyl having 1, 2, 3, 4, 5 or 6 carbon atoms with none, some or all of the carbon atoms being fluorinated;
Or, R48 and R49 are, together with the nitrogen atom which bonds them, part of a 5, 6, 7 or 8-membered ring;
R60 is H or alkyl having 1, 2, 3, 4, 5, 6, 7 or 8 carbon atoms with none, some or all of the carbon atoms being fluorinated;
R51 andR52 are each independently selected from the group consisting H, alkyl having 1, 2, 3, 4, 5, 6, 7 or 8 carbon atoms with none, some or all of the carbon atoms being fluorinated, and acyl which has 1, 2, 3, 4, 5, 6, 7 or 8 carbon atoms with none, some or all of the carbon atoms being fluorinated and further has one or more $CH_2$ groups which may be replaced by O or NR53, where R53 is H or alkyl having 1, 2, 3, 4, 5 or 6 carbon atoms with none, some or all of the carbon atoms being fluorinated;

or R51 and R52 are, together with the nitrogen atom which bonds them, part of a 5, 6, 7 or 8-membered ring;

L is selected from the group consisting of —NR30CO—, —CONR30-, —NR30CONR31- or —NR30COO—, and R30 and R31 are each independently H, alkyl having 1, 2, 3, 4, 5, 6, 7 or 8 carbon atoms with none, some or all of the carbon atoms being fluorinated, or cycloalkyl having 3, 4, 5, 6, 7 or 8 carbon atoms with none, some or all of the carbon atoms being fluorinated;

G is a $C_a(OR32)_xH_{2a+1-x}$ group which has one or more $CH_2$ groups that may be replaced by O or NR33, a $C_b(OR32)_yH_{2b-1-y}$ group which has one or more $CH_2$ groups that may be replaced by O or NR33, a $C_cH_{2c+1}$ group which has two or more $CH_2$ groups that may be replaced by O or NR33, or a —$(CH_2)_z$—COOR34 group, a —$(CH_2)_z$—$SO_3$R34 group, a —$(CH_2)_z$—$N^+$R35R36R37 group where one or more hydrogen atoms of the —$(CH_2)_z$ units may be replaced by OR32, —CR38R39-COOR40 or —CR38R39NR41R42, where a is 2, 3, 4, 5, 6, 7 or 8;

x is 2, 3, 4, 5, 6, 7 or 8;

R32 is H, alkyl having 1, 2, 3, 4, 5 or 6 carbon atoms with none, some or all of the carbon atoms being fluorinated, or acyl having 1, 2, 3, 4, 5 or 6 carbon atoms with none, some or all of the carbon atoms being fluorinated;

R33 is H or alkyl having 1, 2, 3, 4, 5 or 6 carbon atoms with none, some or all of the carbon atoms being fluorinated;

b is 3, 4, 5, 6 or 7;

y is 2, 3, 4, 5, 6 or 7;

c is 3, 4, 5, 6, 7 or 8;

z is 0, 1, 2, 3 or 4;

R34, R35, R36 and R37 are each independently H or alkyl having 1, 2, 3, 4, 5 or 6 carbon atoms of with none, some or all of the carbon atoms being fluorinated;

R38 is —$(CH_2)_n$—Y; where n is 0, 1, 2, 3 or 4;

Y is H, alkyl which has 1, 2, 3, 4, 5, 6, 7 or 8 carbon atoms with none, some or all of the carbon atoms being fluorinated and further has one or more $CH_2$ groups that may be replaced by O, S or NR43, or Y is —COOR44, —CONR45R46, —NHC(NH)$NH_2$, phenyl or heteroaryl, said phenyl and heteroaryl radicals being capable of being substituted by up to three substituents selected from the group consisting of $CH_3$, $CF_3$, OH, $OCH_3$ and $NH_2$;

R43, R44, R45 and R46 are each independently H or alkyl having 1, 2, 3, 4, 5 or 6 carbon atoms with none, some or all of the carbon atoms being fluorinated;

R39 is H or alkyl having 1, 2, 3, 4, 5, 6, 7 or 8 carbon atoms with none, some or all of the carbon atoms being fluorinated;

R40 is H or alkyl having 1, 2, 3, 4, 5, 6, 7 or 8 carbon atoms with none, some or all of the carbon atoms being fluorinated;

R41 and R42 are each independently H, alkyl having 1, 2, 3, 4, 5, 6, 7 or 8 carbon atoms with none, some or all of the carbon atoms being fluorinated, or acyl having 1, 2, 3, 4, 5, 6, 7 or 8 carbon atoms with none, some or all of the carbon atoms being fluorinated;

provided that at least one of the R7, R8 or R9 radicals in formula I is a -L-G group.

2. A compound of claim 1, wherein:

R1, R2, R3 and R4, are each independently selected from the group consisting of H, F, Cl, Br, I, CN, $NO_2$, OH, alkyl having 1, 2, 3 or 4 carbon atoms with none, some or all of the carbon atoms being fluorinated, cycloalkyl having 3, 4, 5 or 6 carbon atoms with none, some or all of the carbon atoms being fluorinated, O-alkyl having 1, 2, 3 or 4 carbon atoms with none, some or all of the carbon atoms being fluorinated, O-phenyl, $SO_2$R10, NR14R15, CONR16R17, COOR18 and OCOR18; where R10 is selected from the group consisting of alkyl having 1, 2, 3 or 4 carbon atoms with none, some or all of the carbon atoms being fluorinated, OH and NR11R12; where R11 and R12 are each independently selected from the group consisting of hydrogen, alkyl having 1, 2, 3 or 4 carbon atoms with none, some or all of the carbon atoms being fluorinated, and acyl having 1, 2, 3 or 4 carbon atoms with none, some or all of the carbon atoms being fluorinated, or R11 and R12 are, together with the nitrogen atom which bonds them, part of a 5- or 6-membered ring which is of a type selected from the group consisting of 1-pyrrolyl, 1-piperidinyl, 1-piperazinyl, 1 -N-methylpiperazinyl and 4-morpholinyl;

R14 and R15 are each independently selected from the group consisting of H, alkyl having 1, 2, 3 or 4 carbon atoms with none, some or all of the carbon atoms being fluorinated, and acyl having 1, 2, 3 or 4 carbon atoms with none, some or all of the carbon atoms being fluorinated, or R14 and R15 are, together with the nitrogen atom which bonds them, part of a 5- or 6-membered ring which is of a type selected from the group consisting of 1-pyrrolyl, 1-piperidinyl, 1-piperazinyl, 1-N-methylpiperazinyl and 4-morpholinyl;

R16 and R17 are each independently H or alkyl having 1, 2, 3 or 4 carbon atoms with none, some or all of the carbon atoms being fluorinated, or R16 and R17 are together with the nitrogen atom which bonds them, part of a 5- or 6-membered ring which is of a type selected from the group consisting of 1-pyrrolyl, 1-piperidinyl, 1-piperazinyl, 1-N-methylpiperazinyl and 4-morpholinyl;

R18 is H or alkyl having 1, 2, 3 or 4 carbon atoms with none, some or all of the carbon atoms being fluorinated;

R5 is H, alkyl having 1, 2, 3 or 4 carbon atoms with none, some or all of the carbon atoms being fluorinated, or cycloalkyl having 3, 4, 5 or 6 carbon atoms with none, some or all of the carbon atoms being fluorinated;

R6 is selected from the group consisiting of H, OH, F, Cl, Br, alkyl having 1, 2, 3 or 4 carbon atoms with none, some or all of the carbon atoms being fluorinated, cycloalkyl having 3, 4, 5 or 6 carbon atoms with none, some or all of the carbon atoms being fluorinated, O-alkyl having 1, 2, 3 or 4 carbon atoms with none, some or all of the carbon atoms being fluorinated, and O-acyl having 1, 2, 3 or 4 carbon atoms with none, some or all of the carbon atoms being fluorinated;

R7, R8 and R9 are each independently selected from the group consisting of H, F, Cl, Br, I, OH, alkyl having 1, 2, 3 or 4 carbon atoms with none, some or all of the carbon atoms being fluorinated, cycloalkyl having 3, 4, 5 or 6 carbon atoms with none, some or all of the carbon atoms being fluorinated, O-alkyl having 1, 2, 3 or 4 carbon atoms with none, some or all of the carbon atoms being fluorinated, $O_v$—$SO_w$—R47, COR47, COOR60, NR51R52 and a -L-G group; where v is 0 or 1;

w is 2 or 3;

R47 is H, alkyl having 1, 2, 3 or 4 carbon atoms with none, some or all of the carbon atoms being fluorinated, or NR48R49; where R48 and R49 are each independently H, alkyl having 1, 2, 3 or 4 carbon atoms with none, some or all of the carbon atoms being fluorinated, or acyl having 1, 2, 3 or 4 carbon atoms with none, some or all of the carbon atoms being fluorinated, or R48 and R49 are, together with the nitrogen atom which bonds them, part of a 5- or 6-membered ring which is of a type selected from the group consisting of 1-pyrrolyl, 1-piperidinyl, 1-piperazinyl, 1-N-methylpiperazinyl and 4-morpholinyl;

R60 is H, alkyl having 1, 2, 3 or 4 carbon atoms with none, some or all of the carbon atoms being fluorinated;

R51 and R52 are each independently H, alkyl having 1, 2, 3 or 4 carbon atoms with none, some or all of the carbon atoms being fluorinated, or acyl having 1, 2, 3 or 4 carbon atoms with none, some or all of the carbon atoms being fluorinated, or R51 and R52 are, together with the nitrogen atom which bonds them, part of a 5- or 6-membered ring which is of a type selected from the group consisting of 1-pyrrolyl, 1-piperidinyl, 1-piperazinyl, 1-N-methylpiperazinyl and 4-morpholinyl;

L is —NR3 CO—, —CONR30-, —NR30CONR31-, —NR30COO— wherein R30 and R31 are each independently H, alkyl having 1, 2, 3 or 4 carbon atoms with none, some or all of the carbon atoms being fluorinated, or cycloalkyl having 3, 4, 5 or 6 carbon atoms with none, some or all of the carbon atoms being fluorinated;

G is a $C_a(OR32)_xH_{2a+1-x}$ group which has one or more $CH_2$ groups that may be replaced by O or NR33, a $C_b(OR32)_yH_{2b-1-y}$ group which has one or more $CH_2$ groups that may be replaced by O or NR33, a $C_cH_{2c+1}$ group which has two or more $CH_2$ groups being replaced by O or NR33, a —$(CH_2)_z$—COOR34 group, a —$(CH_2)_z$—$SO_3$R34 group, a —$(CH_2)_z$—$N^+$R35R36R37 group which has one or more hydrogen atoms of the —$(CH_2)_z$ units that may be replaced by OR32 groups, a —CR38R39-COOR40 group, or a —CR38R39NR41R42 group; where a is 2, 3, 4, 5, 6, 7 or 8;

x is 2, 3, 4, 5, 6, 7 or 8;

R32 is H, alkyl having 1, 2, 3 or 4 carbon atoms with none, some or all of the carbon atoms being fluorinated, or acyl having 1, 2, 3 or 4 carbon atoms with none, some or all of the carbon atoms being fluorinated;

R33 is H or alkyl having 1, 2, 3 or 4 carbon atoms with none, some or all of the carbon atoms being fluorinated;

b is 3, 4, 5, 6 or 7;

y is 2, 3, 4, 5, 6 or 7;

c is 3, 4, 5, 6, 7 or 8;

z is 0, 1, 2, 3 or 4;

R34, R35, R36 and R37 are each independently H or alkyl having 1, 2, 3 or 4 carbon atoms with none, some or all of the carbon atoms being fluorinated;

R38 is —$(CH_2)_n$—Y; where n is 0, 1, 2, 3 or 4;

Y is H or alkyl which has 1, 2, 3 or 4 carbon atoms with none, some or all of the carbon atoms being fluorinated and further has one or more $CH_2$ groups that may be replaced by O, S or NR43, or Y is COOR44, CONR45R46, NHC(NH)$N_2$, phenyl or heteroaryl, whre the phenyl or heteroaryl radicals may be substituted by Lip to three substituents selected from the group consisting of $CH_3$, $CF_3$, OH, $OCH_3$ and $NH_2$;

R43, R44, R45 and R46 are each independently H or alkyl having 1, 2, 3 or 4 carbon atoms with none, some or all of the carbon atoms being fluorinated;

R39 is H or alkyl having 1, 2, 3 or 4 carbon atoms with none, some or all of the carbon atoms being fluorinated;

R40 is H or alkyl having 1, 2, 3 or 4 carbon atoms with none, some or all of the carbon atoms being fluorinated;

R41 and R42 are each independently H, alkyl having 1, 2, 3 or 4 carbon atoms with none, some or all of the carbon atoms being fluorinated, or acyl having 1, 2, 3 or 4 carbon atoms with none, some or all of the carbon atoms being fluorinated;

provided that at least one of the R7, R8 or R9 is an -L-G group.

3. A compound of claim 2 wherein,

R1, R2, R3 and R4, are each independently selected from the group consisting of H, F, Cl, Br, CN, $NO_2$, OH, $CH_3$, $CH_2CH_3$, $CF_3$, $CH_2CF_3$, $OCH_3$, $_{OCH2}$ $CH_3$, $OCF_3$, $OCH_2CF_3$, $SO_2R10$, NR14R15, CONR16R17, COOR18 and OCOR18, where R10 is $CH_3$, $CH_2CH_3$, $CF_3$, $CH_2CF_3$, OH, or NR11R12, where R11 and R12 are each independently H, $CH_3$, $CH_2CH_3$, $CF_3$, $CH_2CF_3$, $COCH_3$, $COCH_2CH_3$, $COCF_3$ or $COCH_2$ $CF_3$, or 11 and R12 are, together with the nitrogen atom which bonds them, part of a 5- or 6-membered ring which is of a type selected from the group consisting 1-pyrrolyl, 1-piperidinyl, 1-piperazinyl, 1-N-methylpiperazinyl and 4-morpholinyl;

R14 and R15 are each independently H, $CH_3$, $CH_2CH_3$, $CF_3$, $CH_2CF_3$, $COCH_3$, $COCH_2CH_3$, $COCF_3$ or $COCH_2CF_3$, or R14 and R15 are, together with the nitrogen atom which bonds them, part of a 5- or 6-membered ring which is of a type selected from the group consisting of 1-pyrrolyl, 1-piperidinyl, 1-piperazinyl, 1-N-methylpiperazinyl and 4-morpholinyl;

R16 and R17 are each independently H, $CH_3$, $CH_2CH_3$, $CF_3$ or $CH_2CF_3$, or R16 and R17 are, together with the nitrogen atom which bonds them, part of a 5- or 6-membered ring which is of a type selected from the group consisting of 1-pyrrolyl, 1-piperidinyl, 1-piperazinyl, 1-N-methylpiperazinyl and 4-morpholinyl;

R18 is H, $CH_3$, $CH_2CH_3$, $CF_3$ or $CH_2CF_3$;

R5 is H, $CH_3$, $CH_2CH_3$, $CF_3$ or $CH_2CF_3$;

R6 is H, OH, $CH_3$, $CH_2CH_3$, $CF_3$, $CH_2CF_3$, $OCH_3$, $OCH_2CH_3$, $OCF_3$, $OCH_2CF_3$;

R7, R8 and R9 are each independently H, F, Cl, Br, I, OH, $CH_3$, $CH_2CH_3$, $CF_3$, $CH_2CF_3$, $OCH_3$, $OCH_2CH_3$, $OCF_3$, $OCH_2CF_3$, $SO_2R47$, $SO_3R60$, COR47, COOR60, NR51R52 or a -L-G group; where R47 is H, $CH_3$, $CH_2CH_3$, $CF_3$, $CH_2CF_3$ or NR48R49; where R48 and R49 are each independently H, $CH_3$, $CH_2CH_3$, $CF_3$, $CH_2\,CF_3$, $COCH_3$, $COCH_2CH_3$, $COCF_3$ or $COCH_2CF_3$, or R48 and R49 are, together with the nitrogen atom which bonds them, part of a 5- or 6-membered ring which is of a type selected from the group consisting of 1-pyrrolyl, 1-piperidinyl, 1-piperazinyl, 1-N-methylpiperazinyl and 4-morpholinyl;

R60 is H, $CH_3$, $CH_2CH_3$, $CF_3$, or $CH_2CF_3$;

R51 and R52 are each independently H, $CH_3$, $CH_2CH_3$, $CF_3$, $CH_2CF_3$, $COCH_3$, $COCH_2CH_3$, $COCF_3$ or $COCH_2CF_3$, or R51 and R52 are, together with the nitrogen atom which bonds them, part of a 5- or 6-membered ring which is of a type selected from the group consisting of 1-pyrrolyl, 1-piperidinyl, 1-piperazinyl, 1-N-methylpiperazinyl and 4-morpholinyl;

L is —NR30CO—, —CONR30-, —NR30CONR31-, or —NR30COO—, and where

R30 and R31 are each independently H, $CH_3$, $CH_2CH_3$, $CF_3$ or $CH_2CF_3$;

G is a $C_a(OR32)_xH_{2a+1-x}$ group which has one or more $CH_2$ groups that may be replaced by O or NR33, a $C_b(OR32)_yH_{2b-1-y}$ group which has one or more $CH_2$ groups that may be replaced by O or NR33, a $C_cH_{2c+1}$ group which has two or more $CH_2$ groups that are replaced by O or NR33, a —$(CH_2)_z$—COOR34 group, a —$(CH_2)_z$—$SO_3R34$ group, a —$(CH_2)_z$—$N^+R35R36R37$ group which has 1 or 2 hydrogen atoms of the —$(CH_2)_z$ units that may be replaced by OR32 groups, a —CR38R39-COOR40 group, or a —CR38R39NR41R42 group; where a is 2, 3, 4, 5, 6, 7 or 8;

x is 2, 3, 4, 5, 6, 7 or 8;

R32 is H, $CH_3$, $CH_2CH_3$, $CF_3$, $CH_2CF_3$, $COCH_3$, $COCH_2CH_3$, $COCF_3$ or $COCH_2CF_3$;

R33 is H, $CH_3$, $CH_2CH_3$, $CF_3$ or $CH_2CF_3$;

b is 3, 4, 5, 6 or 7;

y is 2, 3, 4, 5, 6 or 7;

c is 3, 4, 5, 6, 7 or 8;

z is 1 or 2;

R34, R35, R36 and R37 are each independently H, $CH_3$, $CH_2CH_3$, $CF_3$ or $CH_2CF_3$;

R38 is —$(CH_2)_n$—Y; where n is 0, 1, 2, 3 or 4;

Y is H, or alkyl which has 1, 2, 3 or 4 carbon atoms with none, some or all of which being fluorinated and further has one or more $CH_2$ groups that may be replaced by O, S or NR43, or Y is COOR44, CONR45R46, $NHC(NH)NH_2$, phenyl or heteroaryl, where said phenyl or heteroaryl may be substituted by up to 3 substituents independently selected from the group consisting of $CH_3$, $CF_3$, OH, $OCH_3$ and $NH_2$; where R43, R44, R45 and R46 are each independently H, $CH_3$, $CH_2CH_3$, $CF_3$ or $CH_2CF_3$;

R39 is H, $CH_3$, $CH_2CH_3$, $CF_3$ or $CH_2CF_3$;

R40 is H, $CH_3$, $CH_2CH_3$, $CF_3$ or $CH_2CF_3$;

R41 and R42 are each independently H, $CH_3$, $CH_2CH_3$, $CF_3$, $CH_2CF_3$, $COCH_3$, $COCH_2CH_3$, $COCF_3$ or $COCH_2CF_3$;

provided that at least one of the R7, R8 or R9 radicals is a -L-G group.

4. A compound of claim 3, wherein

R1, R2, R3 and R4, are each independently H, F, Cl, Br, CN, $NO_2$, OH, —$CH_3$, —$CH_2CH_3$, —$CF_3$, $CH_2CF_3$, $OCH_3$, $OCH_2CH_3$, $OCF_3$, $OCH_2CF_3$, $SO_2R10$, NR14R15, CONR16R17, COOR18 or OCOR18; where R10 is $CH_3$, $CH_2CH_3$, $CF_3$, $CH_2CF_3$, OH or NR11R12; where R11 and R12 are each independently H, $CH_3$, $CH_2CH_3$, $CF_3$, $CH_2CF_3$, $COCH_3$, $COCH_2CH_3$, $COCF_3$ or $COCH_2CF_3$;

R14 and R15 are each independently H, $CH_3$, $CH_2CH_3$, $CF_3$, $CH_2CF_3$, $COCH_3$, $COCH_2CH_3$, $COCF_3$ or $COCH_2CF_3$;

R16 and R17 are each independently H, $CH_3$, $CH_2CH_3$, $CF_3$ or $CH_2CF_3$;

R18 is H, $CH_3$, $CH_2CH_3$, $CF_3$ or $CH_2CF_3$;

R5 is $CH_3$;

R6 is H;

R7, R8 and R9 are each independently H, F, Cl, Br, I, OH, $CH_3$, $CH_2CH_3$, $CF_3$, $CH_2CF_3$, $OCH_3$, $OCH_2CH_3$, $OCF_3$, $OCH_2CF_3$, $SO_2R47$, $SO_3R60$, COR47, COOR60, NR51R52 or a -L-G group; where R47 is H, $CH_3$, $CH_2CH_3$, $CF_3$, $CH_2CF_3$ or NR48R49; where R48 and R49 are each independently H, $CH_3$, $CH_2CH_3$, $CF_3$, $CH_2CF_3$, $COCH_3$, $COCH_2CH_3$, $COCF_3$ or $COCH_2CF_3$, or R48 and R49 are, together with the nitrogen atom which bonds them, part of a 5- or 6-membered ring which is of a type selected from the group consisting of 1-pyrrolyl, 1-piperidinyl, 1-piperazinyl, 1-N-methylpiperazinyl and 4-morpholinyl;

R60 is H, $CH_3$, $CH_2CH_3$, $CF_3$, or $CH_2CF_3$;

R51 and R52 are each independently H, $CH_3$, $CH_2CH_3$, $CF_3$, $CH_2CF_3$, $COCH_3$, $COCH_2CH_3$, $COCF_3$ or $COCH_2CF_3$ or R51 and R52 are, together with the nitrogen atom which bonds them, part of a 5- or 6-membered ring which is of a type selected from the group consisting of 1-pyrrolyl, 1-piperidinyl, 1-piperazinyl, 1-N-methylpiperazinyl and 4-morpholinyl;

L is —NR30CO—, —CONR30-, —NR30CONR31-, OR—NR30COO—, and where

R30 and R31 are each independently H, —$CH_3$, —$CH_2CH_3$, —$CF_3$ or —$CH_2CF_3$;

G is a $C_a(OR32)_xH_{2a+1-x}$ group which has one or more $CH_2$ groups that may be replaced by O or NR33, a $C_b(OR32)_yH_{2b-1-y}$ group which has one or more $CH_2$ groups that may be replaced by O or NR33, a $C_cH_{2c+1}$ group which has two or more $CH_2$ groups that are replaced by O or NR33, a —$(CH_2)_z$—COOR34 group, a —$(CH_2)_z$—$SO_3R34$ group, a —$(CH^2)_z$—$N^{30}$ R35R36R37 group which has 1 or 2 hydrogen atoms of the —$(CH_2)_z$ units that may be replaced by OR32 groups, a —CR38R39—COOR40 group or a —CR38R39NR41R42 group; where
a is 2, 3, 4, 5, 6, 7 or 8;
x is 2, 3, 4, 5, 6, 7 or 8;
R32 is H, CH$_3$, CH$_2$CH$_3$, CF$_3$, CH$_2$CF$_3$, COCH$_3$, COCH$_2$CH$_3$, COCF$_3$ or COCH$_2$CF$_3$;
R33 is H, CH$_3$, $_{CH2}$CH$_3$, CF$_3$ or CH$_2$CF$_3$;
b is 3, 4, 5, 6 or 7;
y is 2, 3, 4, 5, 6 or 7;
c is 3, 4, 5, 6, 7 or 8;
z is 1 or 2;
R34, R35, R36 and R37 are each independently H, CH$_3$, CH$_2$CH$_3$, CF$_3$ or CH$_2$CF$_3$;
R38 is —(CH$_2$)$_n$—Y; where
n 0, 1, 2, 3 or 4;
Y is H, or alkyl which has 1, 2, 3 or 4 carbon atoms with none, some or all of the carbon atoms being fluorinated and further has one or more CH$_2$ groups that may be replaced by O, S or NR43, or Y is COOR44, CONR45R46, NHC(NH)N$_2$, phenyl or heteroaryl, where said phenyl or heteroaryl may be substituted by up to 3 substituents selected from the group consisting of CH$_3$, CF$_3$, OH, OCH$_3$ and NH$_2$; where
R43, R44, R45 and R46 are each independently H, CH$_3$, CH$_2$CH$_3$, CF$_3$ or CH$_2$CF$_3$,
R39 is H;
R40 is H, CH$_3$, CH$_2$CH$_3$, CF$_3$ or CH$_2$CF$_3$;
R41 and R42 are each independently H, CH$_3$, CH$_2$CH$_3$, CF$_3$, CH$_2$CF$_3$, COCH$_3$, COCH$_2$CH$_3$, COCF$_3$ or COCH$_2$CF$_3$;
provided that at least one of the R7, R8 or R9 radicals is a -L-G group.

5. A compound of claim 1 selected from the group consisting of
N-[4-(6,8-dichloro-2-methyl-1,2,3,4-tetrahydroisoquinolin-4-yl)phenyl]-2,3,4,5,6-pentahydroxyhexanamide,
N-[3-(6,8-dichloro-2-methyl-1,2,3,4-tetrahydroisoquinolin-4-yl)phenyl]-2,3,4,5,6-pentahydroxyhexanamide,
N-[2-(6,8-dichloro-2-methyl-1,2,3,4-tetrahydroisoquinolin-4-yl)phenyl]-2,3,4,5,6-pentahydroxyhexanamide,
N-[3-((S)-6,8-dichloro-2-methyl-1,2,3,4-tetrahydroisoquinolin-4-yl)phenyl]-2,3,4,5,6-pentahydroxyhexanamide,
N-[3-((R)-6,8-dichloro-2-methyl-1,2,3,4-tetrahydroisoquinolin-4-yl)phenyl]-2,3,4,5,6-pentahydroxyhexanamide,
1-[3-(6,8-dichloro-2-methyl-1,2,3,4-tetrahydroisoquinolin-4-yl)phenyl]-3-(2-hydroxy-1-hydroxymethylethyl)urea,
1-[3-(6,8-dichloro-2-methyl-1,2,3,4-tetrahydroisoquinolin-4-yl)phenyl]-3-(2-hydroxy-1,1-bishydroxymethylethyl)urea,
1-[3-(6,8-dichloro-2-methyl-1,2,3,4-tetrahydroisoquinolin-4-yl)phenyl]-3-(2,3,4,5,6-pentahydroxyhexyl)urea,
1-[3-(6,8-dichloro-2-methyl-1,2,3,4-tetrahydroisoquinolin-4-yl)phenyl]-3-(2,4,5-trihydroxy-6-hydroxymethyhetrahydropyran-3-yl)urea,
{N-[3-(6,8-dichloro-2-methyl-1,2,3,4-tetrahydroisoquinolin-4-yl)phenyl-N'-(1-sulfo-2-ethyl)}urea,
{N-[3-(6,8-dichloro-2-methyl-1,2,3,4-tetrahydroisoquinolin-4-yl)phenyl]-N'-(ethyl-2-trimethylammonium)}urea chloride,
{N-[3-(6,8-dichloro-2-methyl-1,2,3,4-tetrahydroisoquinolin-4-yl)phenyl]-N'(1-carboxy-3-hydroxy-2-propyl)}urea,
{N-[3-(6,8-dichloro-2-methyl-1,2,3,4-tetrahydroisoquinolin-4-yl)phenyl]-N'-(1-carboxy-4-aminocarboxy-2-butyl)}urea,
3-(6,8-dichloro-2-methyl-1,2,3,4-tetrahydroisoquinolin-4-yl)-N-(2,3,4,5,6-pentahydroxyhexyl)benzamide,
3-(6,8-dichloro-2-methyl-1,2,3,4-tetrahydroisoquinolin-4-yl)-N-(2-hydroxy-1-hydroxymethylethyl)benzamide,
2-[3-(6,8-dichloro-2-methyl-1,2,3,4-tetrahydroisoquinolin-4-yl)benzoylamino]-3-hydroxypropionic acid,
2-[3-(6,8-dichloro-2-methyl-1,2,3,4-tetrahydroisoquinolin-4-yl)benzoylamino]succinic acid,
2-[3-(6,8-dichloro-2-methyl-1,2,3,4-tetrahydroisoquinolin-4-yl)benzoylamino]-4-succinamic acid,
N-[3-(6,8-dichloro-2-methyl-1,2,3,4-tetrahydroisoquinolin-4-yl)phenyl]-N'-[1-carboxy-5-guanidino-2-pentyl]urea,
{N-[3-(6,8-dichloro-2-methyl-1,2,3,4-tetrahydroisoquinolin-4-yl)phenyl]-N'-(1-carboxy-4-aminocarboxy-2-butyl)}urea,
{N-[3-(6,8-dichloro-2-methyl-1,2,3,4-tetrahydroisoquinolin-4-yl)phenyl]-N'-(1-carboxy-3-hydroxy-2-propyl)}urea,
1-[3-(6,8-dichloro-2-methyl-1,2,3,4-tetrahydroisoquinolin-4-yl)phenyl]-3-(2-hydroxy -1,1-bishydroxymethylethyl)urea,
1-[3-(6,8-dichloro-2-methyl-1,2,3,4-tetrahydroisoquinolin-4-yl)phenyl]-3-(2,3,4,5,6-pentahydroxyhexyl)urea,
5-(6,8-dichloro-2-methyl-1,2,3,4-tetrahydroisoquinolin-4-yl)-N,N'-bis(2-hydroxy-1-hydroxymethylethyl) isophthalamide,
5-(6,8-dichloro-2-methyl-1,2,3,4-tetrahydroisoquinolin-4-yl)-N,N'-bis(2-hydroxy-1,1-bishydroxymethylethyl) isophthalamide,
5-(6,8-dichloro-2-methyl-1,2,3,4-tetrahydroisoquinolin-4-yl)-N-bis(2-hydroxy-1,1-bishydroxymethylethyl) isophthalamide,
5-(6,8-dichloro-2-methyl-1,2,3,4-tetrahydroisoquinolin-4-yl)-N,N'-bis(2,3,4,5,6-pentahydroxyhexyl)isophthalamide,
5-(6,8-dichloro-2-methyl-1,2,3,4-tetrahydroisoquinolin-4-yl)-N-(2,3,4,5,6-pentahydroxyhexyl)isophthalamide,
2-[3-(1-carboxy-2-hydroxyethylcarbamoyl)-5-(6,8-dichloro-2-methyl-1,2,3,4-tetrahydroisoquinolin-4-yl) benzoylamino]-3-hydroxypropionic acid,
N-[3-(6,8-dichloro-2-methyl-1,2,3,4-tetrahydroisoquinolin-4-yl)phenyl]-2-amino-5-guanidinopentanamide,
N-[4-(6,8-dichloro-2-methyl-1,2,3,4-tetrahydroisoquinolin-4-yl)phenyl]-2-amino-5-guanidinopentanamide,
2-amino-N-[3-(6,8-dichloro-2-methyl-1,2,3,4-tetrahydroisoquinolin-4-yl)phenyl]-3-(1H-imidazol-4-yl)propionamide,
2-amino-N-[4-(6,8-dichloro-2-methyl-1,2,3,4-tetrahydroisoquinolin-4-yl)phenyl]-3-(1H-imidazol-4-yl)propionamide,
ethyl{3-[4-(6,8-dichloro-2-methyl-1,2,3,4-tetrahydroisoquinolin-4-yl)phenyl]ureido}-acetate,
ethyl{3-[3-(6,8-dichloro-2-methyl-1,2,3,4-tetrahydroisoquinolin-4-yl)phenyl]ureido}-acetate,
ethyl{3-[2-(6,8-dichloro-2-methyl-1,2,3,4-tetrahydroisoquinolin-4-yl)phenyl]ureido}-acetate,
{3-[3-(6,8-dichloro-2-methyl-1,2,3,4-tetrahydroisoquinolin-4-yl)phenyl]ureido}acetic acid,
{3-[4-(6,8-dichloro-2-methyl-1,2,3,4-tetrahydroisoquinolin-4-yl)phenyl]ureido}acetic acid,
{3-[2-(6,8-dichloro-2-methyl-1,2,3,4-tetrahydroisoquinolin-4-yl)phenyl]ureido}acetic acid, ethyl{3-[3-(6,8-dichloro-2-methyl-1,2,3,4-tetrahydroisoquinolin-4(R)-yl)phenyl]ureido}-acetate,
ethyl{3-[3-(6,8-dichloro-2-methyl-1,2,3,4-tetrahydroisoquinolin-4(S)-yl)phenyl]ureido}-acetate,
ethyl{3-[2-(6,8-dichloro-2-methyl-1,2,3,4-tetrahydroisoquinolin-4(R)-yl)phenyl]ureido}-acetate,
ethyl{3-[2-(6,8-dichloro-2-methyl-1,2,3,4-tetrahydroisoquinolin-4(S)-yl)phenyl]ureido}-acetate,
ethyl{3-[4-(6,8-dichloro-2-methyl-1,2,3,4-tetrahydroisoquinolin-4(R)-yl)phenyl]ureido}-acetate,
ethyl{3-[4-(6,8-dichloro-2-methyl-1,2,3,4-tetrahydroisoquinolin-4(S)-yl)phenyl]ureido}-acetate,
{3-[4-(6,8-dichloro-2-methyl-1,2,3,4-tetrahydroisoquinolin-4(R)-yl)phenyl]ureido}acetic acid,
{3-[4-(6,8-dichloro-2-methyl-1,2,3,4-tetrahydroisoquinolin-4(S)-yl)phenyl]ureido}acetic acid,
{3-[2-(6,8-dichloro-2-methyl-1,2,3,4-tetrahydroisoquinolin-4(R)-yl)phenyl]ureido}acetic acid,
{3-[2-(6,8-dichloro-2-methyl-1,2,3,4-tetrahydroisoquinolin-4(S)-yl)phenyl]ureido}acetic acid,
{3-[3-(6,8-dichloro-2-methyl-1,2,3,4-tetrahydroisoquinolin-4(R)-yl)phenyl]ureido}acetic acid,
{3-[3-(6,8-dichloro-2-methyl-1,2,3,4-tetrahydroisoquinolin-4(S)-yl)phenyl]ureido}acetic acid,
2-methoxyethyl[4-(6,8-dichloro-2-methyl-1,2,3,4-tetrahydroisoquinolin-4(R)-yl)phenyl]-carbamate,
2-methoxyethyl[4-(6,8-dichloro-2-methyl-1,2,3,4-tetrahydroisoquinolin-4(S)-yl)phenyl]-carbamate,
2-methoxyethyl[3-(6,8-dichloro-2-methyl-1,2,3,4-tetrahydroisoquinolin-4(R)-yl)phenyl]-carbamate, and
2-methoxyethyl[3-(6,8-dichloro-2-methyl-1,2,3,4-tetrahydroisoquinolin-4(S)-yl)phenyl]-carbamate.

6. A compound of claim 5 which is selected from the group consisting of

N-[4-(6,8-dichloro-2-methyl-1,2,3,4-tetrahydroisoquinolin-4-yl)phenyl]-(2R,3S,4R,5R)-2,3,4,5,6-pentahydroxyhexanamide,
N-[3-(6,8-dichloro-2-methyl-1,2,3,4-tetrahydroisoquinolin-4-yl)phenyl]-(2R,3S,4R,5R)-2,3,4,5,6-pentahydroxyhexanamide,
N-[2-(6,8-dichloro-2-methyl-1,2,3,4-tetrahydroisoquinolin-4-yl)phenyl]-(2R,3S,4R, 5R)-2,3,4,5,6-pentahydroxyhexanamide,
N-[3-((S)-6,8-dichloro-2-methyl-1,2,3,4-tetrahydroisoquinolin-4-yl)phenyl]-(2R,3S,4R,5R)-2,3,4,5,6-pentahydroxyhexanamide,
N-[3-((R)-6,3-dichloro-2-methyl-1,2,3,4-tetrahydroisoquinolin-4-yl)phenyl]-(2R,3S,4R,5R)-2,3,4,5,6-pentahydroxyhexanamide,
1-[3-(6,8-dichloro-2-methyl-1,2,3,4-tetrahydroisoquinolin-4-yl)phenyl]-3-(2-hydroxy-1-hydroxymethylethyl)urea,
1-[3-(6,8-dichloro-2-methyl-1,2,3,4-tetrahydroisoquinolin-4-yl)phenyl]-3-(2-hydroxy-1,1-bishydroxymethylethyl)urea,
1-[3-(6,8-dichloro-2-methyl-1,2,3,4-tetrahydroisoquinolin-4-yl)phenyl]-3-((2S,3R,4R,5R)-2,3,4,5,6-pentahydroxyhexyl)urea,
1-[3-(6,8-dichloro-2-methyl-1,2,3,4-tetrahydroisoquinolin-4-yl)phenyl]-3-((4R,5S,6R)-2,4,5-trihydroxy-6-hydroxymethyltetrahydropyran-3-yl)urea,
{N-[3-(6,8-dichloro-2-methyl-1,2,3,4-tetrahydroisoquinolin-4-yl)phenyl]-N'-(1-sulfo-2-ethyl)}urea,
{N-[3-(6,8-dichloro-2-methyl-1,2,3,4-tetrahydroisoquinolin-4-yl)phenyl]-N'-(ethyl-2-trimethylammonium)}urea chloride,
{N-[3-(6,8-dichloro-2-methyl-1,2,3,4-tetrahydroisoquinolin-4-yl)phenyl]-N'-(1-carboxy -3-hydroxy-2S-propyl)}urea,
{N-[3-(6,8-dichloro-2-methyl-1,2,3,4-tetrahydroisoquinolin-4-yl)phenyl]-N'-(1-carboxy -4-aminocarboxy-2S-butyl)}urea,
3-(6,8-dichloro-2-methyl-1,2,3,4-tetrahydroisoquinolin-4-yl)-N-((2S,3R,4R,5R) -2,3,4,5,6-pentahydroxyhexyl)benzamide,
3-(6,8-dichloro-2-methyl-1,2,3,4-tetrahydroisoquinolin-4-yl)-N-(2-hydroxy-1-hydroxymethylethyl)benzamide,
2-(S)-[3-(6,8-dichloro-2-methyl-1,2,3,4-tetrahydroisoquinolin-4-yl)benzoylamino]-3-hydroxypropionic acid,
2-(S)-[3-(6,8-dichloro-2-methyl-1,2,3,4-tetrahydroisoquinolin-4-yl)benzoylamino]succinic acid,
2-(S)-[3-(6,8-dichloro-2-methyl-1,2,3,4-tetrahydroisoquinolin-4-yl)benzoylamino]-4-succinamic acid,
N-[3-(6,8-dichloro-2-methyl-1,2,3,4-tetrahydroisoquinolin-4-yl)phenyl]-N'-[1-carboxy -5-guanidino-2S-pentyl]urea,
{N-[3-(6,8-dichloro-2-methyl-1,2,3,4-tetrahydroisoquinolin-4-(R)-yl)phenyl]-N'-(1-carboxy-4-aminocarboxy-2S-butyl)}urea,
{N-[3-(6,8-dichloro-2-methyl-1,2,3,4-tetrahydroisoquinolin-4-(S)-yl)phenyl]-N'-(1-carboxy-4-aminocarboxy-2S-butyl)}urea,
{N-[3-(6,8-dichloro-2-methyl-1,2,3,4-tetrahydroisoquinolin-4-(R)-yl)phenyl]-N'-(1-carboxy-3-hydroxy-2S-propyl)}urea,
{N-[3-(6,8-dichloro-2-methyl-1,2,3,4-tetrahydroisoquinolin-4-(S)-yl)phenyl]-N'-(1-carboxy-3-hydroxy-2S-propyl)}urea,
1-[3-(6,8-dichloro-2-methyl-1,2,3,4-tetrahydroisoquinolin-4-(R)-yl)phenyl]-3-(2-hydroxy-1,1-bishydroxymethylethyl)urea,
1-[3-(6,8-dichloro-2-methyl-1,2,3,4-tetrahydroisoquinolin-4-(S)-yl)phenyl]-3-(2-hydroxy-1,1-bishydroxymethylethyl)urea,
1-[3-((R)-6,8-dichloro-2-methyl-1,2,3,4-tetrahydroisoquinolin-4-yl)phenyl]-3-((2S,3R, 4R,5R)-2,3,4,5,6-pentahydroxyhexyl)urea,
1-[3-((S)-6,8-dichloro-2-methyl-1,2,3,4-tetrahydroisoquinolin-4-yl)phenyl]-3-((2S,3R, 4R,5R)-2,3,4,5,6-pentahydroxyhexyl)urea,
5-(6,8-dichloro-2-methyl-1,2,3,4-tetrahydroisoquinolin-4-yl)-N,N'-bis(2-hydroxy-1-hydroxymethylethyl) isophthalamide,
5-(6,8-dichloro-2-methyl-1,2,3,4-tetrahydroisoquinolin-4-yl)-N,N'-bis(2-hydroxy-1,1-bishydroxymethylethyl) isophthalamide,
5-(6,8-dichloro-2-methyl-1,2,3,4-tetrahydroisoquinolin-4-yl)-N-(2-hydroxy-1,1-bishydroxymethylethyl)isophthalamide,
5(6,8-dichloro-2-methyl-1,2,3,4-tetrahydroisoquinolin-4-yl)-N,N'-bis((2S,3R,4R, 5R)-2,3,4,5,6-pentahydroxyhexyl)isophthal amide,
5-(6,8-dichloro-2-methyl-1,2,3,4-tetrahydroisoquinolin-4-yl)-N-((2S,3R,4R,5R) -2,3,4,5,6-pentahydroxyhexyl)isophthalamide,
(S)-2-[((S)-1-carboxy-2-hydroxyethylcarbamoyl)-5-(6, 8-dichloro-2-methyl-1,2,3,4-tetrahydroisoquinolin-4-yl)benzoylamino]-3-hydroxypropionic acid,
(S)-N-[3-(6,8-dichloro-2-methyl-1,2,3,4-tetrahydroisoquinolin-4-yl)phenyl]-2-amino-5-guanidinopentanamide, (S)-N-[4-(6,8-dichloro-2-methyl-1,2,3,4-tetrahydroisoquinolin-4-yl)phenyl]-2-amino-5-guanidinopentanamide,
(S)-2-amino-N-[3-(6,8-dichloro-2-methyl-1,2,3,4-tetrahydroisoquinolin-4-yl)phenyl]-3-(1H-imidazol-4-yl) propionamide,
(S)-2-amino-N-[4-(6,8-dichloro-2-methyl-1,2,3,4-tetrahydroisoquinolin-4-yl)phenyl]-3-(1H-imidazol-4-yl) propionamide,
ethyl{3-[4-(6,8-dichloro-2-methyl-1,2,3,4-tetrahydroisoquinolin-4-yl)phenyl]ureido}-acetate,
ethyl{3-[3-(6,8-dichloro-2-methyl-1,2,3,4-tetrahydroisoquinolin-4-yl)phenyl]ureido}-acetate,
ethyl{3-[2-(6,8-dichloro-2-methyl-1,2,3,4-tetrahydroisoquinolin-4-yl)phenyl]ureido}-acetate,
{3-[3-(6,8-dichloro-2-methyl-1,2,3,4-tetrahydroisoquinolin-4-yl)phenyl]ureido}acetic acid,
{3-[4-(6,8-dichloro-2-methyl-1,2,3,4-tetrahydroisoquinolin-4-yl)phenyl]ureido}acetic acid,
{3-[2-(6,8-dichloro-2-methyl-1,2,3,4-tetrahydroisoquinolin-4-yl)phenyl]ureido}acetic acid,
ethyl{3-[3-(6,8-dichloro-2-methyl-1,2,3,4-tetrahydroisoquinolin-4(R)-yl)phenyl]ureido}-acetate,
ethyl{3-[3-(6,8-dichloro-2-methyl-1,2,3,4-tetrahydroisoquinolin-4(S)-yl)phenyl]ureido}-acetate,
ethyl{3-[2-(6,8-dichloro-2-methyl-1,2,3,4-tetrahydroisoquinolin-4(R)-yl)phenyl]ureido}-acetate,
ethyl{3-[2-(6,8-dichloro-2-methyl-1,2,3,4-tetrahydroisoquinolin-4(S)-yl)phenyl]ureido}-acetate,
ethyl{3-[4-(6,8-dichloro-2-methyl-1,2,3,4-tetrahydroisoquinolin-4(R)-yl)phenyl]ureido}-acetate,
ethyl{3-[4-(6,8-dichloro-2-methyl-1,2,3,4-tetrahydroisoquinolin-4(S)-yl)phenyl]ureido}-acetate,
{3-[4-(6,8-dichloro-2-methyl-1,2,3,4-tetrahydroisoquinolin-4(R)-yl)phenyl]ureido}acetic acid,
{3-[4-(6,8-dichloro-2-methyl-1,2,3,4-tetrahydroisoquinolin-4(S)-yl)phenyl]ureido}acetic acid,
{3-[2-(6,8-dichloro-2-methyl-1,2,3,4-tetrahydroisoquinolin-4(R)-yl)phenyl]ureido}acetic acid,
{3-[2-(6,8-dichloro-2-methyl-1,2,3,4-tetrahydroisoquinolin-4(S)-yl)phenyl]ureido}acetic acid,
{3-[3-(6,8-dichloro-2-methyl-1,2,3,4-tetrahydroisoquinolin-4(R)-yl)phenyl]ureido}acetic acid,
{3-[3-(6,8-dichloro-2-methyl-1,2,3,4-tetrahydroisoquinolin-4(S)-yl)phenyl]ureido}acetic acid,
2-methoxyethyl[4-(6,8-dichloro-2-methyl-1,2,3,4-tetrahydroisoquinolin-4(R)-yl)phenyl]-carbamate,
2-methoxyethyl[4-(6,8-dichloro-2-methyl-1,2,3,4-tetrahydroisoquinolin-4(S)-yl)phenyl]-carbamate,
2-methoxyethyl[3-(6,8-dichloro-2-methyl-1,2,3,4-tetrahydroisoquinolin-4(R)-yl)phenyl]-carbamate, and
2-methoxyethyl[3-(6,8-dichloro-2-methyl-1,2,3,4-tetrahydroisoquinolin-4(S)-yl)phenyl]-carbamate.

7. A medicament comprising a compound as recited in claim 1 for human, veterinary or phytoprotective use further comprising other pharmacological active ingredients in admixture with one or more pharmaceutically acceptable inactive excipients.

8. A method of treatment or prophylaxis, by administering to a mammal a medicament comprising a compound of claim 1 in a pharmaceutically acceptable formulation, for disorders of respiratory drive, respiratory disorders, sleep-related respiratory disorders, sleep apneas, snoring, of acute and chronic renal disorders, acute renal failure and of chronic renal failure, disorders of intestinal function, high blood pressure, essential hypertension, disorders of the central nervous system, disorders resulting from CNS over-excitability, epilepsy and centrally induced convulsions or of anxiety states, depressions and psychoses, ischemic states of the peripheral or central nervous system and of stroke, acute and chronic damage to and disorders of peripheral organs or limbs caused by ischemic or by reperfusion events, atherosclerosis, disorders of lipid metabolism, thromboses, disorders of biliary function, infestation by ectoparasites, disorders resulting from endothelial dysfunction, protozoal disorders, malaria, for the preservation and storage of transplants for surgical procedures, for use in surgical operations and organ transplantations or for the treatment of states of shock or of diabetes and late damage from diabetes or of diseases in which cellular proliferation represents a primary or secondary cause.

9. The method of claim 8, wherein said medicament further comprises another medicament or active ingredient.

10. A method of claim 8, wherein said method is for the treatment or prophylaxis of disorders of respiratory drive andlor of sleep-related respiratory disorders comprising sleep apneas.

11. A method of claim 8, wherein said method is for the treatment or prophylaxis of snoring.

12. A method of claim 8, wherein said method is for the treatment or prophylaxis of acute or chronic renal disorders, of acute renal failure and of chronic renal failure.

13. A method of claim 8, wherein said method is for the treatment or prophylaxis of disorders of intestinal function.

* * * * *